US008217026B2

(12) United States Patent
Crapo et al.

(10) Patent No.: US 8,217,026 B2
(45) Date of Patent: Jul. 10, 2012

(54) SUBSTITUTED PORPHYRINS

(75) Inventors: James D. Crapo, Englewood, CO (US); Brian J. Day, Englewood, CO (US); Michael P. Trova, Schenectady, NY (US); Polvina Jolicia F. Gauuan, Albany, NY (US); Douglas B. Kitchen, Schenectady, NY (US); Irwin Fridovich, Durham, NC (US); Ines Batinic-Haberle, Durham, NC (US)

(73) Assignees: Aeolus Sciences, Inc., Mission Viejo, CA (US); National Jewish Health, Durham, NC (US); Duke University, Denver, CO (US)

( * ) Notice: Subject to any disclaimer, the term of this patent is extended or adjusted under 35 U.S.C. 154(b) by 229 days.

(21) Appl. No.: 12/885,198

(22) Filed: Sep. 17, 2010

(65) Prior Publication Data

US 2011/0065679 A1    Mar. 17, 2011

Related U.S. Application Data

(60) Continuation of application No. 11/424,662, filed on Jun. 16, 2006, now Pat. No. 7,820,644, which is a division of application No. 10/349,171, filed on Jan. 23, 2003, now Pat. No. 7,189,707, which is a continuation of application No. 09/490,537, filed on Jan. 25, 2000, now Pat. No. 6,544,975.

(51) Int. Cl.
  *A01N 55/02* (2006.01)
  *A01N 43/36* (2006.01)
  *A61K 31/40* (2006.01)
  *C07B 47/00* (2006.01)
  *C07B 487/22* (2006.01)

(52) U.S. Cl. .................. 514/185; 514/410; 540/145

(58) Field of Classification Search .................. 540/145; 514/185, 410
See application file for complete search history.

(56) References Cited

U.S. PATENT DOCUMENTS

| | | |
|---|---|---|
| 2,951,799 A | 9/1960 | Sharp |
| 4,614,723 A | 9/1986 | Schmidt |
| 4,657,902 A | 4/1987 | Kappas et al. |
| 4,746,735 A | 5/1988 | Kruper, Jr. et al. |
| 4,758,422 A | 7/1988 | Quay |
| 4,829,984 A | 5/1989 | Gordon |
| 4,837,221 A | 6/1989 | Bonnett |
| 4,851,403 A | 7/1989 | Picker et al. |
| 4,861,760 A | 8/1989 | Mazuel et al. |
| 4,866,054 A | 9/1989 | Dori et al. |
| 4,885,114 A | 12/1989 | Gordon et al. |
| 4,892,941 A | 1/1990 | Dolphin et al. |
| 4,895,719 A | 1/1990 | Radhakrishnan |
| 4,911,920 A | 3/1990 | Jani et al. |
| 4,963,367 A | 10/1990 | Ecanow |
| 5,010,073 A | 4/1991 | Kappas et al. |
| 5,051,337 A | 9/1991 | Sakoda et al. |
| 5,087,438 A | 2/1992 | Gordon |
| 5,109,016 A | 4/1992 | Dixon et al. |
| 5,130,245 A | 7/1992 | Marklund et al. |
| 5,162,519 A | 11/1992 | Bonnett |
| 5,169,630 A | 12/1992 | Okaya et al. |
| 5,171,680 A | 12/1992 | Mullenbach et al. |
| 5,192,757 A | 3/1993 | Johnson et al. |
| 5,192,788 A | 3/1993 | Dixon et al. |
| 5,202,317 A | 4/1993 | Bruice |
| 5,212,162 A | 5/1993 | Missel et al. |
| 5,217,966 A | 6/1993 | Bruice |
| 5,223,538 A | 6/1993 | Fridovich |
| 5,227,405 A | 7/1993 | Fridovich |
| 5,236,914 A | 8/1993 | Meunier |
| 5,236,915 A | 8/1993 | Fiel |
| 5,248,603 A | 9/1993 | Marklund et al. |
| 5,262,532 A | 11/1993 | Tweedle et al. |
| 5,277,908 A | 1/1994 | Beckman et al. |
| 5,281,616 A | 1/1994 | Dixon et al. |
| 5,284,647 A | 2/1994 | Niedballa et al. |
| 5,366,729 A | 11/1994 | Marklund et al. |
| 5,403,834 A | 4/1995 | Malfroy-Camine et al. |
| 5,403,841 A | 4/1995 | Lang et al. |
| 5,405,369 A | 4/1995 | Selman et al. |
| 5,472,691 A | 12/1995 | Marklund et al. |
| 5,493,017 A | 2/1996 | Therien et al. |
| 5,563,132 A | 10/1996 | Bodaness |
| 5,599,924 A | 2/1997 | Therien et al. |
| 5,604,199 A | 2/1997 | Funanage |
| 5,610,293 A | 3/1997 | Riley et al. |
| 5,637,578 A | 6/1997 | Riley et al. |
| 5,674,467 A | 10/1997 | Maier et al. |
| 5,747,026 A | 5/1998 | Crapo |

(Continued)

FOREIGN PATENT DOCUMENTS

EP 127797 A1 12/1984

(Continued)

OTHER PUBLICATIONS

Archibald et al., Investigations of the State of the Manganese in *Lactobacillus plantarum*, Archives of Biochemistry and Biophysics 215(2):589-596 (1982).

Archibald et al., Manganese and Defenses against Oxygen Toxicity in *Lactobacillus plantarum*, Journal of Bacteriology 145(1):442-451 (1981).

Archibald et al., Manganese, Superoxide Dismutase, Oxygen Tolerance in Some Lactic Acid Bacteria, Journal of Bacteriology 146(3):928-936 (1981).

Archibald et al., The Scavenging of Superoxide Radical by Manganous Complex: In Vitro, Archives of Biochemistry and Biophysics 214(2):452-463 (1982).

(Continued)

*Primary Examiner* — Paul V. Ward

(74) *Attorney, Agent, or Firm* — Kilpatrick Townsend & Stockton LLP

(57) ABSTRACT

The present invention relates, in general, to a method of modulating physiological and pathological processes and, in particular, to a method of modulating cellular levels of oxidants and thereby processes in which such oxidants are a participant. The invention also relates to compounds and compositions suitable for use in such methods.

20 Claims, 7 Drawing Sheet

U.S. PATENT DOCUMENTS

| | | | |
|---|---|---|---|
| 5,767,272 A | 6/1998 | Wijesekera et al. |
| 5,834,509 A | 11/1998 | Malfroy-Camine et al. |
| 5,874,421 A | 2/1999 | Riley et al. |
| 5,948,771 A | 9/1999 | Danziger |
| 5,976,498 A | 11/1999 | Neumann et al. |
| 5,976,551 A | 11/1999 | Mottez et al. |
| 5,994,339 A | 11/1999 | Crapo et al. |
| 5,994,410 A | 11/1999 | Chiang et al. |
| 6,013,241 A | 1/2000 | Marchal et al. |
| 6,046,188 A | 4/2000 | Malfroy-Camine et al. |
| 6,060,467 A | 5/2000 | Buelow et al. |
| 6,084,093 A | 7/2000 | Riley et al. |
| 6,087,493 A | 7/2000 | Wheelhouse et al. |
| 6,103,714 A | 8/2000 | Fridovich et al. |
| 6,127,356 A | 10/2000 | Crapo et al. |
| 6,180,620 B1 | 1/2001 | Salvemini |
| 6,204,259 B1 | 3/2001 | Riley et al. |
| 6,214,817 B1 | 4/2001 | Riley et al. |
| 6,245,758 B1 | 6/2001 | Stern et al. |
| 6,372,727 B1 | 4/2002 | Crow et al. |
| 6,395,725 B1 | 5/2002 | Salvemini |
| 6,403,788 B1 | 6/2002 | Meunier et al. |
| 6,417,182 B1 | 7/2002 | Abrams et al. |
| 6,479,477 B1 | 11/2002 | Crapo et al. |
| 6,544,975 B1 | 4/2003 | Crapo et al. |
| 6,548,045 B2 | 4/2003 | Sakata et al. |
| 6,566,517 B2 | 5/2003 | Miura et al. |
| 6,573,258 B2 | 6/2003 | Bommer et al. |
| 6,583,132 B1 | 6/2003 | Crapo et al. |
| 6,602,998 B2 | 8/2003 | Kobuke et al. |
| 6,624,187 B1 | 9/2003 | Pandey et al. |
| 6,916,799 B2 | 7/2005 | Fridovich et al. |
| 7,189,707 B2 | 3/2007 | Crapo et al. |
| 7,470,677 B2 | 12/2008 | Crapo et al. |
| 2002/0042407 A1 | 4/2002 | Fridovich et al. |
| 2002/0058643 A1 | 5/2002 | Cherian et al. |
| 2007/0149498 A1 | 6/2007 | Crapo et al. |
| 2007/0197496 A1 | 8/2007 | Crapo et al. |

FOREIGN PATENT DOCUMENTS

| | | |
|---|---|---|
| EP | 186962 A1 | 7/1986 |
| EP | 282899 A2 | 9/1988 |
| EP | 0 284 645 A2 | 10/1988 |
| EP | 336879 A1 | 10/1989 |
| EP | 337601 A1 | 10/1989 |
| EP | 345171 A1 | 12/1989 |
| EP | 414915 A1 | 3/1991 |
| EP | 462836 A2 | 12/1991 |
| EP | 524161 A1 | 1/1993 |
| EP | 532327 A2 | 3/1993 |
| EP | 1616869 A1 | 1/2006 |
| FR | 2676738 A1 | 11/1992 |
| JP | 02-289844 | 11/1990 |
| JP | 3273082 | 12/1991 |
| WO | WO 91/04315 A1 | 4/1991 |
| WO | WO 91/19977 A1 | 12/1991 |
| WO | WO 92/07935 A1 | 5/1992 |
| WO | WO 92/08482 A1 | 5/1992 |
| WO | WO 92/15099 A1 | 9/1992 |
| WO | WO 93/02090 A1 | 2/1993 |
| WO | WO 94/04614 | 3/1994 |
| WO | WO 94/05285 A1 | 3/1994 |
| WO | WO 94/24116 | 10/1994 |
| WO | WO 95/10185 A1 | 4/1995 |
| WO | WO 95/31197 A1 | 11/1995 |
| WO | WO 96/09038 A2 | 3/1996 |
| WO | WO 96/09053 A1 | 3/1996 |
| WO | WO 96/40148 A1 | 12/1996 |
| WO | WO 96/40223 A1 | 12/1996 |
| WO | WO 97/06824 A2 | 2/1997 |
| WO | WO 97/06830 A1 | 2/1997 |
| WO | WO 97/06831 A1 | 2/1997 |
| WO | WO 97/33588 A1 | 9/1997 |
| WO | WO 97/33877 A1 | 9/1997 |
| WO | WO 98/33503 A1 | 8/1998 |
| WO | WO 98/58636 A1 | 12/1998 |
| WO | WO 99/07687 | 2/1999 |
| WO | WO 99/10317 | 3/1999 |
| WO | WO 99/23097 A1 | 5/1999 |
| WO | WO 99/55388 A1 | 11/1999 |
| WO | WO 00/04868 A2 | 2/2000 |
| WO | WO 00/19993 A2 | 4/2000 |
| WO | WO 00/23568 A2 | 4/2000 |
| WO | WO 00/43395 A1 | 7/2000 |
| WO | WO 00/72893 A2 | 12/2000 |
| WO | WO 00/75144 A2 | 12/2000 |
| WO | WO 01/26655 A1 | 4/2001 |
| WO | WO 01/96345 A1 | 12/2001 |
| WO | WO 02/04454 A1 | 1/2002 |
| WO | WO 02/096366 A2 | 12/2002 |

OTHER PUBLICATIONS

Balch, "Geometric and electronic structure and dioxygen sensitivity of the copper complex of octaethylbilindione, a biliverdin analog", J. Am. Chem. Soc. 115(25):12206-12207 (1993).

Balch, "Isolation and characterization of an iron biliverdin-type complex that is formed along with verdohemochrome during the coupled oxidation of iron (II) octaethylporphyrin", Am. Chem. Soc. 115(20):9056-9061 (1993).

Balch, "Solid-state self-association of the two-electron oxidation product of a biliverdin analogue", J. Chem. Soc. Chem. Commun. 6:643-644 (1995).

Bamford et al., "The Squalestatins: Synthesis and Biological Activity of Some C3-Modified Analogues; Replacement of a Carboxylic Acid or Methyl Ester with an Isoelectric Heterocyclic Functionality", J. Med. Chem. 38:3502-3513 (1995).

Batinic-Haberle et al, "Manganese(ill) meso-tetrakis(ortho-N-alkylpyridyl)porphyrins. Synthesis, characterization, and catalysis of 02.-dismutation", J. Chem. Soc. Dalton Trans., pp. 2689-2696 (2002).

Batinic-Haberle et al, Relationship among Redox Potentials, proton Dissociation Constants of Pyrrolic Nitrogens, and in Vivo and in Vitro Superoxide Dismutating Activities of Manganese(III) and Iron(III) Water-Soluble Porphyrins Inorg. Chem. 38:4011-4022 (1999).

Batinic-Haberle et al, "The Ortho Effect Makes Manganic Meso-Tetrakis-(N-Methylpyridinium-2-YL)(MnTM-2-PyPs+) A Powerful And Useful Superoxide Dismutase Mimic", Oxygen '97, The 4th Annual Meeting of The Oxygen Society, Council Meeting, The Palace Hotel, San Francisco, California, Nov. 20-24, 1997, —p. 38, Abstract 1-8.

Batinic-Haberle et al., "A Potent Superoxide Dismutase Mimic" Manganese[B]-Octabromo-meso-tetrakis (Nmethylpyridinium-4-yl)Porphyrin, Archives of Biochemistry and Biophysics 343(2):225-233 (1997).

Baudry et al., "Salen-Manganese Complexes are Superoxide Dismutase-Mimics", Biochemical and Biophysical Research Communication 192(2):964-968 (1993).

Beckman et al., "Apparent hydroxyl radical production by peroxynitrite: Implications for endothelial injury from nitric oxide and superoxide", Proc. Natl. Acad. Sci. USA 87:1620-1624 (1990).

Bedioui et al., "Metalloporphyrin-Polypyrrole Film Electrode: Characterization and Catalytic Application", J. Electroanal. Chem. 207:87-99 (1986).

Beil et al, "*Helicobacter pylon* Reduces Intracellular Glutathione in Gastric Epithelial Cells", Digestive Diseases and Sciences 45(9):1769-1773 (2000).

Berezin et al, Effect of ligand structure on the kinetic stability of tetraphenylporphyrin complexes of zinc and cadmium, Zhurnal Neorganicheskoi Khimii 25(10):2645-2652 (1980).

Berezin et l, "Factors determining the stability of complexes of copper with p-substituted derivatives of tetraphenylporphine", Zhurnal Fizicheskoi Khimil 53(11):2716-2719 (1979)—English Abstract.

Beyer, Jr., Characterization of a Superoxide Dismutase Mimic Prepared from Desferrioxamine and Mn02, Archives of Biochemistry and Biophysics 271(1):149-156 (1989).

Bishop et al., "The Reaction of Thiomides with Phosphorus Ylides", J. Org. Chem. 56:5079-5091 (1991).

Bloodsworth et al, "Manganese-Porphyrin Reactions with Lipids and Lipoproteins", Free Radical Biology & Medicine 28(7):1017-1029 (2000).

Bockhorst and Hoehn-Berlage, "An Optimized Synthesis of Manganese meso-Tetra(4-sulfonato phenyl) porphine: A Tumor-Selective MRI Contrast Agent", Tetrahedron 50(29):8657-8660 (1994).

Boissinot et al., "Rational Design and Expression of a Heparin-Targeted Human Superoxide Dismutase", Biochemical and Biophysical Research Communication 190(1):250-256 (1993).

Bors et al., "An expanded function for superoxide dismutase", Chemical Abstracts 115:388 (1991), Abstract No. 109185h.

Bottino, Rita et al., "Preservation of human islet cell functional mass by anti-oxidative action of a novel SOD mimic compound", Diabetes, 51:2561-7, Aug. 2002.

Brigelius et al., "Superoxide Dismutase Activity of Low Molecular Weight Cu2+-Chelates Studied by Pulse Radiolysis", FEBS Letters 47(1):72-75 (1974).

Burke, "Photochemical and thermal transformations of phytochrome", Chem. Physiol. Bile Pigm., Int. Symp., pp. 509-517 (1975).

Butje et al., "Electronic Spectra, Resonance Raman Spectra and Solution Properties of Water-soluble (Cu(II), Ni(II) and Co(III) Porphyrins", Inorg. Chim. Acta 167:97-108 (1990).

Callot and Schaeffer, "Ring contraction of homoporphyrins to porphyrins, meso-Reactivity of 5,10,15Triphenylporphin and Porphin", J. Chem. Research (S):51 (1978).

Chung et al, "Protective effects of heroin and tetrakis(4-benzoic acid)porphyrin on bacterial mutagenesis and mouse skin carcinogenesis induced by 7,12-dimethylbenz[a]anthracene", Mutation Research 472:139-145 (2000).

Clyde et al., "Distribution of Manganese Superoxide Dismutase mRNA in Normal and Hyperoxic Rat Lung", American Journal of Respiratory Cell and Molecular Biology 8:530-537 (1993).

Collman et al., "Synthesis of "Face to Face" Porphyrin Dimers Linked by 5,15-Substituents: Potential Binuclear Multielectron Redox Catalysts", J. Am. Chem. Soc. 103:516-533 (1981).

Comhair et al., "Rapid loss of superoxide dismutase activity during antigen-induced asthmatic response", Lancet 355 (9204):624 (2000).

Crapo and Tierney "Superoxide dismutase and pulmonary oxygen toxicity", Am. J. Physiol. 226:1401-1407 (1974).

Crapo et al., "Superoxide Dismutase and Oxygen Toxicity", Clinical Research, p. 222, 1991.

Crapo et al., "The Failure of Aerosolized Superoxide Dismutase to Modify Pulmonary Oxygen Toxicity", American Review of Respiratory Disease 115:1027-1033 (1977).

Crapo et al., 721195, Document No. 123:218443 (1994).

Darr et al., "A Mimic of Superoxide Dismutase Activity Based Upon Desferrioxamine B and Manganese(IV)", Archives of Biochemistry and Biophysics 258(2):351-355 (1987).

Datta-Gupta et al., "Synthetic Porphyrins II Preparation and Spectra of Some Metal Chelates of para", Journal of Substituted-mesa-TetraDhenylporphines, J. of Pharmaceutical Science 57(2):300-304 (1968).

Datta-Gupta et al., "Synthetic Porphyrins. I. Synthesis and Spectra of Some para-Substituted mesoTetraphenylporphines (1)", J. Heterocycl. Chem. 3:495-502 (1966).

Davila et al., "Sterically-Hindered Zinc Porphyrins for Solar-Energy Conversion", J. Chem. Soc., Chem. Commun., pp. 525-527 (1987).

Day et al., "A Metalloporphyrin Superoxide Dismutase Mimetic Protects Against Paraquat-Induced Endothelial Cell Injury, in Vitro", The Journal of Pharmacology and Experimental Therapeutics 275(3):1227-1232 (1995).

Day et al., "Manganic Porphyrins Possess Catalase Activity . . . ," Arch. Biochem. Biophys., vol. 347, No. 2, pp. 256-262 (1997).

De Peretti et al., "Imidazol[2,1-b]benzoxazole-3-acetamide derivatives, their preparation, and their therapeutic use", Chemical Abstracts 121:1016, Abstract No. 121:200896u, 1996.

Dealvare et al., "Mechanism of Superoxide Anion Scavenging Reaction by Bis-(Salicylato)-Copper(II) Complex", Biochemical and Biophysical Research Communications 69(3):687-694 (1976).

Deune et al., "Prevention of Ischemia-Reperfusion Injury with a Synthetic Metalloprotein Superoxide Dismutase Mimic, SC52608", Plastic and Reconstructive Surgery 98(4):711-718 (1996).

Diguiseppi et al., "Putative Superoxide Dismutase Activity of Iron-EDTA: A Reexamination", Archives of Biochemistry and Biophysics 203(1):145-150 (1980).

Dwyer et al., "Protective Properties of Tin- and Manganese-Centered Porphyrins Against Hydrogen PeroxideMediated Injury in Rat Astroglial Cells", J. Neurochem 71:2497 (1998).

Elangovan and Krishnan, "Photophysical properties of porphyrin amphiphiles bearing pyridinium alkyl groups", Chemical Physics Letters 194(1,2):139-146 (1992), XP000986304.

El-Far and Pimstone, "Selective in Vivo Tumor Localization of Uroporphyrin Isomer I in Mouse Mammary Carcinoma: Superiority over Other Porphyrins in a Comparative Study", Cancer Research 46:34390-4394 (1986).

Epp et al., "Superoxide Dismutase Activity of Manganese Chelates", 76-78 (1986).

Fajer et al., "Tr-Cation Radicals and Dications of Metalloporphyrins", Journal of the American Chemical Society 92 (11):3451-3459 (1970).

Falk, "Constribrutions to the chemistry of pyrrolic pigments", Tetrahedron 37(4):761-7 (1981).

Faulkner et al., "Characterization of Mn(III) Complexes of Linear and Cyclic Desferrioxamines as Mimics of Superoxide Dismutase Activity", Archives of Biochemistry and Biophysics 310(2):341-346 (1994).

Faulkner et al., Stable Mn(III) Porphyrins Mimic Superoxide Dismutase in Vitro and Substitute for It in Vivo, The Journal of Biological Chemistry 269(38):23471-23476 (1994).

Folz et al., "Extracellular Superoxide Dismutase (SODS): Tissue-Specific Expression, Genomic Characterization, and Computer-Assisted Sequence Analysis of the Human EC SOD Gene", Genomics 22:162-171 (1994).

Foran et al., "Effect of Electrolyte Concentration on Axial Anion Ligation in Manganese(III) mesa Tetraphenylporphyrin Chlorides", Inorg. Chem. 31:1463-1470 (1992).

Gassman et al., "Electronic Effects of Peripheral Substituents in Porphyrins: X-ray Photoelectron Spectroscopy and ab Initio Self-Consistent Field Calculations", J. Am. Chem. Soc. 114:9990-10000 (1992).

Gauuan et al, "Superoxide dismutase mimetics: synthesis and structure-activity relationship study of MnTBAP analogues", Bioorganic & Medicinal Chemistry 10(9):3013-3021 (2002).

Ghosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691-4699 (1995).

Giraudeau et al., "Substituent Effects in the Electroreduction of Porphyrins and Metalloporphyrins", Journal of the American Chemical Society 101(14):3857-3862 (1979).

Gonzalez et al., "EUK-8, a Synthetic Superoxide Dismutase and Catalase Mimetic, Ameliorates Acute Lung Injury in Endotexemic Swine", The Journal of Pharmacology and Experimental Therapeutics 275(2):798-806 (1995).

Groves and Marla, "Peroxynitrite-Induced DNA Strand Scission Mediated by a Manganese Porphyrin", J. Am. Chem. Soc. 117(37):9578-9579 (1995).

Halliwell, Barry, "The Superoxide Dismutase Activity of Iron Complexes", FEBS Letters 56(1):34-38 (1975).

Hambright et al, "Synthesis and Characterization of New Isomeric Water-Soluble Porphyrins Tetra(2-Nmethylpyridyl)porphine and Tetra(3-N-methylpyridyl)porphine", Inorganic Chemistry 15(9):2314-2315 (1976).

Hambright et al., "An acid solvolysis kinetic study of manganese(II)-tetra(2-Nmethylpyridyl)porphine", J. Inorg. Chem. 39:1102-1103 (1977).

Hambright et al., "Manganese(III) porphyrin isomers: polarography and stannous ion reduction kinetics", Porphyrin Chem. Adv., editor: Longo, [Pap. Porphyrin Symp.], pp. 284-292, Meeting Date 1977.

Harriman et al., "Photochemistry of Manganese Porphyrins Part 2.—Photoreduction", pp. 1543-1552, 1998.

Harriman et al., "Photochemistry of Manganese Porphyrins", J. Chem. Soc. 275:1532-1542 (1979).

Hunt et al., "Amphiphilic peroxynitrite decomposition catalysts in liposomal assemblies", Chemistry & Biology 4(11):845-858 (1997).

Iian et al., "Superoxide Dismuting Activity of an Iron Porphyrin", Inorg. Nucl. Chem. Letters 17(3/4):93-96 (1981) Couple, J. Phys. Chem. 86:1842-1849 (1982).

Inoue et al., "Expression of a Hybrid Cu/Zn-type Superoxide . . . ," J. Bio. Chem., vol. 266, No. 25, pp. 16409-16414 (1991).
International Search Report and Written Opinion from corresponding Application No. PCT/US00/02062 dated May 19, 2000.
International Search Report for International Application No. PCT/JP00/08558 dated Mar. 6, 2001.
International Search Report for International Application No. PCT/US02/17144 dated Aug. 22, 2002.
Jin et al., "A new route to water soluble porphyrins: phosphonium and ammonium type cationic porphyrins and self-assembly", Chem. Commun., pp. 1939-1940 (1996).
Joester et al., "Superoxide Dismutase Activity of Cu2+-Amino Acid Chelates", FEBS Letters 25(1):25-28 (1972).
Kariya et al., "Superoxide Dismutase (SOD) Activity with Fe-chlorin e6-Na and Suppression of Malignant Tumor Growth in Rats", Cancer Biotheraphy 10(2):139-145 (1995).
Kaufmann et al., "Separation of the Rotational Isomers of Tetrakis(N-methyl-2-pyridiniumyl)porphyrin and Crystal Structure of a,a,a,R-(Tetrakis(N-methyl-2-pyridiniumyl)porphyrin)copper Hexacyanoferrate", Inorg. Chem. 34:5073-5079 (1995).
Keinan et al., "Catalytic Antibodies. Circular Dichroism and UV-Vis Studies of Antibody-Metalloporphyrin Interactions", Inorg. Chem. 31:5433-5438 (1992).
Kobayashi et al, "Oxidative Stress Relief for Cancer-Bearing Hosts by the Protein-Bound Polysaccharide of Coriolus versicolor QUEL with SOD Mimicking Activity", Cancer Biotherapy 9(1):55-62 (1994).
Koerner "Carbon monoxide production during the oxygenation of cobalt complexes of linear etrapyrroles", Inorg. Chem. 37(5):982-988 (1998).
Konorev et ai, "Cell-Permeable Superoxide Dismutase and Glutathione Peroxidase Mimetics Afford Superior Protection against Doxorubicin-Induced Cardiotoxicity: The Role of Reactive Oxygen and Nitrogen Intermediates", Archives of Biochemistry and Biophysics 368(2):421-428 (1999).
Kumar et al., "Radioprotection by Antioxidant Enzymes and Enzyme Mimetics", Pharmac. Ther. 39:301-309 (1988).
Landesmaki et al, "Detection of Oxygen Consumption of Cultured Adherent Cells by Bead Injection Spectroscopy", Analytical Chemistry 71(22):5248-5252 (1999).
Lapping "Part III Bioinorganic Studies", Inorganic Reaction Mechanisms 7:334-343 (1981).
Lee and Smith, "Syntheses of symmetrically substituted 5-alkyl- and 5-aryl-dihydrodipyrrins and of porphyrins and bisporphyrins therefrom", J. Chem. Soc. Perkin Trans 1:1215-1227 (1997).
Lee et al., "Rapid decomposition of peroxynitrite by manganese porphyrin-antioxidant redox couples", Bioorganic & Medical Chemistry Letters 7(22):2913-2918 (1997).
Leonidas et al., "5,10,15,20-Tetrakis( , , , - -(N-tert-butyl-carbamoyl)phenyl)porphyrin: Syntheses and Redox Properties of Zinc(II) and Copper(II) Complexes", J. Org. Chem. 54:6135-6138 (1989).
Libby et al., "Cationic Porphyrin Derivatives As Inhibitors of Polyamine Catabolism", Biochemical Pharmacology 50 (9):1527-1530 (1995).
Lindsey et al, "Rothemund and Adler-Longo Reactions Revisited: Synthesis of Tetraphenylphorins under Equilibrium Conditions", J. Org. Chem. 52:827-836 (1987).
Lindsey et al, "Synthesis of tetraphenylporphyrins under very mild conditions", Tetrahedron Letters 27(41):4969-4970 (1986).
Lindsey et al, $^{252}$Cf Plasma Desorption Mass Spectrometry in the Synthesis of Porphyrin Model Systems, Anal. Chem. 64(22):2804-2814 (1992).
Liochev et al., A Cationic Manganic Porphyrin Inhibits Uptake of Paraquat by Escherichia coil, Archives of Biochemistry and Biophysics 321(1):271-275 (1995).
Longo et al., "The Synthesis and Som e Physical Properties of ms-Tetra(pentafluorophenyl)-porphin and msTetraphenylporphines (1)", Notes 6:927-931 (1969).
Lord, "Redox characteristics of nickel and palladium complexes of the open-chain tetrapyrrole octaethylbilindione: a biliverdin model", Inorg. Chem. 39(6):1128-34 (2000).

Louati et al., "Homophophyrines: Effets D'Une Coupure De Conjugaison Cyclique Sur La Reactivite Redox Des Porphyrines", Nouv. J. Chim. 2:163-168 (1978).
Lowe et al., "Comparison of the cardiovascular effects of two novel superoxide dismutase mimetics, SC-55858 and SC-54417, in conscious dogs", European Journal of Pharmacoloty 304:81-86 (1996).
Mabley et al, "Part II: Beneficial Effects of the Peroxynitrite Decomposition Catalyst FP15 in Murine Models of Arthritis and Colitis", Molecular Medicine 8(10):581-590 (2002).
Mackensen et al., "Neuroprotection from Delayed Postischemic Administration of a Metalloporphyrin Catalytic Antioxidant", The Journal of Neuroscience 21(13):4582-4592 (2001).
Madakyan et al., "New watersoluble metal complexes of meso-tetrakis[3-N-(2'-hydroxy ethyl)pyridyl]porphyrins and their pharmacological activity", Arm., Khim. Zh. 42(11):724-728—Chemical Abstracts 113:653—Abstract No. 114907h, 1972.
Madakyan et al., "Some metal complexes of meso-tetrakis (3-N-substituted pyridyl) porphyrins and their bioactivity", Arm. Khim. Zh. 42(10):642-646 (1989).
Malinski et al., "Characterization of Conductive Polymeric Nickel(II) Tetrakis(3-methoxy-4-hydroxyphenyl)Porphyrin as an Anodic Material for Electrocatalysis", J. Electrochem. Soc. 138(7):2008-2015 (1991).
Marx, "Role of Gene Defect in Heredity ALS Clarified", Science 261:986 (1993).
McClune et al., "Catalysis of Superoxide Dismutation by Iron-Ethylenediaminetetraacetic Acid Complexes. Mechanism of the Reaction and Evidence for the Direct Formation of an Iron(III)-Ethylenediaminetetraacetic Acid Peroxo Complex from the Reaction of Superoxide with Iron(II)-Ethylenediaminetetraacetic Acid", Communications to the Editor, p. 5220-2 (1977).
McCord et al., "Superoxide Dismutase—An Enzymic Function for Erythrocuprein", Biochemistry 492, p. 346.
McCord et al., Superoxide Dismutase An Enzymic Function for Erythrocuprein (Hemocuprein), The Journal of Biological Chemistry 244(22):6049-6055 (1969).
Milgrom et al., "Redox Behaviour of Phenolic Porphyrins in Basic Solutions: A Reappraisal", Free Rad. Res. 24 (1):19-29 (1996).
Milgrom, Facile Aerial Oxidation of a Porphyrin. Part 3. "Some Metal Complexes of meso-Tetrakis-(3,5-di-tbutyl-4-hydroxyphenyl)porphyrin", J. Chem. Soc. Perkin Trans. 11:71-79 (1988).
Moisy et al., "Catalytic Oxidation of 2,6-Di-Terbutylphenol by Molecular Oxygen Electroassisted by Poly(Pyrrole Manganese-Porphyrin)", New J. Chem. 13:511-514 (1989).
Naruta et al., "High Oxygen-Evolving Activity of Rigidly Linked Manganese (III) Porphyrin Dimers. A Functional Model of Manganese Catalase", J. Am. Chem. Soc. 113:3595-3596 (1991).
Oberley et al., "Anticancer activity of metal compounds with superoxide dismutase activity", Agents and Actions 15 (5/6):535-538 (1984).
Obst et al, "*Helicobacter pylori* causes DNA damage in gastric epithelial cells", Carcinogenesis 21(6):1111-1115 (2000).
Office Action dated Sep. 4, 2009 in U.S. Appl. No. 11/857,949, 10 pages.
O'Hara et al., "Potentiation of radiation-induced cell kill by synthetic metalloporphyrins", Int. J. Radiat. Oncol. Biol. Phys. 16(4):1049-1052 (1989).
Ohkawa et al., "Assay for Lipid Peroxides in Animal Tissues by Thiobarbituric Acid Reaction", Analytical Biochemistry 95:351 (1979).
Oury et al., "Cold-induced Brain Edema in Mice", The Journal of Biological Chemistry 268(21):15394-15398 (1993).
Oury et al., "Establishment of Transgenic Mice Expressing Human Extracellular Superoxide Dismutase", American Review of Respiratory Disease 143(4):A515 (1991), International Conference Supplement Abstracts—No. 236.
Oury et al., "Immunocytochemical Localization of Extracellular Superoxide Dismutase in Human Lung", American Revew of Respiratory Disease 147(4):A713 (1993), International Conference Supplement Abstracts—No. 246.
Oury et al., "Transgenic Mice Superexpressing Human Extracellular Superoxide Dismutase Show Increased Resistance to Cold-induced Brain Edema, But are More Susceptible to Hyperbaric Oxygen", American Review of Respiratory Disease 145(4):A713, 1987.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the, 1994.

Oury. et al., "Extracellular superoxide dismutase, nitric oxide, and central nervous system 02 toxicity", Proc. Natl. Acad. Sci. USA 89:9715-9719 (1992).

Parge et al., "Atomic structures of wild-type and thermostable mutant recombinant human Cu,Zn superoxide dismutase", Proc. Natl. Acad. Sci. USA 89:6109-6113 (1992).

Pasternack et al., "Aggregation of Nickel(II), Copper (II), and Zinc(II) Derivatives of Water-Soluble Porphyrins", Inorganic Chemistry 12(11):2606-2610 (1973).

Pasternack et al., "Catalyst of the Disproportionation of Superoxide by Metalloporphyrins III", Journal of Inorganic Biochemistry 15:261-267 (1981).

Pasternack et al., "Catalyst of the Disproportionation of Superoxide by Metalloporphyrins", Journal of Inorganic Biochemistry 11:261-267 (1979).

Pasternack et al., "On the Aggregation of Meso-Substituted Water-Soluble Porphyrins", Journal of American Chemical Society 94(13):4511-4517 (1972).

Pasternack et al., "Superoxide Dismutase Activities of an Iron Porphyrin and Other Iron Complexes", Journal of the American Chemical Society 101(4):1026-1031 (1979).

Patel and Day, "Metalloporphyrin class of therapeutic catalytic antioxidants", Tips Elsevier Trends Journal 20(9):359-364(1999).

Patel et al., "Requirement for Superoxide in Excitotoxic Cell Death", Neuron 16:345-355 (1996).

Peretz et al., "Chemical properties of water-soluble porphyrins 3. The reaction of superoxide radicals with some metalloporphyrins", Int. J. Radiat. Biol. 42(4):449-456 (1982).

Picker et al., "Cobalt(III) complexes of water soluble synthetic meso-substituted porphyrins as radiation sensitizers for oxic and hypoxic tumor cells", 8-Radiation 112:405 (1990) Abstract No. 112:73026d.

Pitie et al., "Oxidation at Carbon-1' of DNA Deoxyriboses by the Mn-TMPyP/KHSO5 System Results from a Cytochrome P-450-Type Hydroxylation Reaction", J. Am. Chem. Soc. 117:2935-2936 (1995).

Poison et al, "The Effect of Liver Transplantation in a 13-Year-Old Boy with Erythropoietic Protoporphyria", Transplantation 46(3):386-389 (1988).

Registry Copyright 2004 ACS on STN, Registry No. 138025-71-5, Entered STN: Dec. 21, 1991.

Richards et al, "Observation of a Stable Water-Soluble Lithium Porphyrin", Inorg. Chem. 35:1940-1944 (1996).

Robertson, Jr. et al, "Does Copper-D-Penicillamine Catalyze the Disutatio of O2-?", Archives of Biochemistry and Biophysics 203(2) 830-831 (1980).

Rosenfeld et al., "Safety and pharmacokinetics of recombinant human superoxide dismutase administered intratracheally to premature neonates with respiratory distress syndrome", Pediatrics 97(Pt 1):811-817 (1996).

Ruoslahti et al., "Arg-Gly-Asp: A Versatile Cell Recognition Signal", Cell 44:517-518 (1986).

Sari et al., "Interaction of Cationic Porphyrins with DNA: Importance of the Number and Position of the Charges and Minimum Structural Requirements for Intercalation", Biochemistry 29:4205-4215 (1990).

Schlozer et al., "Reactivity of Unsubstituted Porphin", German version: Angew. Chem. 87:388 (1975).

Schneider et al., "Ligand-Porphyrin Complexes: Quantitative Evaluation of Stacking and Ionic Contributions", J. Org. Chem. 59:7464-7472 (1994).

Sharma et al., "Synthesis of amphiphilic 5-(4-N-alkylpyridiniumyl)-10,15,20-triphenylporphyrins and their aggregational properties in different solvent systems", Chemical Abstracts vol. 123, No. 1 (1995)—Abstract No. 9222q.

Sheldon, Chapter 1 in Metalloporphyrins in Catalytic Oxidations, Marcel Dekker, Inc. (1994).

Shimanovich et ai, "Mn(II)-Texaphyrin as a Catalyst for the Decomposition of Peroxynitrite", J. Am. Chem. Soc. 123:3613-3614 (2001).

Solomon et al., "Chemical properties of Water-Soluble Porphyrins. 2. The Reaction of Iron(III) Tetrakis(4 Nmethylpyridyl)porphyrin with the Superoxide Radical Dioxygen Couple", J. Phys. Chem. 86:1842-1849 (1982).

Song et al., "Anti-HIV activities of anionic metalloporphyrins and related compounds", Antiviral Chemistry and Chemotherapy 8(2):85 (1997).

Sonis et al, "AEOL 10150, a catalytic antioxidant, reduces the incidence and duration of radiation-induced oral mucositis in a hamster", European Journal of Cancer 37:S361 (2001)—Abstract.

Sorenson, John R.J., "Copper Chelates as Possible Active Forms of the Antiarthritic Agents", Journal of Medicinal Chemistry 19(1):135-148 (1976).

Spasojevic et al., "Manganese(III) complexes with porphyrins and related compounds as catalytic scavengers of superoxide", Inorganica Chimica Acta 317:230-242 (2001).

Stralin et al., "Effects of Oxidative Stress on Expression of Extracellular Superoxide Dismutase, CuZnSuperoxide Fibroblast", Biochem. J. 298:347-352 (1994).

Supplementary European Search Report for EP02739551 dated Aug. 5, 2009, 4 pages.

Szabo et ai, "Part I: Pathogenetic role of Peroxynitrite in the Development of Diabetes and Diabetic Vascular Complications: Studies With FP15, A Novel Potent Peroxynitrite Decomposition Catalyst" Molecular Medicine 8(10):571-580 (2002).

Szabo et al., "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", 1999.

Szabo et al., "Peroxynitrite Is Involved in the Pathogenesis of the Vascular Contractile and Energetic Failure in Endotoxic Shock", Shock Society Meeting (1996).

Tjahjono et al., "Cationic porphyrins . . . ", biochmica et Biophysica Acta 1472 (1999) 333-343. Note: Closest prior art.

Tsan, M-F., "Superoxide Dismutase and Pulmonary Oxygen Toxicity, " XP-002074505, pp. 286-290, 1994.

Tsvetkov et al, "Infrared spectra of copper complexes of tetraphenylporphyrin", Izvestiya Vrvysshikh Uchebnykh Zavedenij, Khimiya I Khimicheskaya Tekhnologiya 27(7):782-785 (1984)—English Abstract, 1 page.

Vergeldt et al., "Intramolecular Interactions in the Ground and Excited State of Tetrakis(N-methylpyridyi) porphyrins", J. Phys, Chem. 99:4397-4405 (1995).

Vinogradov and Wilson, "Palladium catalyzed carbonylation of Br-substituted porphyrins", Tetrahedron Letters 39(49):8935-8938 (1998).

Vodzinskii et al., "Porphyrines and Their derivatives. XX. Synthesis and properties of 2-Nitro-5,10,15,20 tetraheterylporphyrins", Russian Journal of Organic Chemistry 34(6):882-885 (1998).

Walker et al, "Models of the cytochromes b, 5. EPR Studies of low-spin iron(III) tetraphenylporphyrins", Journal of the American Chemical Society 106(23):6888-6898 1984).

Wang et al, Structure of LB film of 5,10,15,20-tetra(p-ethoyycarbonphenyl)porphyrin, Yingyong Huaxue 10(21:87-88 (1993)—English Abstract.

Weinraub et al., "Chemical Properties of Water-Soluble Porphyrins. 1. Equilibria between Some Ligands and Iron (III) Tetrakis (4-N-methylpyridyl)porphyrin", J. Phys. Chem. 86:1839-1842 (1982).

Weinraub et al., "Chemical properties of water-soluble porphyrins. 5. Reactions of some manganese (III) porphyrins with the superoxide and other reducing radicals", Int. J. Radiat. Biol. 50(4):649-658 (1986) (Abs).

Weiss et al., "Evaluation of Activity of Putative Superoxide Dismutase Mimics", The Journal of Biological Chemistry 268(31):23049-23054 (1993).

Weiss et al., "Manganese-based Superoxide Dismutase Mimetics Inhibit Neutral Infiltration in Vivo", The Journal of Biological Chemistry 271(42):26149-26156 (1996).

Werringloer et al., "The Interaction of Divalent Copper and the Microsomal Electron Transport System", The Journal of Biological Chemistry, 254(23):11839-11846 (1979).

Wheelhouse et al., "Cationic Porphyrins as Telomerase Inhibitors; the Interaction of Tetra-(N-methyl-4pyridyl) porphine with Quadruplex DNA", J. Am. Chem. Soc. 120(13):3261-3262 (1998).

White et al, "A Highly Stereoselective Synthesis of Epothilone B", J. Org. Chem. 64:684-685 (1999).

Winkelman, James, "The Distribution of Tetraphenylporphinesulfonate in the Tumor-bearing Rat", Cancer Research 22:589-596 (1962).

Wolberg et al., "Electrocical and electron paramagnetic resonance studies of metalloporphyrins and their electrochemical oxidation products", Journal of the American 92(10):2982-90 (1970).

Yu and Su, "Electrocatalytic reduction of nitric oxide by water-soluble manganese porphyrins", Journal of Electroanalytical Chemistry 368:323-327 (1994).

Yue et al., "Carvedilol, a New Vasodilator and Beta Adrenoceptor Antagonist, is an Antioxidant and Free Radical Scavenger", The Journal of Pharmacology and Experimental Therapeutics 263:(1992).

Zahedi, "Semiempirical molecular orbital calculations of biliverdin: study of dynamics and energetics of the self association of a two-electron oxidation product", Theochem. 531:79-88 (2000).

Aeol-10118

Aeol-10119

| SOD | 13 | interferes |
|---|---|---|
| CAT | 0.16 | 0.14 |
| TBARS | 20 | 27 |

Aeol-10121

Aeol-10122

| SOD | 164 | 19 |
|---|---|---|
| CAT | 0.32 | 0.3 |
| TBARS | 2 | 4 |

| SOD | 16,600 | 5 |
| CAT | 2.56 | 0.44 |
| TBARS | 2 | 3 |

| SOD | interferes | interferes |
| CAT | 0.04 | 0.1 |
| TBARS | 16 | 10 |

| SOD | interferes | 3 |
| --- | --- | --- |
| CAT | 0.04 | 0.16 |
| TBARS | 1 | 2 |

| SOD | interferes | 31 |
| --- | --- | --- |
| CAT | 2.6 | 2.1 |
| TBARS | 4 | 2 |

| SOD | interferes | 16 |
|---|---|---|
| CAT | 1.3 | 0.02 |
| TBARS | 2 | 2 |

| SOD | 1900 | 56 |
|---|---|---|
| CAT | 1.8 | 0.23 |
| TBARS | 13 | 2 |

| SOD | interferes | 77 |
| CAT | 0.76 | 1.46 |
| TBARS | 21 | 77 |

| SOD | interferes | 13,400 |
| CAT | NOT DONE | NOT DONE |
| TBARS | NOT DONE | NOT DONE |

| SOD | 16 | 121 |
|---|---|---|
| CAT | NOT DONE | NOT DONE |
| TBARS | NOT DONE | NOT DONE |

| SOD | 13,887 | 6,260 |
|---|---|---|
| CAT | NOT DONE | NOT DONE |
| TBARS | NOT DONE | NOT DONE |

SUBSTITUTED PORPHYRINS

CROSS-REFERENCES TO RELATED APPLICATIONS

This application is a continuation of U.S. patent application Ser. No. 11/424,662, filed Jun. 16, 2006, which in turn is a divisional of U.S. patent application Ser. No. 10/349,171, filed Jan. 23, 2003, now issued as U.S. Pat. No. 7,189,707, which in turn is a continuation of U.S. patent application Ser. No. 09/490,537, filed Jan. 25, 2000, now issued as U.S. Pat. No. 6,544,975, all of which claim the benefit of U.S. Provisional Patent Application No. 60/117,010, filed Jan. 25, 1999, and each of which is incorporated herein in its entirety and for all purposes.

STATEMENT AS TO RIGHTS TO INVENTIONS MADE UNDER FEDERALLY SPONSORED RESEARCH OR DEVELOPMENT

This invention was made with Government support under Grant Nos. HL31992 and HL63397 award by the National Institutes of Health. The Government has certain rights in the invention.

TECHNICAL FIELD

The present invention relates, in general, to a method of modulating physiological and pathological processes and, in particular, to a method of modulating cellular levels of oxidants and thereby processes in which such oxidants are a participant. The invention also relates to compounds and compositions suitable for use in such methods.

BACKGROUND

Oxidants are produced as part of the normal metabolism of all cells but also are an important component of the pathogenesis of many disease processes. Reactive oxygen species, for example, are critical elements of the pathogenesis of diseases of the lung, the cardiovascular system, the gastrointestinal system, the central nervous system and skeletal muscle. Oxygen free radicals also play a role in modulating the effects of nitric oxide (NO.). In this context, they contribute to the pathogenesis of vascular disorders, inflammatory diseases and the aging process.

A critical balance of defensive enzymes against oxidants is required to maintain normal cell and organ function. Superoxide dismutases (SODs) are a family of metalloenzymes that catalyze the intra- and extracellular conversion of $O_2^-$ into $H_2O_2$ plus $O_2$, and represent the first line of defense against the detrimental effects of superoxide radicals. Mammals produce three distinct SODs. One is a dimeric copper- and zinc-containing enzyme (CuZn SOD) found in the cytosol of all cells. A second is a tetrameric manganese-containing SOD (Mn SOD) found within mitochondria, and the third is a tetrameric, glycosylated, copper- and zinc-containing enzyme (EC-SOD) found in the extracellular fluids and bound to the extracellular matrix. Several other important antioxidant enzymes are known to exist within cells, including catalase and glutathione peroxidase. While extracellular fluids and the extracellular matrix contain only small amounts of these enzymes, other extracellular antioxidants are also known to be present, including radical scavengers and inhibitors of lipid peroxidation, such as ascorbic acid, uric acid, and α-tocopherol (Halliwell et al., Arch. Biochem. Biophys. 280:1 (1990)).

The present invention relates generally to low molecular weight porphyrin compounds suitable for use in modulating intra- and extracellular processes in which superoxide radicals, or other oxidants such as hydrogen peroxide or peroxynitrite, are a participant. The compounds and methods of the invention find application in various physiologic and pathologic processes in which oxidative stress plays a role.

SUMMARY OF THE INVENTION

The present invention relates to a method of modulating intra- or extracellular levels of oxidants such as superoxide radicals, hydrogen peroxide, peroxynitrite, lipid peroxides, hydroxyl radicals and thiyl radicals. More particularly, the invention relates to a method of modulating normal or pathological processes involving superoxide radicals, hydrogen peroxide, nitric oxide or peroxynitrite using low molecular weight antioxidants, and to methine (i.e., meso) substituted porphyrins suitable for use in such a method.

Objects and advantages of the present invention will be clear from the description that follows.

Homogenates

Figure 1A:
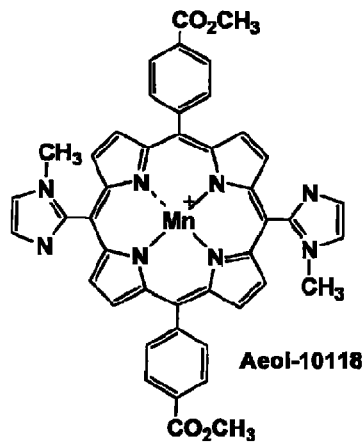
FIGS. 1A-1F show the structures of certain compounds of the invention. The SOD activity values were determined using the method of McCord and Fridovich, J. Biol. Chem. 244:6049 (1969). The catalase values were determined using the method of Day et al., Arch. Biochem. Biophys. 347:256 (1997). The TBARS values were obtained as follows.
Figure 1A:
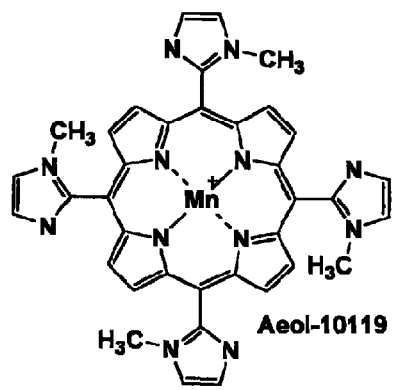
Figure 1A:
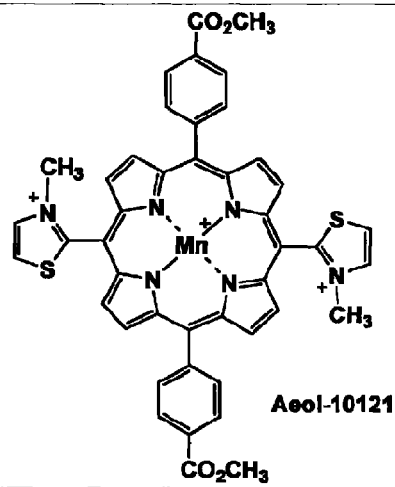
Figure 1A:
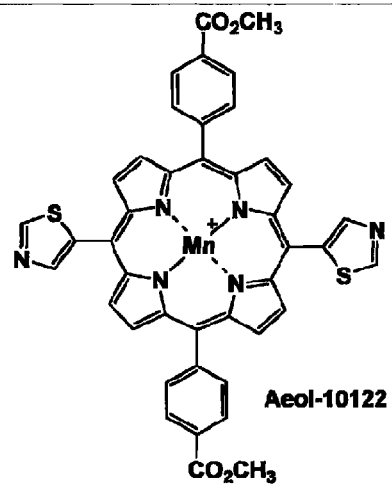
Figure 1B:
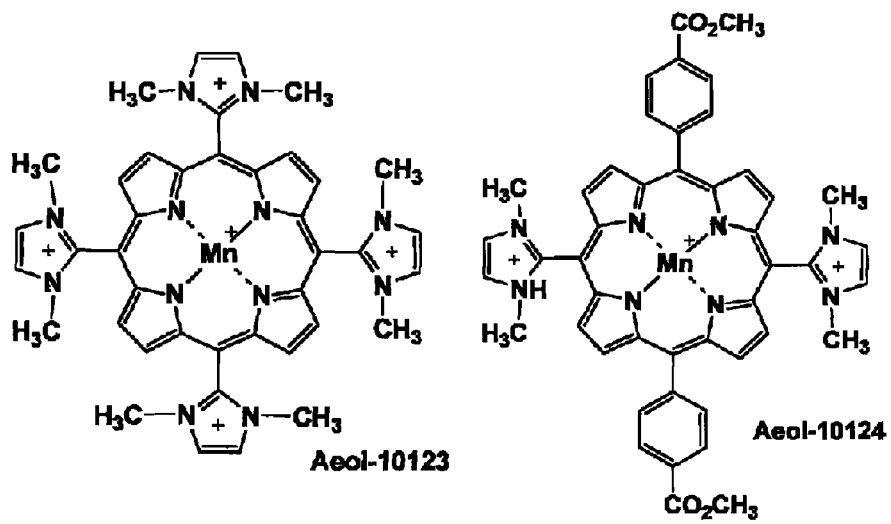
Figure 1B:
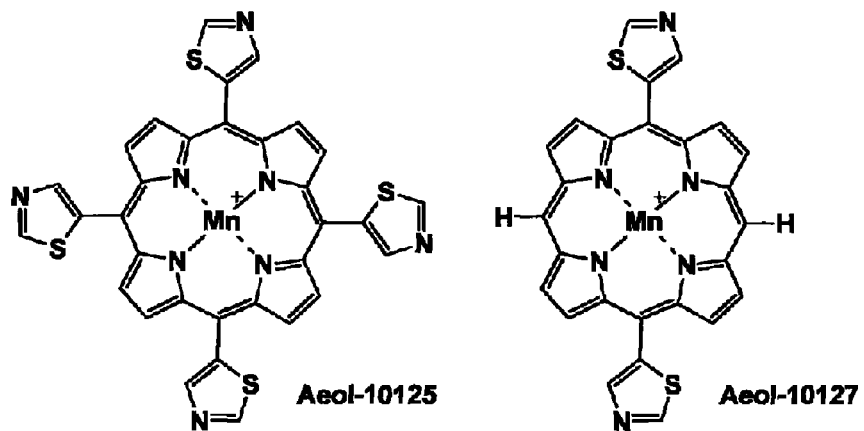
Figure 1C:
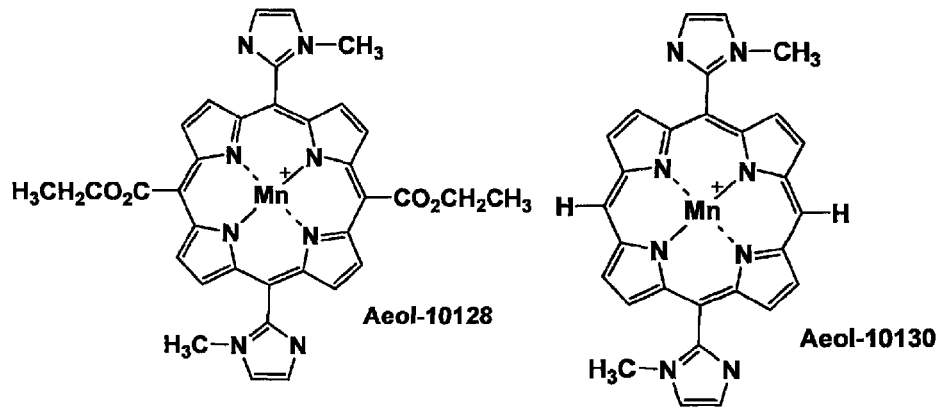
Figure 1C:
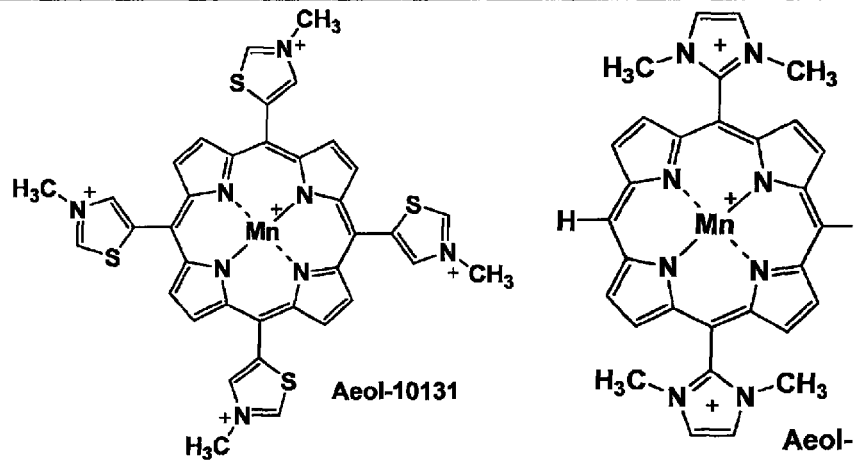
Figure 1D:
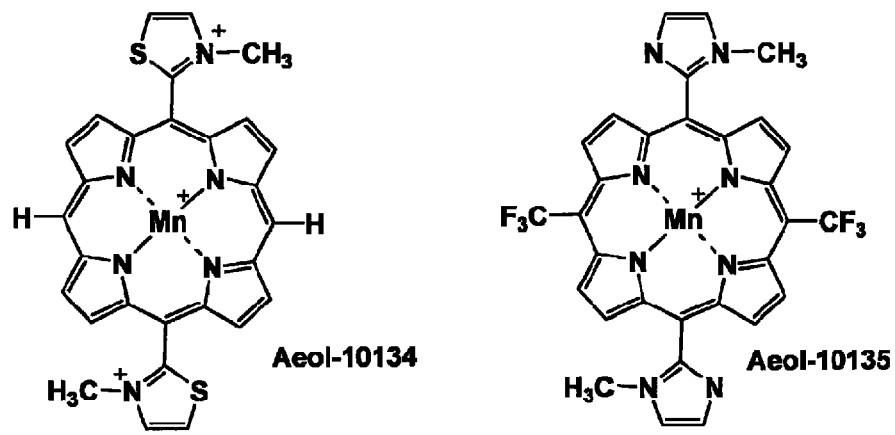
Figure 1D:
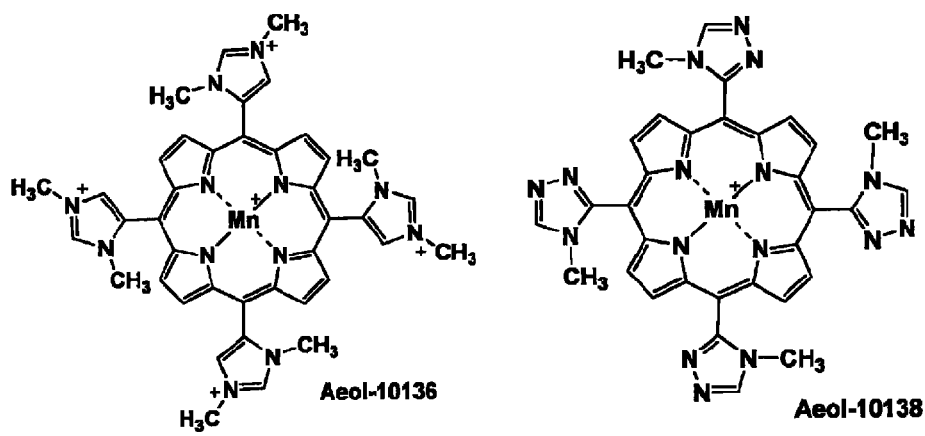
Figure 1E:
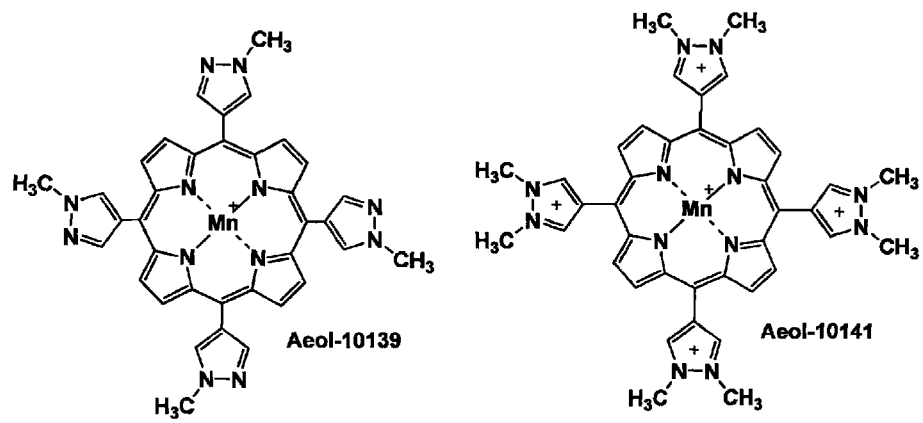
Figure 1E:
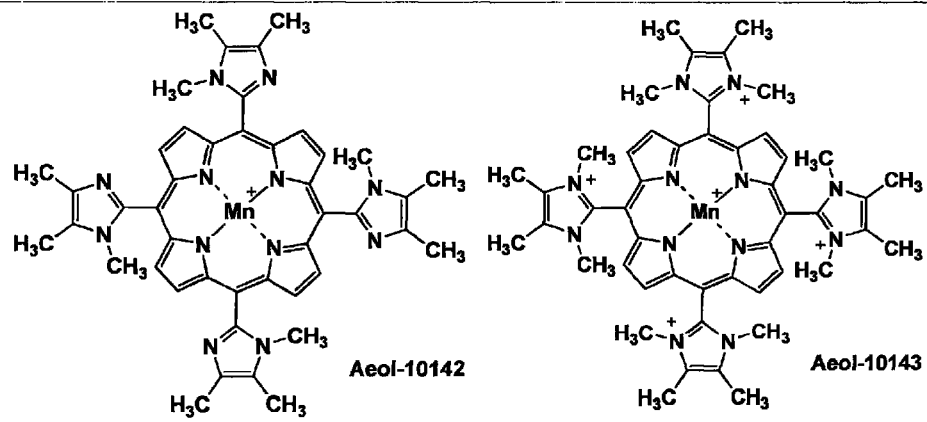
Figure 1F:
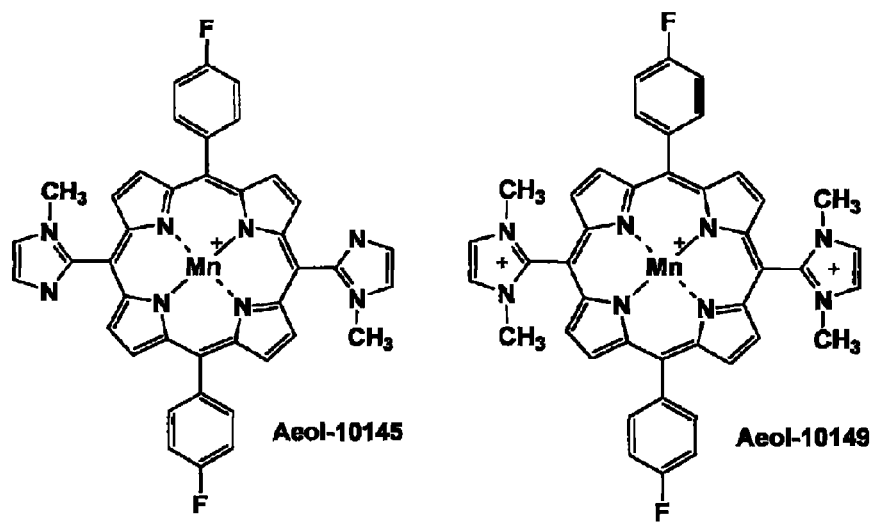
Figure 1F:
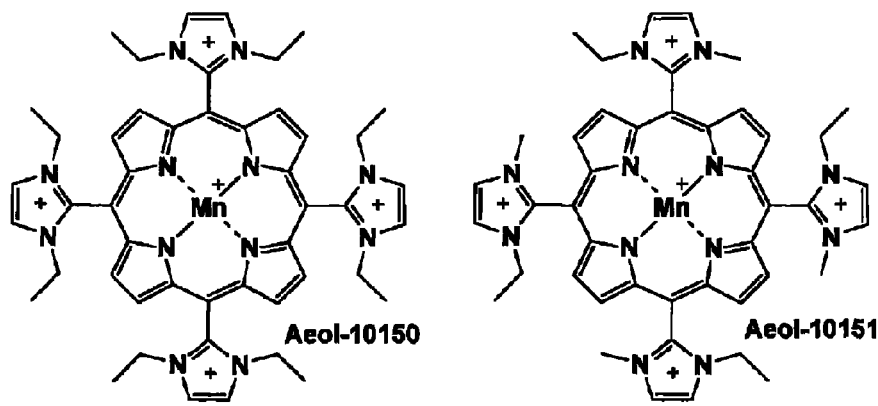

Frozen adult Sprague-Dawley rat brains, livers and mouse lungs (Pel-Freez, Rogers, Ark.) were homogenized with a polytron (Turrax T25, Germany) in 5 volumes of ice cold 50 mM potassium phosphate at pH 7.4. Homogenate protein concentration was determined with the Coomassie Plus protein assay (Pierce, Rockford, Ill.) using bovine serum albumin as a standard. The homogenate volume was adjusted with buffer to give a final protein concentration of 10 mg/ml and frozen as aliquots at −80° C.

Oxidation of Homogenates

Microfuge tubes (1.5 ml) containing 0.2 ml of homogenate (0.2 mg protein) and various concentrations of antioxidant were incubated at 37° C. for 15 minutes. Oxidation of the rat brain homogenate was initiated by the addition of 0.1 ml of a freshly prepared stock anaerobic solution containing ferrous chloride (0.25 mM) and ascorbate (1 mM). Samples were placed in a shaking water bath at 37° C. for 30 minutes (final volume 1 ml). The reactions were stopped by the addition of 0.1 μL of a stock butylated hydroxytoluene (60 mM) solution in ethanol.

Lipid Peroxidation Measurement

The concentration of thiobarbituric acid reactive species (TBARS) in rat brain homogenates was used as an index of lipid peroxidation. Malondialdehyde standards were obtained by adding 8.2 μL of 1,1,3,3-tetramethoxypropane in 10 ml of 0.01 N HCl and mixing for 10 minutes at room temperature. This stock was further diluted in water to give standards that ranged from 0.25 to 25 μM. Samples or standards (200 μL) were acidified with 200 μL of 0.2 M stock of phosphoric acid in 1.5 ml locking microfuge tubes. The color reaction was initiated by the addition of 25 μL of a stock thiobarbituric acid solution (0.11M) that was mixed and then placed in a 90° C. heating block for 30 minutes. TBARS were extracted with 0.5 ml of n-butanol by vortexing for 3 minutes and chilling on ice for 1 minute. The samples were then centrifuged at 12,000×g for 3 minutes and a 150 μl aliquot of the n-butanol phase was placed in each well of a 96-well plate and read at 535 nm in a Thermomax platereader (Molecular Devices, Sunnydale, Calif.) at 25° C. Sample absorbances were converted to MDA equivalences (μM) by extrapolation from the MDA standard curve. None of the antioxidants at concentrations employed in these studies affected the reaction of MDA standards with thiobarbituric acid.

Statistical Analyses

Data were presented as their means±SE. The inhibitory concentration of antioxidants that decreased the degree of lipid peroxidation by 50% ($IC_{50}$) and respective 95% confidence intervals (CI) were determined by fitting a sigmoidal curve with variable slope to the data (Prizm, GraphPad, San Diego, Calif.). (See also Braughler et al., J. Biol. Chem. 262:10438 (1987); Kikugawa et al., Anal. Biochem. 202:249 (1992).)

Figure 2:
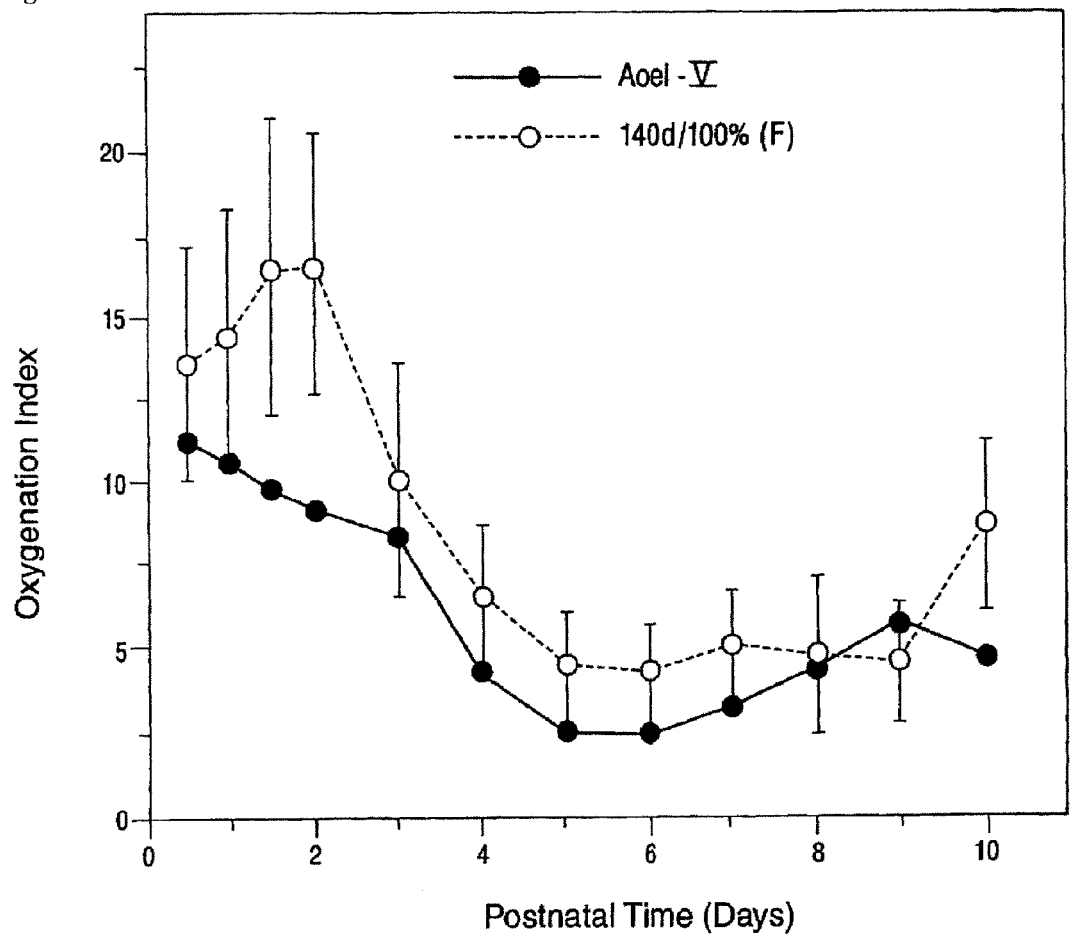

FIG. 2 shows the data obtained from a study involving treatment of bronchopulmonary dysplasia using Aeol-V.

DETAILED DESCRIPTION OF THE INVENTION

The present invention relates to methods of protecting against the deleterious effects of oxidants, particularly, superoxide radicals, hydrogen peroxide and peroxynitrite, and to methods of preventing and treating diseases and disorders that involve or result from oxidant stress. The invention also relates methods of modulating biological processes involving oxidants, including superoxide radicals, hydrogen peroxide, nitric oxide and peroxynitrite. The invention further relates to compounds and compositions, including low molecular weight antioxidants (e.g., mimetics of scavengers of reactive oxygen species, including mimetics of SODs, catalases and peroxidases) and formulations thereof, suitable for use in such methods.

Mimetics of scavengers of reactive oxygen species appropriate for use in the present methods include methine (i.e., meso) substituted porphines, or pharmaceutically acceptable salts thereof (e.g., chloride or bromide salts). The invention includes both metal-free and metal-bound porphines. In the case of metal-bound porphines, manganic derivatives of methine (meso) substituted porphines are preferred, however, metals other than manganese such as iron (II or III), copper (I or II), cobalt (II or III), or nickel (I or II), can also be used. It will be appreciated that the metal selected can have various valence states, for example, manganese II, III or V can be used. Zinc (II) can also be used even though it does not undergo a valence change and therefore will not directly scavenge superoxide. The choice of the metal can affect selectivity of the oxygen species that is scavenged. Iron-bound porphines, for example, can be used to scavenge NO. while manganese-bound porphines scavenge NO. less well.

The mimetics of the present invention are of the Formula I:

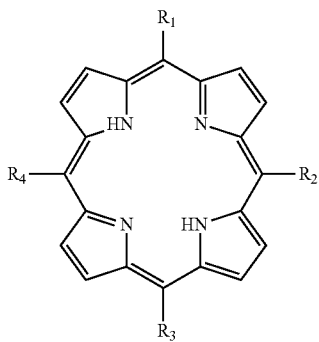

or pharmaceutically acceptable salt thereof wherein:

$R_1$ and $R_3$ are the same and are:

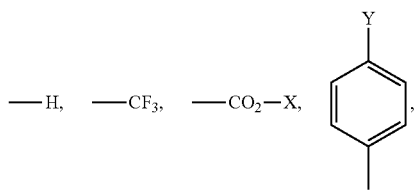

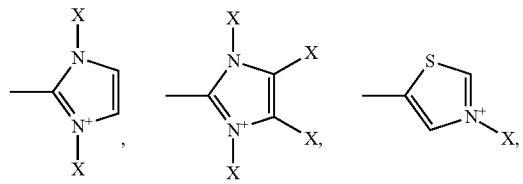

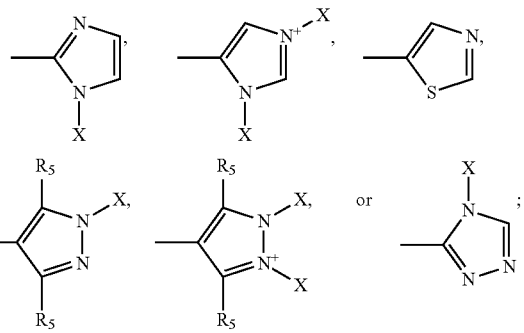

$R_2$ and $R_4$ are the same and are:

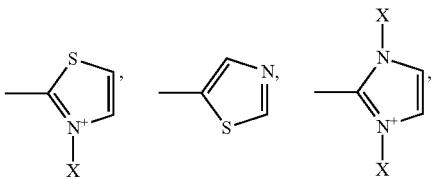

-continued

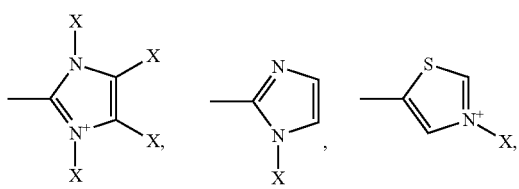

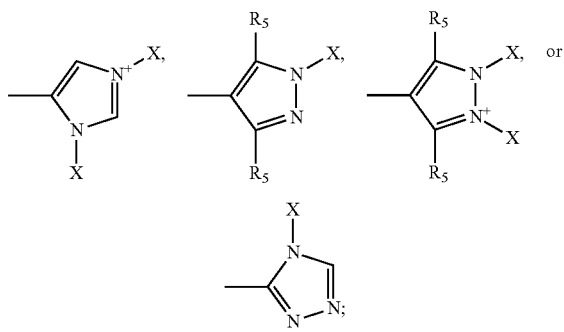

Y is halogen or —CO₂X, each X is the same or different and is an alkyl and each $R_5$ is the same or different (preferably the same) and is H or alkyl.

Preferably, $R_1$ and $R_3$ are the same and are:

—H, —CF₃, —CO₂—X, 

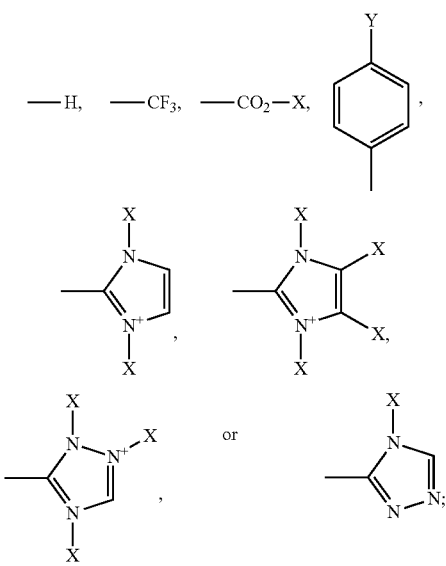

$R_2$ and $R_4$ are the same and are:

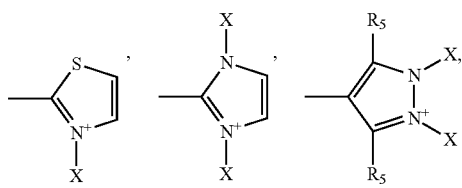

-continued

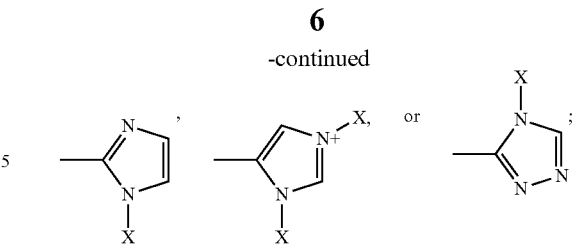

Y is —F or —CO₂X each X is the same or different and is an alkyl (preferably, $C_{1-4}$ alkyl, e.g., methyl or ethyl) and each $R_5$ is the same or different (preferably the same) and is H or alkyl (preferably, $C_{1-4}$ alkyl, e.g., —CH₃ or —CH₂CH₃).

Most preferably, $R_1$, $R_2$, $R_3$ and $R_4$ are the same and are

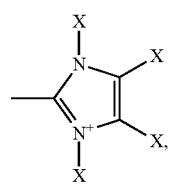

or and each X is the same or different and is $C_{1-4}$ alkyl, advantageously, methyl or ethyl, particularly, methyl.

Specific examples of mimetics of the invention are shown in FIGS. 1A-1F, together with activity data.

In addition to the methine (meso) substituents described above, one or more of the pyrrole rings of the porphyrin of Formula I can be substituted at any or all beta carbons, i.e.: 2, 3, 7, 8, 12, 13, 17 or 18. Such substituents, designated P, can be hydrogen or an electron withdrawing group, for example, each P can, independently, be a NO₂ group, a halogen (e.g., Cl, Br or F), a nitrile group, a vinyl group, or a formyl group. Such substituents alter the redox potential of the porphyrin and thus enhance its ability to scavenge oxygen radicals. For example, there can be 1, 2, 3, 4, 5, 6, 7, or 8 halogen (e.g., Br) substituents (preferably, 1-4), the remaining P's advantageously being hydrogen. When P is formyl, it is preferred that there not be more than 2 (on non-adjacent carbons), more preferably, 1, the remaining P's preferably being hydrogen. When P is NO₂, it is preferred that there not be more than 4 (on non-adjacent carbons), more preferably, 1 or 2, the remaining P's being hydrogen.

Where isomers are possible, all such isomers of the herein described mimetics are within the scope of the invention.

Mimetics preferred for use in the present methods can be selected by assaying for SOD, catalase and/or peroxidase activity. Mimetics can also be screened for their ability to inhibit lipid peroxidation or scavenge ONOO⁻ (as determined by the method of Szabo et al., FEBS Lett. 381:82 (1996)).

SOD activity can be monitored in the presence and absence of EDTA using the method of McCord and Fridovich (J. Biol.

Chem. 244:6049 (1969)). The efficacy of a mimetic can also be determined by measuring the effect of the mimetic on the aerobic growth of a SOD null *E. coli* strain versus a parent strain. Specifically, parental *E. coli* (AB1157) and SOD null *E. coli*. (JI132) can be grown in M9 medium containing 0.2% casamino acids and 0.2% glucose at pH 7.0 and 37° C.; growth can be monitored in terms of turbidity followed at 700 nm. This assay can be made more selective for SOD mimetics by omitting the branched chain, aromatic and sulphur-containing amino acids from the medium (glucose minimal medium (M9), plus 5 essential amino acids).

Efficacy of active mimetics can also be assessed by determining their ability to protect mammalian cells against methylviologen (paraquat)-induced toxicity. Specifically, rat L2 cells grown as described below and seeded into 24 well dishes can be pre-incubated with various concentrations of the SOD mimetic and then incubated with a concentration of methylviologen previously shown to produce an $LC_{75}$ in control L2 cells. Efficacy of the mimetic can be correlated with a decrease in the methylviologen-induced LDH release (St. Clair et al., FEBS Lett. 293:199 (1991)).

The efficacy of SOD mimetics can be tested in vivo with mouse and/or rat models using both aerosol administration and parenteral injection. For example, male Balb/c mice can be randomized into 4 groups of 8 mice each to form a standard 2×2 contingency statistical model. Animals can be treated with either paraquat (40 mg/kg, ip) or saline and treated with SOD mimetic or vehicle control.

Lung injury can be assessed 48 hours after paraquat treatment by analysis of bronchoalveolar lavage fluid (BALF) damage parameters (LDH, protein and % PMN) as previously described (Hampson et al., Tox. Appl. Pharm. 98:206 (1989); Day et al., J. Pharm. Methods 24:1 (1990)). Lungs from 2 mice of each group can be instillation-fixed with 4% paraformaldehyde and processed for histopathology at the light microscopic level.

Catalase activity can be monitored by measuring absorbance at 240 nm in the presence of hydrogen peroxide (see Beers and Sizer, J. Biol. Chem. 195:133 (1952)) or by measuring oxygen evolution with a Clark oxygen electrode (Del Rio et al., Anal. Biochem. 80:409 (1977)).

Peroxidase activity can be measured spectrophotometrically as previously described by Putter and Becker: Peroxidases. In: Methods of Enzymatic Analysis, H. U. Bergmeyer (ed.), Verlag Chemie, Weinheim, pp. 286-292 (1983). Aconitase activity can be measured as described by Gardner and Fridovich (J. Biol. Chem. 266:19328 (1991)). The selective, reversible and SOD-sensitive inactivation of aconitase by known $O_2^-$ generators can be used as a marker of intracellular $O_2^-$ generation. Thus, suitable mimetics can be selected by assaying for the ability to protect aconitase activity.

The ability of mimetics to inhibit lipid peroxidation can be assessed as described by Ohkawa et al. (Anal. Biochem. 95:351 (1979)) and Yue et al. (J. Pharmacol. Exp. Ther. 263: 92 (1992)). Iron and ascorbate can be used to initiate lipid peroxidation in tissue homogenates and the formation of thiobarbituric acid reactive species (TBARS) measured.

Active mimetics can be tested for toxicity in mammalian cell culture by measuring lactate dehydrogenase (LDH) release. Specifically, rat L2 cells (a lung Type II like cell (Kaighn and Douglas, J. Cell Biol. 59:160a (1973)) can be grown in Ham's F-12 medium with 10% fetal calf serum supplement at pH 7.4 and 37° C.; cells can be seeded at equal densities in 24 well culture dishes and grown to approximately 90% confluence; SOD mimetics can be added to the cells at log doses (e.g., micromolar doses in minimal essential medium (MEM)) and incubated for 24 hours. Toxicity can be assessed by morphology and by measuring the release of the cytosolic injury marker, LDH (e.g., on a thermokinetic plate reader), as described by Vassault (In: Methods of Enzymatic Analysis, Bergmeyer (ed) pp. 118-26 (1983); oxidation of NADH is measured at 340 nm).

The mimetics of the present invention are suitable for use in a variety of methods. The compounds of Formula I, particularly the metal bound forms (advantageously, the manganese bound forms), are characterized by the ability to inhibit lipid peroxidation. Accordingly, these compounds are preferred for use in the treatment of diseases or disorders associated with elevated levels of lipid peroxidation. The compounds are further preferred for use in the treatment of diseases or disorders mediated by oxidative stress. Inflammatory diseases are examples, including asthma, inflammatory bowel disease, arthritis and vasculitis.

The compounds of the invention (advantageously, metal bound forms thereof) can also be used in methods designed to regulate NO. levels by targeting the above-described porphines to strategic locations. NO is an intercellular signal and, as such, No. must traverse the extracellular matrix to exert its effects. NO however, is highly sensitive to inactivation mediated by $O_2^-$ present in the extracellular spaces. The methine (meso) substituted porphyrins of the invention can increase bioavailability of No. by preventing its degradation by $O_2^-$.

The present invention relates, in a further specific embodiment, to a method of inhibiting production of superoxide radicals. In this embodiment, the mimetics of the invention (particularly, metal bound forms thereof) are used to inhibit oxidases, such as xanthine oxidase, that are responsible for production of superoxide radicals. The ability of a mimetic to protect mammalian cells from xanthine/xanthine oxidase-induced injury can be assessed, for example, by growing rat L2 cells in 24-well dishes. Cells can be pre-incubated with various concentrations of a mimetic and then xanthine oxidase (XO) can be added to the culture along with xanthine (X). The appropriate amount of XO/X used in the study can be pre-determined for each cell line by performing a dose-response curve for injury. X/XO can be used in an amount that produces approximately an $LC_{75}$ in the culture. Efficacy of the mimetic can be correlated with a decrease in XO/X-induced LDH release.

The mimetics of the invention (particularly, metal bound forms thereof) can also be used as catalytic scavengers of reactive oxygen species to protect against ischemia reperfusion injuries associated with myocardial infarction, coronary bypass surgery, stroke, acute head trauma, organ reperfusion following transplantation, bowel ischemia, hemorrhagic shock, pulmonary infarction, surgical occlusion of blood flow, and soft tissue injury. The mimetics (particularly, metal bound forms) can further be used to protect against skeletal muscle reperfusion injuries. The mimetics (particularly, metal bound forms) can also be used to protect against damage to the eye due to sunlight (and to the skin) as well as glaucoma, cataract and macular degeneration of the eye. The mimetics (particularly, metal bound forms) can also be used to treat burns and skin diseases, such as dermatitis, psoriasis and other inflammatory skin diseases. Diseases of the bone are also amenable to treatment with the mimetics. Further, connective tissue disorders associated with defects in collagen synthesis or degradation can be expected to be susceptible to treatment with the present mimetics (particularly, metal bound forms), as should the generalized deficits of aging. Liver cirrhosis and renal diseases (including glomerula nephritis, acute tabular necrosis, nephroderosis and dialysis induced complications) are also amenable to treatment with the present mimetics (particularly, metal bond forms thereof).

The mimetics of the invention (particularly, metal bound forms) can also be used as catalytic scavengers of reactive oxygen species to increase the very limited storage viability of transplanted hearts, livers, lungs, kidneys, skin and other organs and tissues. The invention also provides methods of inhibiting damage due to autoxidation of substances resulting in the formation of $O_2^-$ including food products, pharmaceuticals, stored blood, etc. To affect this end, the mimetics of the invention are added to food products, pharmaceuticals, stored blood and the like, in an amount sufficient to inhibit or prevent oxidation damage and thereby to inhibit or prevent the degradation associated with the autoxidation reactions. (For other uses of the mimetics of the invention, see U.S. Pat. No. 5,227,405). The amount of mimetic to be used in a particular treatment or to be associated with a particular substance can be determined by one skilled in the art.

The mimetics (particularly, metal bound forms) of the invention can further be used to scavenge hydrogen peroxide and thus protect against formation of the highly reactive hydroxyl radical by interfering with Fenton chemistry (Aruoma and Halliwell, Biochem. J. 241:273 (1987); Mello Filho et al., Biochem. J. 218:273 (1984); Rush and Bielski, J. Phys. Chem. 89:5062 (1985)). The mimetics (particularly, metal bound forms) of the invention can also be used to scavenge peroxynitrite, as demonstrated indirectly by inhibition of the oxidation of dihydrorhodamine 123 to rhodamine 123 and directly by accelerating peroxynitrite degradation by stop flow analysis.

Further examples of specific diseases/disorders appropriate for treatment using the mimetics of the present invention, advantageously, metal bound forms, include diseases of the cardiovascular system (including cardiomyopathy, ischemia and atherosclerotic coronary vascular disease), central nervous system (including AIDS dementia, stroke, amyotrophic lateral sclerosis (ALS), Parkinson's disease and Huntington's disease) and diseases of the musculature (including diaphramic diseases (e.g., respiratory fatigue in chronic obstructive pulmonary disease, cardiac fatigue of congestive heart failure, muscle weakness syndromes associated with myopathies, ALS and multiple sclerosis). Many neurologic disorders (including epilepsy, stroke, Huntington's disease, Parkinson's disease, ALS, Alzheimer's and AIDS dementia) are associated with an over stimulation of the major subtype of glutamate receptor, the NMDA (or N-methyl-D-aspartate) subtype. On stimulation of the NMDA receptor, excessive neuronal calcium concentrations contribute to a series of membrane and cytoplasmic events leading to production of oxygen free radicals and nitric oxide (NO.). Interactions between oxygen free radicals and NO. have been shown to contribute to neuronal cell death. Well-established neuronal cortical culture models of NMDA-toxicity have been developed and used as the basis for drug development. In these same systems, the mimetics of the present invention inhibit NMDA induced injury. The formation of $O_2^-$ radicals is an obligate step in the intracellular events culminating in excitotoxic death of cortical neurons and further demonstrate that the mimetics of the invention can be used to scavenge $O_2^-$ radicals and thereby serve as protectants against excitotoxic injury.

The present invention also relates to methods of treating AIDS. The Nf Kappa B promoter is used by the HIV virus for replication. This promoter is redox sensitive, therefore, an oxidant can regulate this process. This has been shown previously for two metalloporphyrins distinct from those of the present invention (Song et al., Antiviral Chem. and Chemother. 8:85 (1997)). The invention also relates to methods of treating systemic hypertension, atherosclerosis, edema, septic shock, pulmonary hypertension, including primary pulmonary hypertension, impotence, infertility, endometriosis, premature uterine contractions, microbial infections, gout and in the treatment of Type I or Type II diabetes mellitus. The mimetics of the invention (particularly, metal bound forms) can be used to ameliorate the toxic effects associated with endotoxin, for example, by preserving vascular tone and preventing multi-organ system damage.

As indicated above, inflammations, particularly inflammations of the lung, are amenable to treatment using the present mimetics (particularly, metal bound forms) (particularly the inflammatory based disorders of emphysema, asthma, ARDS including oxygen toxicity, pneumonia (especially AIDS-related pneumonia), cystic fibrosis, chronic sinusitis, arthritis and autoimmune diseases (such as lupus or rheumatoid arthritis)). Pulmonary fibrosis and inflammatory reactions of muscles, tendons and ligaments can be treated using the present mimetics (particularly metal bound forms thereof). EC-SOD is localized in the interstitial spaces surrounding airways and vasculature smooth muscle cells. EC-SOD and $O_2^-$ mediate the antiinflammatory-proinflammatory balance in the alveolar septum. NO. released by alveolar septal cells acts to suppress inflammation unless it reacts with $O_2^-$ to form $ONOO^-$. By scavenging $O_2^-$, EC-SOD tips the balance in the alveolar septum against inflammation. Significant amounts of $ONOO^-$ will form only when EC-SOD is deficient or when there is greatly increased $O_2^-$ release. Mimetics described herein can be used to protect against destruction caused by hyperoxia.

The invention further relates to methods of treating memory disorders. It is believed that nitric oxide is a neurotransmitter involved in long-term memory potentiation. Using an EC-SOD knocked-out mouse model (Carlsson et al., Proc. Natl. Acad. Sci. USA 92:6264 (1995)), it can be shown that learning impairment correlates with reduced superoxide scavenging in extracellular spaces of the brain. Reduced scavenging results in higher extracellular $O_2^-$ levels. $O_2^-$ is believed to react with nitric oxide thereby preventing or inhibiting nitric oxide-mediated neurotransmission and thus long-term memory potentiation. The mimetics of the invention, particularly, metal bound forms, can be used to treat dementias and memory/learning disorders.

The availability of the mimetics of the invention also makes possible studies of processes mediated by $O_2^-$, hydrogen peroxide, nitric oxide and peroxynitrite.

The mimetics described above, metal bound and metal free forms, can be formulated into pharmaceutical compositions suitable for use in the present methods. Such compositions include the active agent (mimetic) together with a pharmaceutically acceptable carrier, excipient or diluent. The composition can be present in dosage unit form for example, tablets, capsules or suppositories. The composition can also be in the form of a sterile solution suitable for injection or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought.

The dosage of the composition of the invention to be administered can be determined without undue experimentation and will be dependent upon various factors including the nature of the active agent (including whether metal bound or metal free), the route of administration, the patient, and the result sought to be achieved. A suitable dosage of mimetic to be administered IV or topically can be expected to be in the range of about 0.01 to 50 mg/kg/day, preferably, 0.1 to 10 mg/kg/day. For aerosol administration, it is expected that doses will be in the range of 0.001 to 5.0 mg/kg/day, preferably, 0.01 to 1 mg/kg/day. Suitable doses of mimetics will vary, for example, with the mimetic and with the result sought.

Certain aspects of the present invention will be described in greater detail in the non-limiting Examples that follow. (The numbering of the compounds in Example I is for purposes of that Example only.)

Example I

Syntheses

I. [5,15-Bis(4-carbomethoxyphenyl)-10,20-(thiazol-5-yl)porphyrinato]-manganese(III) Chloride (5)

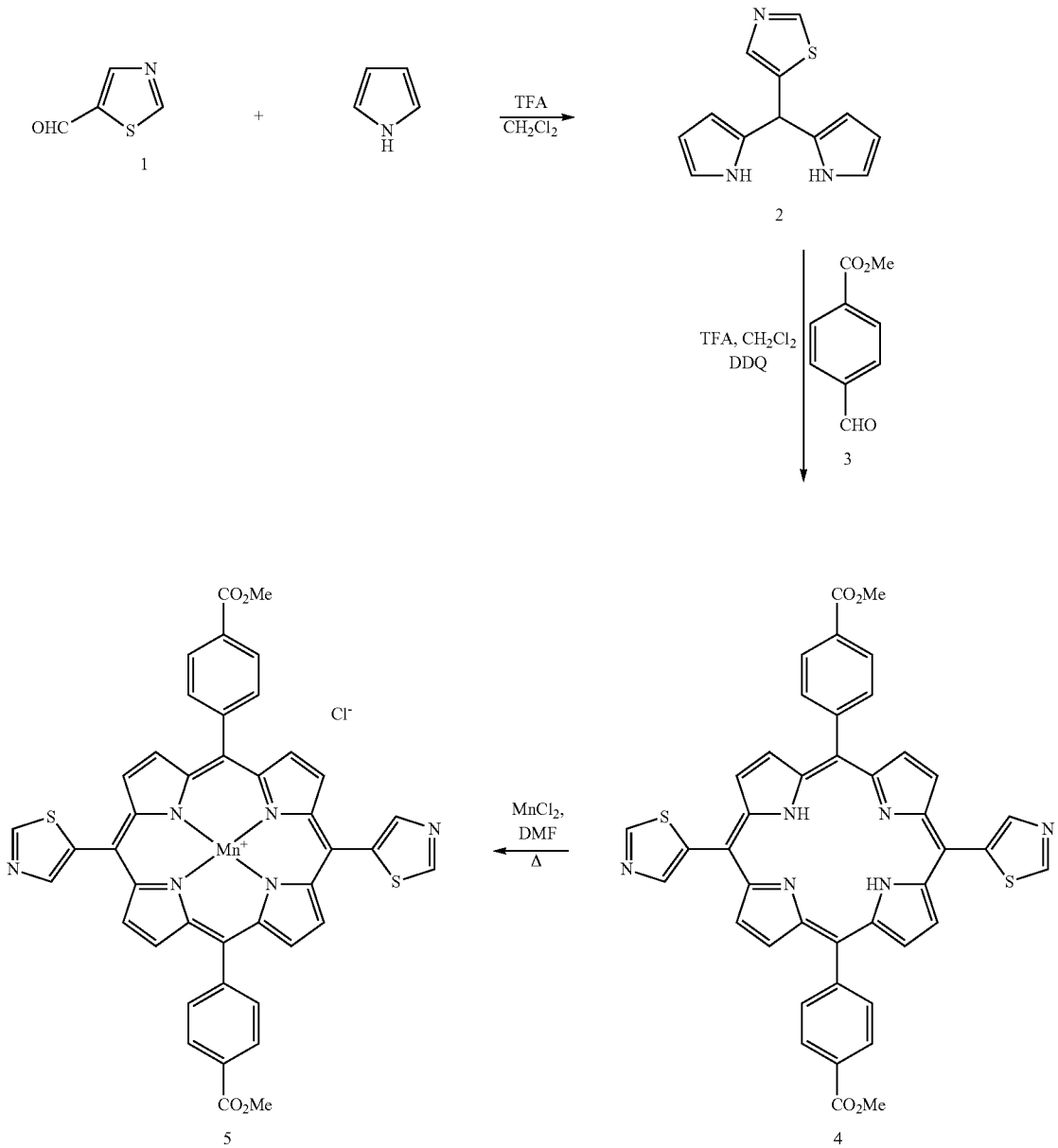

1. meso-(Thiazol-5-yl)dipyrromethane (2)

In a foil-covered 250-mL three-necked flask, equipped with a magnetic stirrer and $N_2$ inlet, was placed 5-thiazole-carboxaldehyde (1, 0.88 g, 7.81 mmol) (Dondoni, A.; Fantin, G.; Fogagnolo, M.; Medici, A.; Pedrini, P. *Synthesis* 1987, 998-1001), $CH_2Cl_2$ (30 mL), and pyrrole (6 mL, 87 mmol). The reaction mixture was stirred for 10 min, then TFA (0.25 mL, 3.2 mmol) was added. After a stirring period of 2 h at room temperature, the reaction mixture was transferred to a separatory funnel and washed with saturated aqueous $NaHCO_3$ (50 mL), $H_2O$ (50 mL) and brine (50 mL). The organic layer was dried ($Na_2SO_4$), filtered, and concentrated in vacuo. The residue was dissolved in $CH_2Cl_2$ (50 mL) and adsorbed onto silica gel (3 g). Purification by column chromatography (gradient elution 33-67% EtOAc/hexanes) provided dipyrromethane 2 (0.95 g, 52%) as a gray solid: $^1$H NMR (300 MHz, CDCl$_3$) δ 5.74 (s, 1H), 6.02 (m, 2H), 6.17 (m, 2H), 6.70 (m, 2H), 7.58 (s, 1H), 8.19 (br s, 2H), 8.68 (s, 1H).

2. 5,15-Bis(4-carbomethoxyphenyl)-10,20-(thiazol-5-yl)porphyrin (4)

In a foil-covered 250-mL three-necked round bottom flask, equipped with a magnetic stirrer and a $N_2$ outlet, was added methyl 4-formylbenzoate (3, 180 mg, 1.09 mmol), dipyrromethane 2 (249 mg, 1.09 mmol), and $CH_2Cl_2$ (110 mL). The reaction mixture was stirred for 15 min, then TFA (0.25 mL, 3.25 mmol) was added. After a stirring period of 2.5 h at room temperature, DDQ (372 mg, 1.64 mmol) was added. The reaction mixture was stirred overnight and the solvent was removed in vacuo. The crude residue was adsorbed onto silica gel (3 g) then purified by column chromatography (gradient elution 0-1.5% MeOH/$CH_2Cl_2$) to provide porphyrin 4 (80 mg, 10% yield) as a purple solid: $^1$H NMR (300 MHz, CDCl$_3$) δ -2.75 (s, 2H), 4.11 (s, 6H), 8.28 (d, 4H), 8.47 (d, 4H), 8.65 (s, 2H), 8.82 (d, 4H), 8.99 (d, 4H), 9.33 (s, 2H).

3. [5,15-Bis(4-carbomethoxyphenyl)-10,20-(thiazol-5-yl)porphyrinato]-manganese(III) Chloride (5)

A solution of porphyrin 4 (75 mg, 0.101 mmol) and MnCl2 (129 mg, 1.03 mmol) in DMF (15 mL) was heated at 125° C. for 14.5 h. The mixture was cooled to room temperature while exposed to a stream of air, then concentrated in vacuo. Repeated chromatographic purification of the product (gradient elution 5-10% MeOH/CH2Cl2) provided porphyrin 5 (7 mg, 8%) as a dark green solid: mp>300° C.; UV-vis λmax=466.0 nm, ε=1.34×105 L/cm-mol; API MS m/z=797 [C42H26MnN6O4S2]+.

II. [5,10,15,20-Tetrakis(thiazol-5-yl)porphyrinato]manganese(III) Chloride (7) and [5,10,15,20-Tetrakis (3-methylthiazolium-5-yl)porphyrinato]-manganese (III) Pentachloride (9)

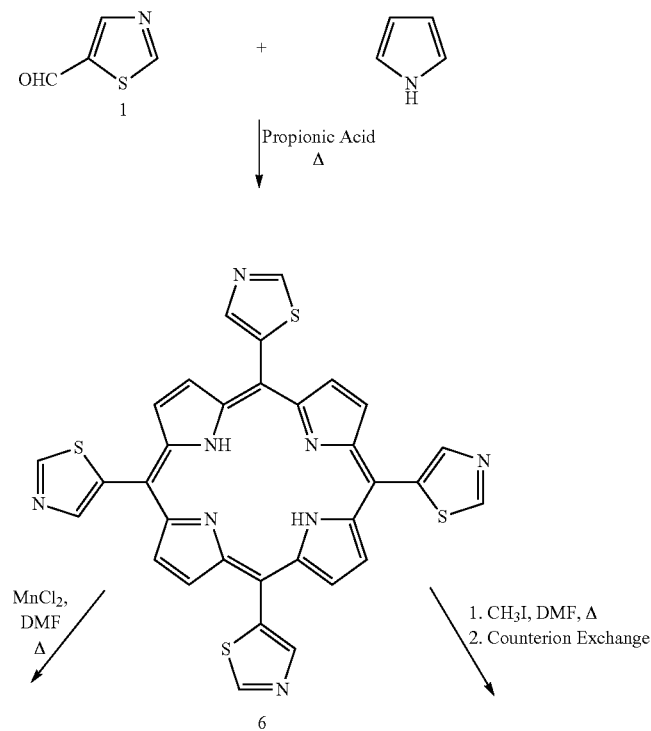

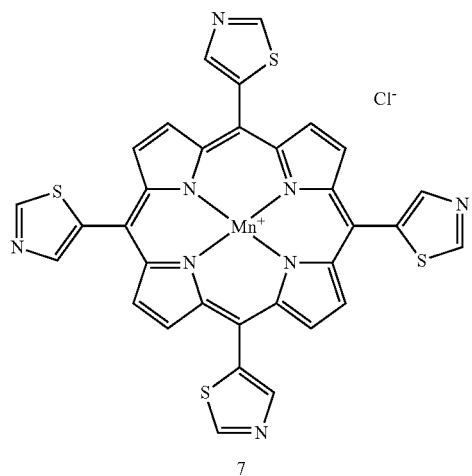

7

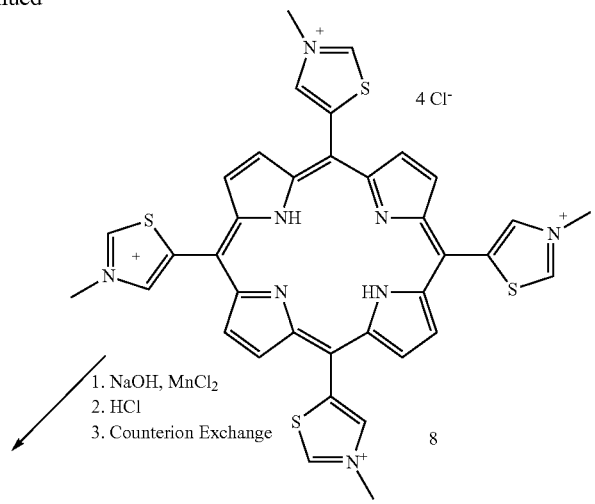

8

1. NaOH, MnCl₂
2. HCl
3. Counterion Exchange

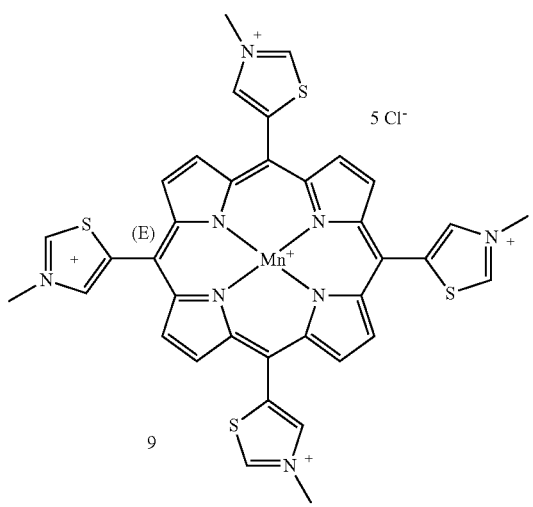

9

1. 5,10,15,20-Tetrakis(thiazol-5-yl)porphyrin (6)

A 250-mL three-necked flask equipped with a condenser and charged with propionic acid (60 mL) was heated to reflux. 5-Thiazolecarboxaldehyde (1, 373 mg, 3.30 mmol), pyrrole (230 μL, 3.32 mmol), and an additional 5 mL of propionic acid were added. After 3.5 h at reflux, the mixture was cooled to room temperature while exposed to a stream of air. The solvent was removed in vacuo, the residue was redissolved in CHCl₃/MeOH/concentrated NH₄OH (6:3:1; 100 mL), and the solvent was removed in vacuo. The residue was adsorbed onto silica gel (3 g) and purified by column chromatography (gradient elution, 1-2% MeOH/CH₂Cl₂) to provide porphyrin 6 (123 mg, 14%) as a solid: $^1$H NMR (300 MHz, CDCl₃) δ −2.70 (s, 2H), 8.67 (s, 4H), 9.02 (s, 8H), 9.38 (s, 4H).

2. [5,10,15,20-Tetrakis(thiazol-5-yl)porphyrinato]manganese(III) Chloride (7)

A solution of porphyrin 6 (61 mg, 0.115 mmol) and MnCl₂ (144 mg, 1.14 mmol) in DMF (15 mL) was heated at 125° C. for 7.5 h. A stream of air was introduced and the reaction mixture was warmed to 130° C. After a stirring period of 1.5 h, the reaction mixture was cooled to room temperature. The solvent was evaporated in vacuo, and the residue was adsorbed onto silica gel (2 g). Purification by column chromatography (gradient elution, 10-20% MeOH/CH₂Cl₂) provided porphyrin 7 (36 mg, 43%) as a dark green solid: mp>300° C.; UV-vis $\lambda_{max}$=466.5 nm, ε=3.55×10⁴ L/cm-mol; FAB MS m/z=695 [C₃₂H₁₆MnN₈S₄]⁺.

3. 5,10,15,20-Tetrakis(3-methylthiazolium-5-yl)porphyrin Tetrachloride (8)

A solution of 6 (123 mg, 0.19 mmol), CH₃I (5 mL), and DMF (5 mL) in a sealed tube was heated at 100° C. for 24 h. The crude porphyrin iodide salt that precipitated out of the reaction mixture was filtered, washed alternately with CH₂Cl₂ and ether, and dried under vacuum at room temperature. The iodide was dissolved in water, precipitated out as the hexafluorophosphate salt (by dropwise addition of aqueous NH₄⁺PF₆⁻ solution; 1 g/10 mL), filtered, washed with water and isopropanol, and vacuum dried at room temperature. The hexafluorophosphate salt was dissolved in acetone then filtered (to remove insoluble solids). The product was precipitated out as the chloride salt from the filtrate by dropwise addition of a solution of Bu₄NH₄⁺Cl⁻ in acetone (1 g/10 mL), filtered, washed with copious quantities of acetone, and dried under vacuum at room temperature, to provide porphyrin 8 (66 mg, 41%): $^1$H NMR (300 MHz, DMSO-d₆) −3.1 (s, 2H), 4.6 (s, 12H), 9.49 (s, 4H), 9.58 (s, 8H), 10.85 (s, 4H).

4. [5,10,15,20-Tetrakis(3-methylthiazolium-5-yl) porphyrinato]manganese(III) Pentachloride (9)

Porphyrin 8 (60 mg, mmol) was dissolved in water (15 mL) and the solution pH was adjusted to pH=12 by dropwise addition of 6N NaOH. Solid $MnCl_2$ (147 mg) was added into the reaction mixture (the resulting pH=8.7). After a stirring period of 30-60 min, the reaction mixture was filtered through a fritted funnel lined with a filter paper. The pH of the filtrate was adjusted to pH=4-5 (1N HCl) then the solution was filtered. Purification by the double precipitation method (as described for the preparation of 8) provided porphyrin 9 (6 mg, 8.2%) as a dark brown solid: mp>300° C.; UV-vis $\lambda_{max}$=460.0 nm, $\epsilon$=1.25×10$^5$ L/cm-mol.

III. [5,15-Bis(thiazol-5-yl)porphyrinato]manganese(III) Chloride (12)

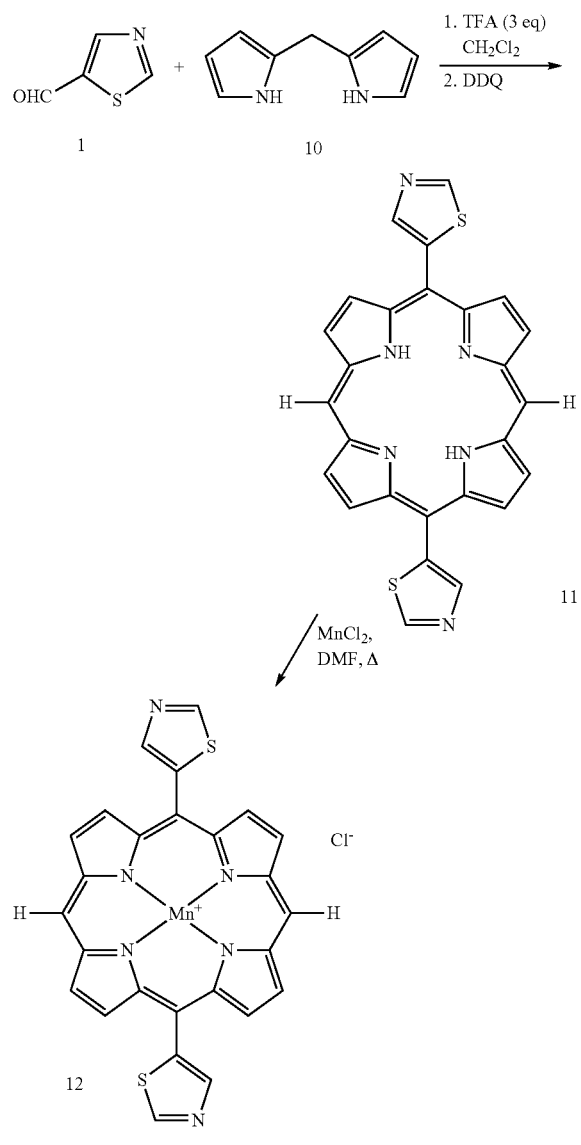

1. 5,15-Bis(thiazol-5-yl)porphyrin (11)

In a foil-covered 500-mL three-necked round bottom flask, equipped with magnetic stirrer and a $N_2$ inlet, was added dipyrromethane 10 (288 mg, 1.97 mmol) (Chong, R.; Clezy, P. S.; Liepa, A. J.; Nichol, A. W. *Aust. Chem.* 1969, 22, 229), 5-thiazolecarboxaldehyde (1, 223 mg, 1.97 mmol), $CH_2Cl_2$ (198 mL) and sodium chloride (13 mg, 0.2 mmol). The reaction mixture was stirred vigorously for 10 min, then TFA (0.46 mL, 5.97 mmol) was added. After a stirring period of 40 min, DDQ (671 mg, 2.96 mmol) was added, and the reaction mixture was stirred for an additional 4 h. The solvent was evaporated in vacuo, and the residue was adsorbed onto silica gel (3 g). Repeated chromatographic purification (gradient elution 0.5-2% MeOH/$CH_2Cl_2$) provided porphyrin 11 (28 mg, 6%) as a solid: $^1$H NMR (300 MHz, CDCl$_3$) δ -3.07 (s, 2H), 8.69 (s, 2H), 9.21 (d, 4H), 9.39 (s, 2H), 9.43 (d, 4H), 10.35 (s, 2H).

2. [5,15-Bis(thiazol-5-yl)porphyrinato]manganese(III) Chloride (12)

A solution of porphyrin 11 (28 mg, 0.0587 mmol) and $MnCl_2$ (85 mg, 0.675 mmol) in DMF (8 mL) was heated at 125° C. for 15 h. The mixture was cooled to room temperature while exposed to a stream of air, and the solvent was removed by rotary evaporation. The residue was dissolved in 10% MeOH/$CH_2Cl_2$ (50 mL) and adsorbed onto silica gel (500 mg). Purification by column chromatography (gradient of 5-10% MeOH/$CH_2Cl_2$) provided porphyrin 12 (29 mg, 86%) as a dark brown solid: mp>300° C.; UV-vis $\lambda_{max}$=457.5 nm, $\epsilon$=3.75×10$^4$ L/cm-mol; API MS m/z =529 $[C_{26}H_{14}MnN_6S_2]^+$.

IV. [5,15-Bis(4-carbomethoxyphenyl)-10,20-bis(3-methylthiazolium-2-yl) porphyrinato]manganese(III) Trichloride (16)

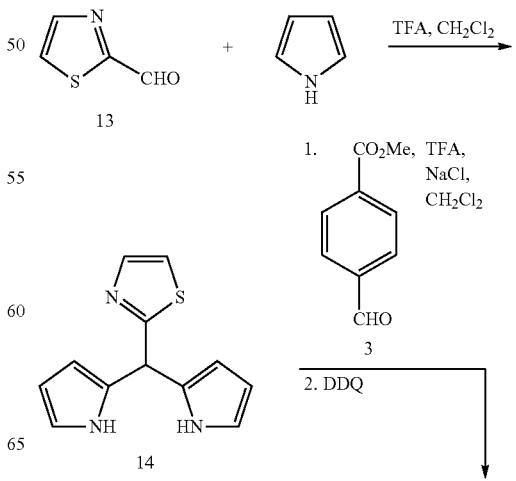

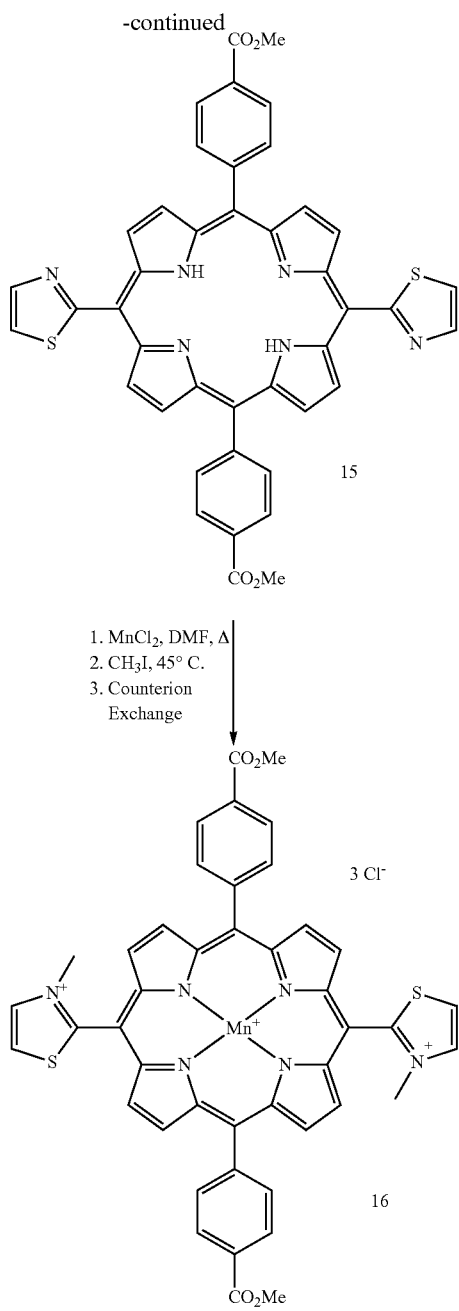

1. meso-(Thiazol-2-yl)dipyrromethane (14)

In a foil-covered 250-mL three-necked flask, equipped with a magnetic stirrer and a $N_2$ inlet, was placed 2-thiazole-carboxaldehyde (13, 0.97 g, 8.6 mmol) (Dondoni, A.; Fantin, G.; Fogagnolo, M.; Medici, A.; Pedrini, P. *Synthesis* 1987, 998-1001), $CH_2Cl_2$ (35 mL), and pyrrole (7.2 mL, 104 mmol). The reaction mixture was stirred for 10 min, then TFA (0.26 mL, 3.4 mmol) was added. After a stirring period of 1 h at room temperature, the reaction mixture was transferred to a separatory funnel and washed with saturated aqueous $NaHCO_3$ (50 mL), $H_2O$ (50 mL), and brine (50 mL) The organic layer was dried ($Na_2SO_4$), filtered, and concentrated in vacuo. The residue was dissolved in $CH_2Cl_2$ (50 mL), and adsorbed onto silica gel (3 g). Purification by column chromatography (1:1 ether/hexanes) provided dipyrromethane 14 (1.22 g, 62%) as a solid: $^1$H NMR (300 MHz, $CDCl_3$) δ 5.78 (s, 1H), 6.04 (s, 2H), 6.15 (m, 2H), 6.71 (m, 2H), 7.20 (d, 1H), 7.74 (d, 1H), 8.81 (br s, 1H).

2. 5,15-Bis(4-carbomethoxyphenyl)-10,20-(thiazol-2-yl)porphyrin (15)

In a foil-covered 500-mL three-necked round bottom flask, equipped with a magnetic stirrer and a $N_2$ outlet, was added dipyrromethane 14 (771 mg, 3.39 mmol), methyl 4-formylbenzoate (3, 0.557 g, 3.36 mmol) and $CH_2Cl_2$ (350 mL). The reaction mixture was stirred for 15 min, then TFA (0.8 mL, 10.4 mmol) was added. After a stirring period of 3 h at room temperature, DDQ (1.16 g, 1.64 mmol) was added. The reaction mixture was stirred for 2 d, then the solvent was removed in vacuo. The residue was adsorbed onto silica gel (4 g) and purified by column chromatography (gradient elution 0.5-1% MeOH/$CH_2Cl_2$) to provide porphyrin 15 (140 mg, 11%) as a purple solid: (300 MHz, $CDCl_3$) δ −2.29 (s, 2H), 4.12 (s, 6H), 8.02 (d, 2H), 8.30 (d, 4H), 8.44 (d, 2H), 8.47 (d, 4H), 8.84 (d, 4H), 9.05 (d, 4H).

3. [5,15-Bis(4-carbomethoxyphenyl)-10,20-bis(3-methylthiazolium-2-yl)-porphyrinato]manganese(III) Trichloride (16)

A solution of porphyrin 15 (26 mg, 0.054 mmol) and $MnCl_2$ (40 mg, 0.40 mmol) in DMF (20 mL) was heated at 135° C. overnight. The mixture was cooled to 45° C. and $CH_3I$ (0.8 mL, 11.2 mmol) was added. The reaction mixture was stirred for 36 h at 45° C. and DMF was evaporated in vacuo. The residue was purified by column chromatography (gradient elution EtOAc, $CHCl_3$, MeOH, concentrated $NH_4OH$) to provide the product contaminated with impurities. Following a second purification by column chromatography (6:3:1 $CHCl_3$/MeOH/concentrated $NH_4OH$) non-polar fractions were collected leaving the bulk of product at the top of the column. The top silica gel containing the product was collected and washed with $CHCl_3$/MeOH/1N HCl (6:4:1). Evaporation of the acidic solution provided the product that contained excess inorganic salts. Purification by the double precipitation method and vacuum drying at 35° C. for 2 d provided porphyrin 16 (9 mg, 28%) as a black solid: mp>300° C.; UV-vis $\lambda_{max}$=459.0 nm; $\epsilon$=1.36×10$^5$L/cm-mol; API MS m/z=886 $[C_{44}H_{32}MnN_6O_4S_2+CH_3CO_2^-]^{+2}$.

V. [5,15-Bis(3-methylthiazolium-2-yl)porphyrinato]manganese(III) Trichloride (19)

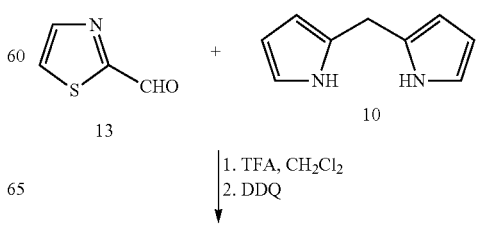

1. TFA, $CH_2Cl_2$
2. DDQ

-continued

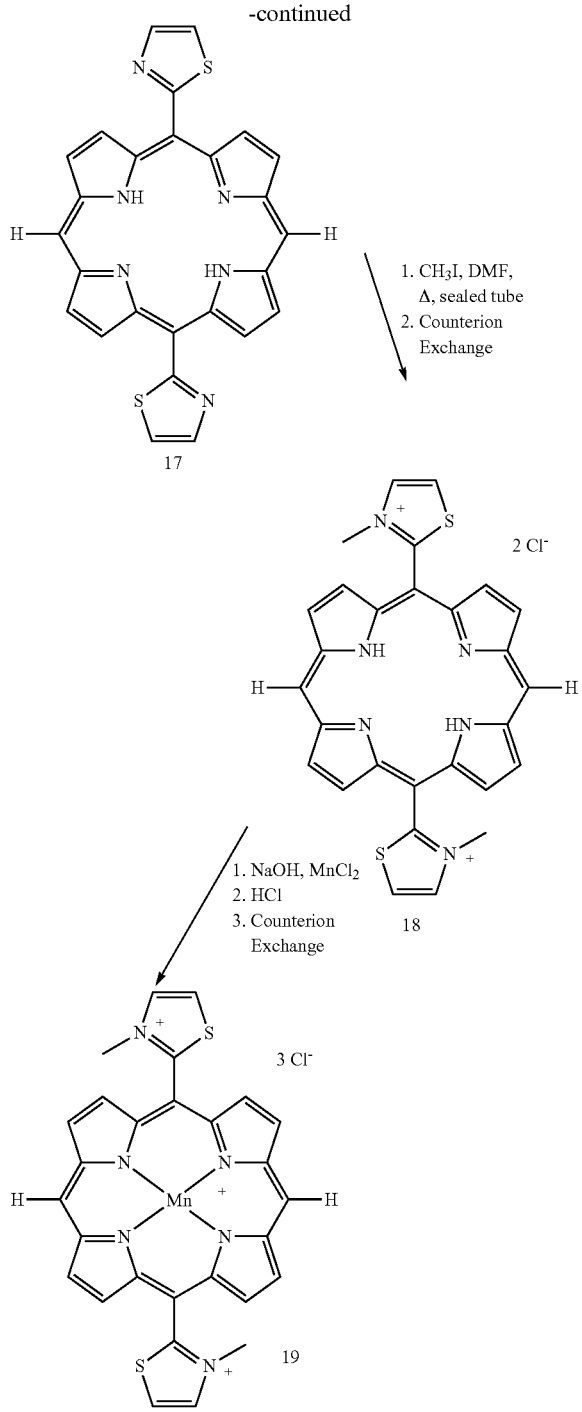

1. 5,15-Bis(thiazol-2-yl)porphyrin (17)

In a foil-covered 500-mL three-necked round bottom flask, equipped with magnetic stirrer and a $N_2$ inlet, was added dipyrromethane (10, 677 mg, 4.6 mmol), 2-thiazol-carboxaldehyde (13, 524 mg, 4.6 mmol), and $CH_2Cl_2$ (450 mL). The reaction mixture was stirred for 10 min, then TFA (1 mL, 16.9 mmol) was added. After a stirring period of 1 h, DDQ (1.58 g, 7 mmol) was added and the reaction mixture was stirred overnight. The solvent was evaporated in vacuo, and the residue was adsorbed onto silica gel (3 g). Repeated purification by column chromatography (gradient elution 1-2% MeOH/$CH_2Cl_2$) provided porphyrin 17 (51 mg, 4.62%) as a purple solid: $^1H$ NMR (300 MHz, $CDCl_3$) δ −3.05 (s, 2H), 8.06 (d, 2H), 8.51 (d, 2H), 9.35 (d, 4H), 9.45 (d, 4H), 10.40 (s, 2H).

2. 5,15-Bis(3-methylthiazolium-2-yl)porphyrin Dichloride (18)

A solution of porphyrin 17 (140 mg, 0.29 mmol), $CH_3I$ (4 mL), and DMF (20 mL) in a sealed tube was heated at 100° C. for 48 h. The precipitate that formed during the reaction was filtered and washed with ether. Purification of the solid precipitate by the double precipitation method provided porphyrin 18 (120 mg, 71%) as a purple solid: $^1H$ NMR (300 MHz, DMSO-$d_6$) δ −3.4 (s, 2H), 4.09, 4.06 (2s, 6H, atropisomer N—$CH_3$), 9.07 (d, 2H), 9.2 (d, 2H), 9.4 (d, 4H), 9.9 (d, 4H), 10.96 (s, 2H).

3. [5,15-Bis(3-methylthiazolium-2-yl)porphyrinato]manganese(III) Trichloride (19)

Porphyrin 18 (120 mg, 0.21 mmol) was dissolved in water (25 mL) and the solution pH was adjusted to pH=12 by dropwise addition of 6N NaOH. Solid $MnCl_2$ (147 mg) was added (the resulting pH=8.7) and the reaction mixture was stirred for 30-60 min. The reaction mixture was filtered through a fitted funnel lined with a filter paper. The pH of the filtrate was adjusted to pH=4-5 (1N HCl) and the solution was filtered. The filtrate was subjected to the double precipitation method to provide a mixture of porphyrins 18 and 19. The resulting mixture was separated by column chromatography (9:0.5:0.5 $CH_3CN$/water/saturated $KNO_3$) to provide porphyrin 19 (25 mg, 18%) as a dark solid: mp>300° C.; UV-vis $\lambda_{max}$=450.5 nm, $\epsilon$=5.99×10$^4$ L/cm-mol.

VI. [5,10,15,20-Tetrakis(1-methylimidazol-2-yl)porphyrinato]manganese(III) Chloride (22) and [5,10,15,20-Tetrakis(1,3-dimethylimidazolium-2-yl)-porphyrinato]manganese(III) Pentachloride (24)

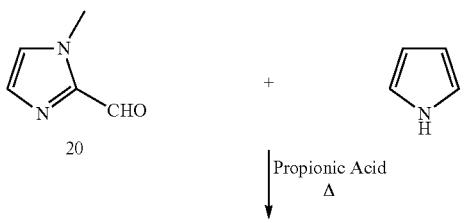

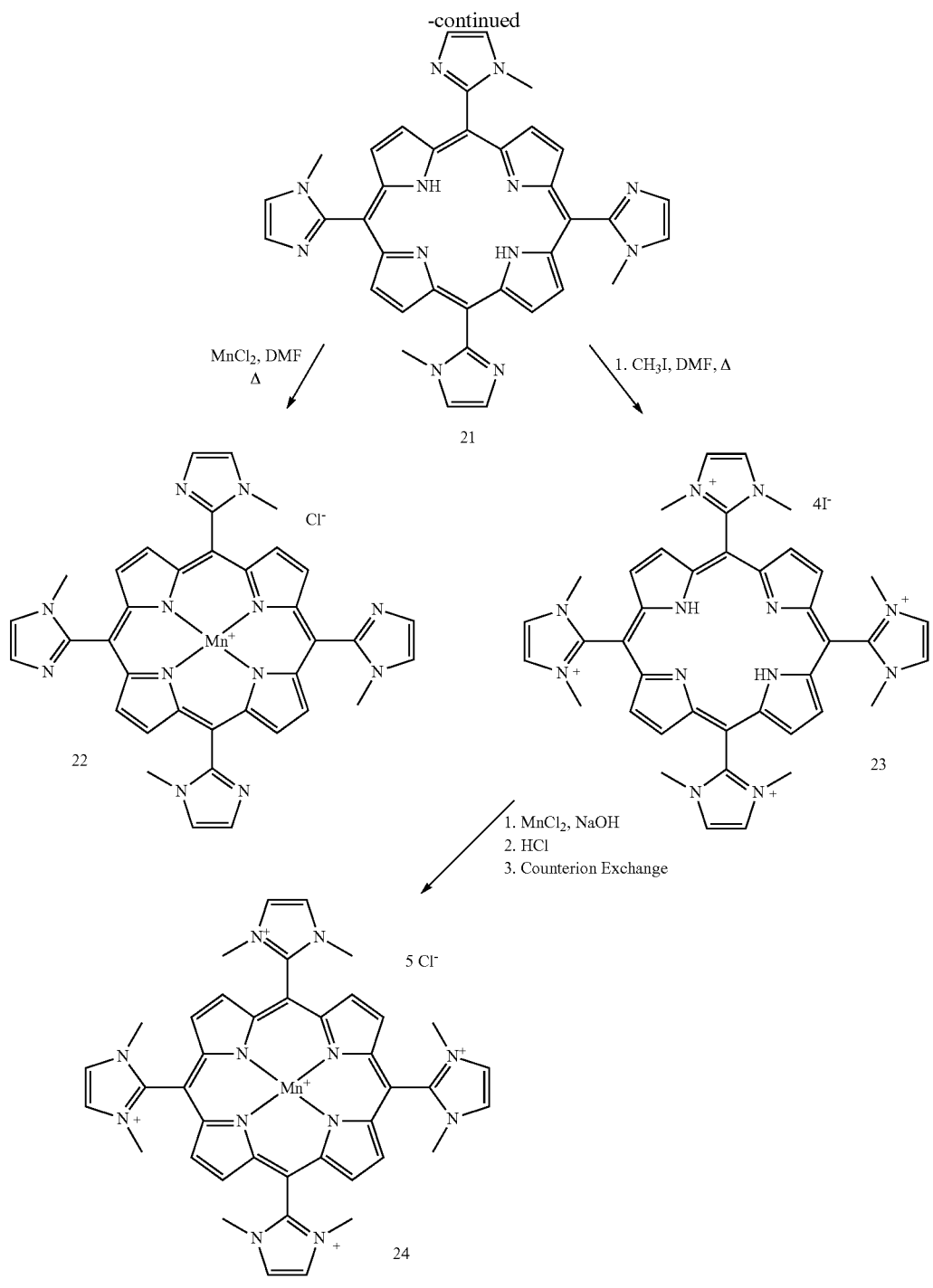

1. 5,10,15,20-Tetrakis(1-methylimidazol-2-yl)porphyrin (21)

In a foil-covered 1-L three-neck flask equipped with magnetic stirrer, thermometer, and condenser was placed aldehyde 20 (2.0 g, 18.2 mmol) and propionic acid (400 mL) The reaction mixture was heated to 120° C. at which time pyrrole (1.26 mL, 18.2 mmol) was added. The reaction mixture was heated under reflux for an additional 4.5 h and was stirred at room temperature for 3 d. The propionic acid was removed in vacuo, the dark residue was dissolved in a solution of 5% MeOH/CH$_2$Cl$_2$ and adsorbed onto silica gel (18 g). Repeated column chromatographic purification provided porphyrin 21 (280 mg, 10%) as a purple solid: $^1$H NMR (300 MHz, CDCl$_3$) δ −2.94, −2.90, −2.84 (3s, 2H, atropisomer NH), 3.39-3.58 (multiple s, 12H, atropisomer N—CH$_3$), 7.50 (d, 4H), 7.71 (d, 4H), 8.92 (m, 8H).

2. [5,10,15,20-Tetrakis(1-methylimidazol-2-yl)porphyrinato]manganese(III) Chloride (22)

A solution of porphyrin 21 (29.9 mg, 0.047 mmol) and MnCl$_2$ (61 mg, 0.48 mmol) in DMF (12 mL) was heated at 120° C. for 14 h. The mixture was cooled to room temperature while exposed to a stream of air, and concentrated by rotary evaporation. Purification by column chromatography (CHCl$_3$/MeOH/concentrated NH$_4$OH/EtOAc) provided porphyrin 22 (12.5 mg, 37%) as a black solid: mp>300° C.; UV-vis $\lambda_{max}$=463.0 nm; $\epsilon$=9.35×10$^4$ L/cm-mol; API MS m/z=683 [C$_{36}$H$_{28}$MnN$_{12}$]$^+$.

3. 5,10,15,20-Tetrakis(1,3-dimethylimidazolium-2-yl)porphyrin Tetrachloride (23)

A solution of porphyrin 21 (589 mg, 0.934 mmol) and CH$_3$I (3 mL, 48 mmol) in DMF (10 mL) was heated in a sealed tube at 100° C. for 14 h. The reaction mixture was poured into ethyl acetate (200 mL) causing porphyrin 23 to precipitate as the iodide salt. The solution was filtered and the brown solid was washed with EtOAc and ether. The product was purified by column chromatography (CH$_3$CN/water/saturated KNO$_3$) and subjected to the double precipitation method to provide porphyrin 23 (540 mg, 69%) as a purple solid: $^1$H NMR (300 MHz, DMSO-d$_6$) δ −3.22 (s, 2H), 3.78 (s, 24H), 8.60 (s, 8H), 9.44 (s, 8H).

4. [5,10,15,20-Tetrakis(1,3-dimethylimidazolium-2-yl)porphyrinato]manganese(III) Pentachloride (24)

Porphyrin 23 (1.0 g, 0.83 mmol) was dissolved in MeOH (550 mL) then MnCl$_2$ (1.57 g, 12.5 mmol) was added. The solution pH was adjusted to pH=7.3 with 6N NaOH while bubbling a stream of air into the reaction mixture. The pH of the solution was maintained pH>7.3 for 1 h then adjusted to pH=4.5 with 1N HCl. The solution was filtered and the precipitate subjected to the double precipitation method and dried to provide porphyrin 24 (0.570 g, 74%) as a solid: mp>300° C.; UV-vis $\lambda_{max}$=460.5 nm; $\epsilon$=8.38×10$^4$ L/cm-mol; FAB MS m/z=778 [C$_{40}$H$_{40}$MnN$_{12}$]$^{+4}$.

VII. [5,15-Bis(4-carbomethoxyphenyl)-10,20-bis(1-methylimidazol-2-yl)-porphyrinato]manganese(III) Chloride (27) and [5,15-Bis(4-carbomethoxy-phenyl)-10,20-bis(1,3-dimethylimidazolium-2-yl)porphyrinato]manganese(III) Trichloride (29)

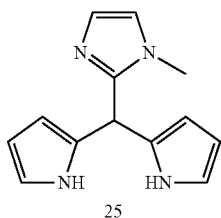

25

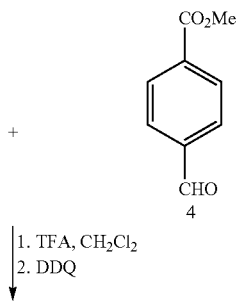

4

1. TFA, CH$_2$Cl$_2$
2. DDQ

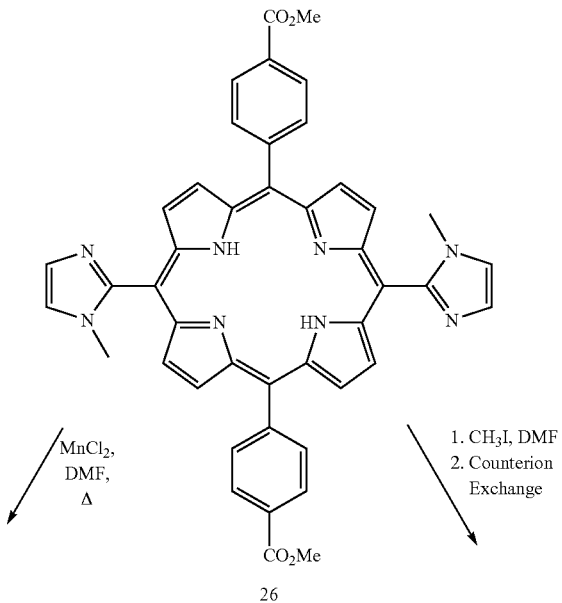

26

MnCl$_2$, DMF, Δ

1. CH$_3$I, DMF
2. Counterion Exchange

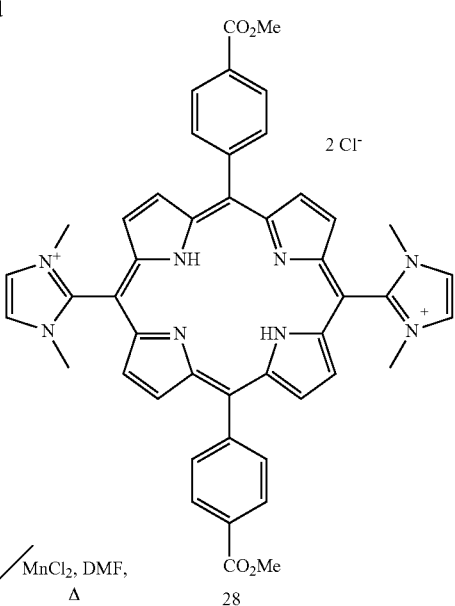

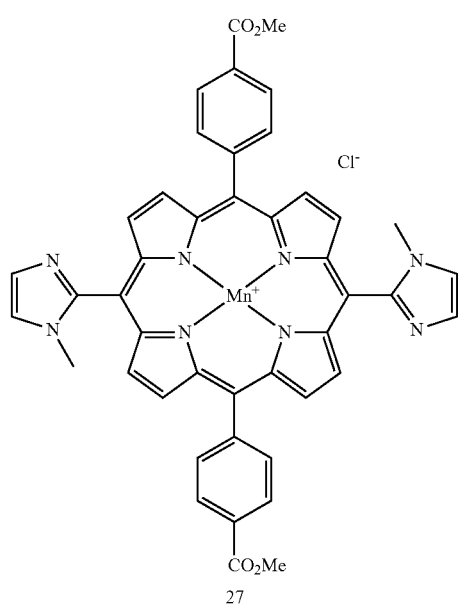

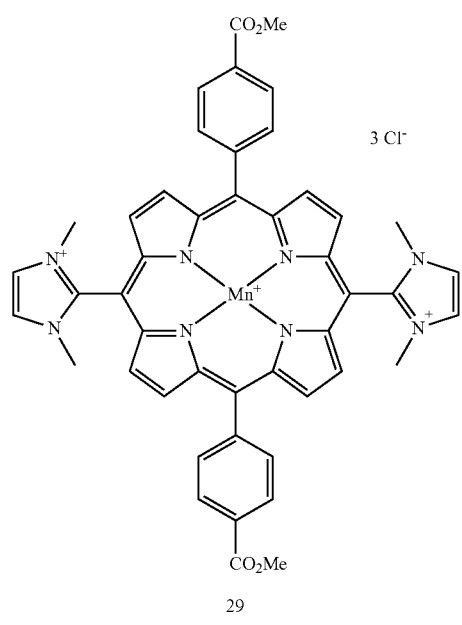

1. 5,15-Bis(4-carbomethoxyphenyl)-10,20-bis(1-methylimidazol-2-yl)porphyrin (26)

In a foil-covered 500-mL three-necked flask, equipped with a magnetic stirrer and $N_2$ inlet, was placed dipyrromethane 25 (0.71 g, 3.09 mmol), $CH_2Cl_2$ (310 mL), aldehyde 4 (50 mg, 3.09 mmol), and NaCl (22.4 mg, 0.35 mmol). The reaction mixture was stirred for 10 min, then TFA (1.48 mL, 19.2 mmol) was added. After a stirring period of 4 h at room temperature, DDQ (1.05 g, 4.65 mmol) was added. The reaction mixture was stirred overnight and the solvent was removed in vacuo. The residue was adsorbed onto silica gel (10 g) then purified by column chromatography (gradient elution 2-4% EtOAc/hexanes) to provide porphyrin 26 (220 g, 24%) as a purple solid: $^1$H NMR (300 MHz, $CDCl_3$) δ −2.85 (s, 2H), 3.43, 3.49 (2s, 6H, atropisomer $N-CH_3$), 4.14 (s, 6H), 7.49 (d, 2H), 7.68 (d, 2H), 8.30 (d, 4H), 8.48 (d, 4H), 8.87 (m, 8H).

2. 15,15-Bis(4-carbomethoxyphenyl)-10,20-bis(1-methylimidazol-2-yl)-porphyrinatolmanganese(III) Chloride (27)

A solution of porphyrin 26 (50.7 mg, 0.071 mmol) and $MnCl_2$ (88.6 mg, 0.70 mmol) in DMF (20 mL) was heated at 120° C. for 14 h. The mixture was cooled to room temperature while exposed to a stream of air, then concentrated by rotary evaporation. Purification by column chromatography (gradient elution 5-10% MeOH/$CH_2Cl_2$) provided porphyrin 27 (25 mg, 42%) as a black solid: mp>300° C.; UV-vis $\lambda_{max}$=463.0 nm; E=6.70×10$^4$ L/cm-mol; FAB MS m/z=791 $[C_{44}H_{32}MnN_8O_4]^+$.

3. 5,15-Bis(4-carbomethoxyphenyl)-10,20-bis(1,3-dimethylimidazolium-2-yl)-porphyrin Dichloride (28)

A solution of porphyrin 26 (80 mg, 0.11 mmol), DMF (7 mL) and CH$_3$I (0.150 mL) was stirred at room temperature for 4 h. The solvent was removed by rotary evaporation to give a dark colored residue. The residue was purified by column chromatography (CHCl$_3$/MeOH/concentrated NH$_4$OH/EtOAc) to provide porphyrin 28 (21 mg, 18%) as a purple solid: $^1$H NMR (300 MHz, DMSO-d$_6$) δ −3.02 (s, 2H), 3.73 (s, 12H), 4.08 (s, 6H), 8.45 (q, 8H), 8.56 (s, 4H), 9.13 (s, 8H); API MS m/z=384 [C$_{46}$H$_{40}$MnN$_8$O$_4$]$^{+2}$.

4. [5,15-Bis(4-carbomethoxyphenyl)-10,20-bis(1,3-dimethylimidazolium-2-yl)-porphyrinato]manganese (III) Trichloride (29)

A solution of porphyrin 28 (19.5 mg, 0.022 mmol) and MnCl$_2$ (22.4 mg, 0.18 mmol) in DMF (5 mL) was heated at 120° C. for 14 h. The reaction mixture was cooled to room temperature while exposed to a stream of air, then concentrated by rotary evaporation. Purification by column chromatography (CHCl$_3$/MeOH/concentrated NH$_4$OH/EtOAc) provided crude porphyrin 28. Purification by the double precipitation method and drying provided porphyrin 29 (6.5 mg, 37%) as a solid: mp>300° C.; UV-vis λ$_{max}$=447.5 nm; ε=1.27×10$^5$ L/cm-mol; FAB MS m/z=856 [C$_{46}$H$_{38}$MnN$_8$O$_4$]$^{+2}$.

VIII. [5,15-Bis(carboethoxy)-10,20-bis(1-methylimidazol-2-yl)porphyrinato]-manganese(III) Chloride (32)

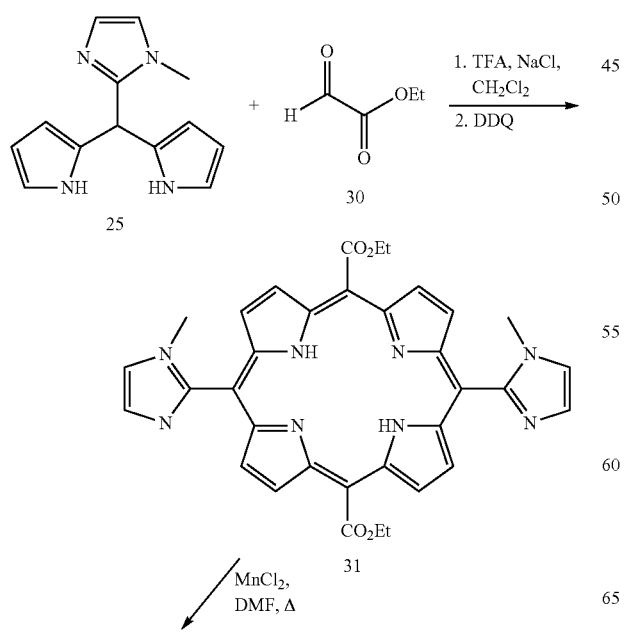

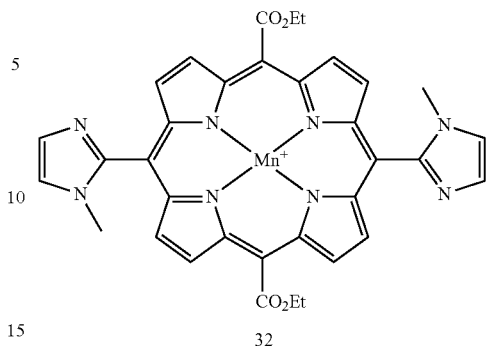

32

1. 5,15-Bis(carboethoxy)-10,20-bis(1-methylimidazol-2-yl)porphyrin (31).

In a foil-covered 500-mL three-necked flask, equipped with a magnetic stirrer and N$_2$ inlet, was placed dipyrromethane 25 (0.5 g, 2.2 mmol), CH$_2$Cl$_2$ (220 mL), and aldehyde 30 (225 mg, 2.2 mmol). The reaction mixture was stirred for 10 min, then TFA (1.0 mL, 12.9 mmol) was added. After a stirring period of 2 h at room temperature, DDQ (750 mg, 3.3 mmol) was added, and the reaction mixture was stirred overnight. Triethylamine (2.0 mL) was added, the solvent was evaporated in vacuo, and the residue adsorbed onto silica gel (10 g). Purification by column chromatography (5% EtOH/CHCl$_3$) provided porphyrin 31 (86 mg, 13%) as a purple solid: $^1$H NMR (300 MHz, CDCl$_3$) δ −3.08, −3.06 (2s, 2H, atropisomer NH), 1.82 (t, 6H), 3.40, 3.49 (2s, 6H, atropisomer N—CH$_3$), 5.11 (q, 4H), 7.53 (d, 2H), 7.72 (d, 2H), 8.94 (m, 4H), 9.50 (d, 4 H).

2. [5,15-Bis(carboethoxy)-10,20-bis(1-methylimidazol-2-yl)porphyrinato]-manganese(III) Chloride (32)

A solution of porphyrin 31 (27.7 mg, 0.045 mmol) and MnCl$_2$ (59.1 mg, 0.47 mmol) in DMF (12.5 mL) was heated at 120° C. for 14 h. Additional MnCl$_2$ (29 mg, 0.23 mmol) was added and the reaction mixture was heated for another 2 h. The reaction mixture was cooled to room temperature while exposed to a stream of air, then concentrated by rotary evaporation. Air was bubbled into a solution of the product dissolved in ethanol with two drops of 1N HCl. The solvent was evaporated in vacuo to give a dark colored residue. Purification by column chromatography (gradient elution 10-30% EtOH/CHCl$_3$) provided porphyrin 32 (6.5 mg, 35%) as a black solid: mp>300° C.; UV-vis λ$_{max}$=458.5 nm; ε=6.01× 10$^4$ L/cm-mol; API MS m/z 667 [C$_{34}$H$_{28}$MnN$_8$O$_4$]$^+$.

IX. [5,15-Bis(1-methylimidazol-2-yl)porphyrinato]manganese(III) Chloride (34) and [5,15-Bis(1,3-dimethylimidazolium-2-yl)porphyrinato]manganese(III) Trichloride (36)
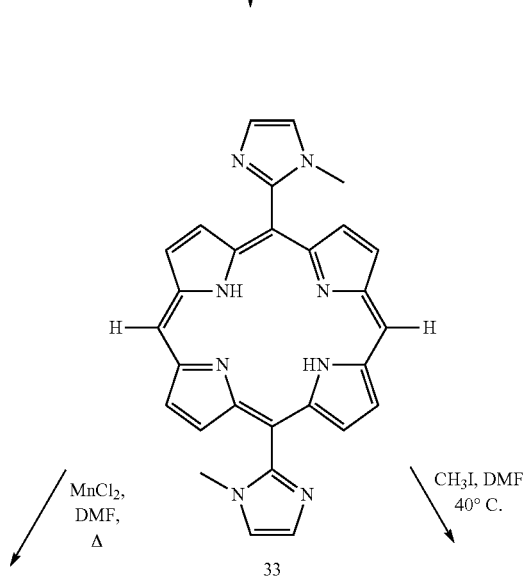
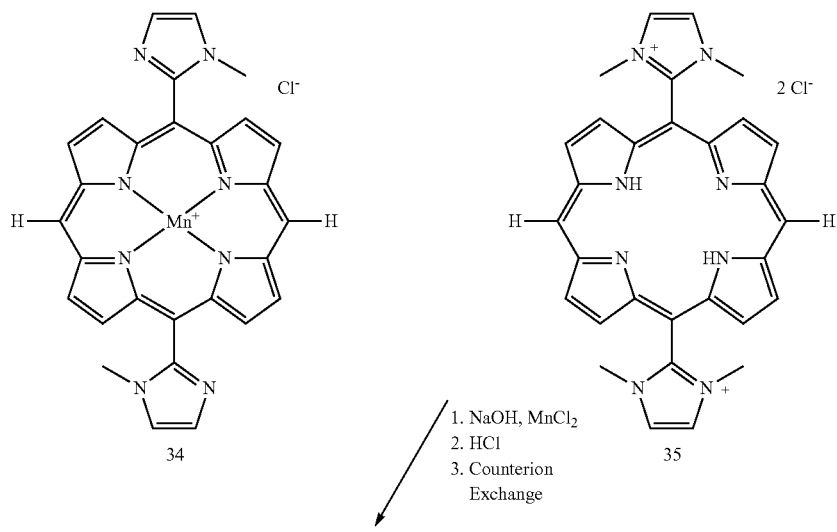

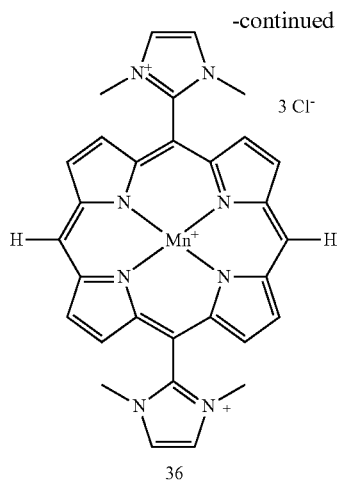

36

1. 5,15-Bis(1-methylimidazol-2-yl)porphyrin (33)

In a foil-covered 1-L three-necked flask, equipped with a magnetic stirrer and $N_2$ inlet, was placed dipyrromethane 10 (1.0 g, 6.84 mmol), $CH_2Cl_2$ (680 mL), and aldehyde 20 (753 mg, 6.84 mmol). The reaction mixture was stirred for 10 min, then TFA (3.1 mL, 40.2 mmol) was added. After a stirring period of 2 h at room temperature, DDQ (2.3 g, 10.1 mmol) was added and the reaction mixture was stirred overnight. Triethylamine (5.75 mL) was added into the reaction mixture, the solvent was evaporated in vacuo and the residue was adsorbed onto silica gel (15 g). Purification by column chromatography (6% $MeOH/CH_2Cl_2$) provided porphyrin 33 (0.120 g, 7%) as a purple solid: $^1H$ NMR (300 MHz, $CDCl_3$) δ −3.28 (s, 2H), 3.45, 3.52 (2s, 6H, atropisomer N—$CH_3$), 7.53 (d, 2H), 7.74 (d, 2H), 9.07 (m, 4H), 9.46 (d, 4H), 10.37 (s, 2H).

2. [5,15-Bis(1-methylimidazol-2-yl)porphyrinato]manganese(III) Chloride (34)

A solution of porphyrin 33 (50 mg, 0.106 mmol) and $MnCl_2$ (180 mg, 1.4 mmol) in DMF (20 mL) was heated at 120° C. for 14 h. The mixture was cooled to room temperature while exposed to a stream of air, then concentrated by rotary evaporation. Purification by column chromatography (33% $MeOH/CHCl_3$) provided porphyrin 34 (32 mg, 53%) as a black solid: mp>300° C.; UV-vis $\lambda_{max}$=454.5 nm; $\epsilon$=4.98× $10^4$ L/cm-mol; API MS m/z=523 $[C_{28}H_{20}MnN_8]^+$.

3. 5,15-Bis(1,3-dimethylimidazolium-2-yl)porphyrin Dichloride (35)

Porphyrin 33 (95 mg, 0.20 mmol) was dissolved in DMF (15 mL), $CH_3I$ (0.5 mL, 8.03 mmol) was added, and the reaction mixture stirred for 48 h. The DMF was evaporated in vacuo and the dark colored residue was purified by column chromatography (gradient elution 30% $MeOH/CH_2Cl_2$ to 6:4:1 $CHCl_3/MeOH/1N$ HCl) to provide porphyrin 35 (150 mg, 99%) as a purple solid: $^1H$ NMR (300 MHz, DMSO-$d_6$) δ −3.54 (s, 2H), 3.79 (s, 12H), 8.55 (s 4H), 9.28 (d, 4H), 11.00 (s, 2H).

4. [5,15-Bis(1,3-dimethylimidazolium-2-yl)porphyrinato]manganese(III) Trichloride (36)

Porphyrin 35 (150 mg, 0.198 mmol) was dissolved in water (50 mL) and the solution pH was adjusted to pH=12 with 6N NaOH. Manganese chloride (375 mg, 2.98 mmol) was added and the reaction mixture was stirred for 30 min. The solution was filtered on a fine fitted filter funnel, the pH of the filtrate was adjusted to pH=4 (1N HCl) and the solution was filtered. Purification of the solid filter cake by the double precipitation method and drying provided porphyrin 36 (25.5 mg, 20%) as a solid: mp>300° C.; UV-vis $\lambda_{max}$=447.5 nm; $\epsilon$=8.66×$10^4$ L/cm-mol; API MS m/z=554 $[C_{30}H_{26}MnN_8+H]^{+2}$.

X. [5,10,15,20-Tetrakis(1,4,5-trimethylimidazol-2-yl)porphyrinato]-manganese(III) Chloride (39) and [5,10,15,20-Tetrakis(1,3,4,5-tetramethyl-imidazolium-2-yl)porphyrinato]manganese(III) Pentachloride (41)

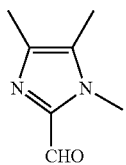 + 

37

↓ Propionic acid

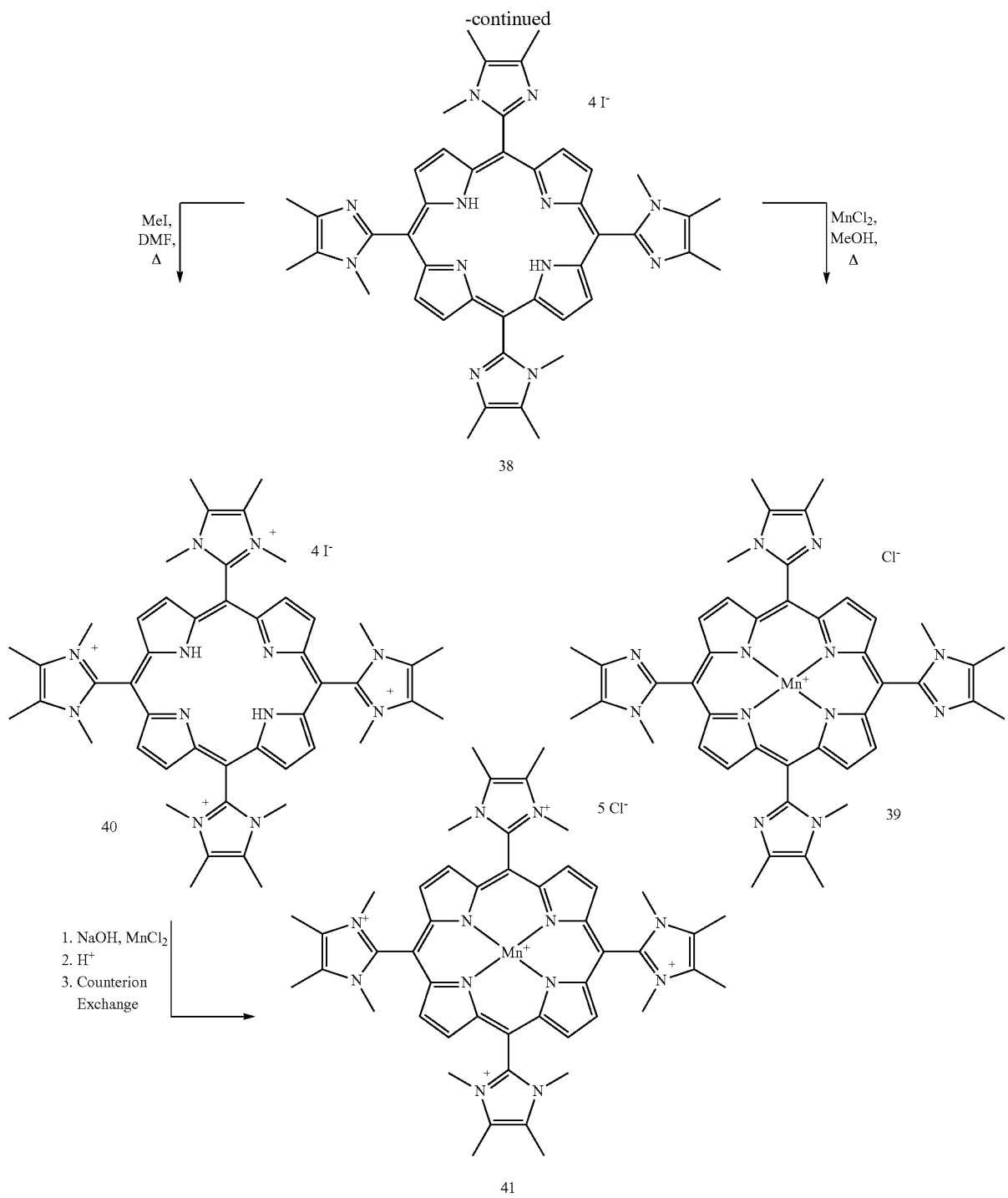

1. [5,10,15,20-Tetrakis(1,4,5-trimethylimidazol-2-yl) porphyrin (38)

1,4,5-Trimethylimidazole-2-carboxaldehyde (37, 750 mg, 5.42 mmol), prepared according to literature procedure (Alcalde, E. et al., Tetrahedron 52:15171-15188 (1996)), was dissolved in propionic acid (120 mL) in a 250 mL three neck round-bottom flask equipped with a thermometer and a condenser. The solution was heated to reflux then pyrrole (0.38 mL, 5.42 mmol) was added. The reaction mixture was heated at reflux for an additional 5 h, then cooled to room temperature while exposed to air overnight. The propionic acid was removed by vacuum distillation yielding a dark solid residue which was adsorbed onto silica gel. Purification by column chromatography (gradient elution 5-10% MeOH/$CH_2Cl_2$) provided porphyrin 38 as a mixture of atropisomers (108 mg, 10.7%). $^1$H NMR (300 MHz, $CDCl_3$)*−2.90, −2.85, −2.78 (3s, 2H, atropisomer NH), 2.50 (s, 12H), 2.57 (s, 12H), 3.15-3.42 (multiple s, 12H, atropisomer N—$CH_3$), 8.91 (multiple s, 8H, atropisomer).

2. [5,10,15,20-Tetrakis(1,4,5-trimethylimidazol-2-yl) porphyrinato]manganese(III) Chloride (39)

Porphyrin 38 (40 mg, 0.05 mmol) was dissolved in MeOH (7 mL) in a 25 mL round-bottom flask equipped with a condenser. Manganese(II) chloride (101 mg, 0.81 mmol) was added and the reaction mixture was heated under reflux for 2 h. Air was bubbled into the reaction mixture for 20 min then methanol was evaporated in vacuo. Purification of the residue by column chromatography provided porphyrin 39 as a black solid (12 mg, 27%): mp>300° C.; UV-vis $8_{max}$=474.5 nm, =9.74×10$^4$ L/cm-mol; API MS m/z=795[$C_{44}H_{44}MnN_{12}$]$^+$.

3. [5,10,15,20-Tetrakis(1,3,4,5-tetramethylimidazolium-2-yl)porphyrin Tetraiodide (40)

Porphyrin 38 (40 mg, 0.05 mmol) was dissolved in DMF (5 mL) in a sealed tube reactor. Methyl iodide (1 mL, 16 mmol) was added and the sealed tube heated at 60° C. overnight. Dilution of the reaction mixture with EtOAc (100 mL) resulted in the precipitation of crude product 40 which was collected by vacuum filtration then purified by column chromatography to provide porphyrin 40 as a dark purple solid (25 mg, 35%): $^1$H NMR (300 MHz, DMSO-$d_6$)*–3.20 (s, 2H), 2.72 (s, 24H), 3.58 (s, 24H), 9.40 (s, 8H).

4. [5,10,15,20-Tetrakis(1,3,4,5-tetramethylimidazolium-2-yl)porphyrinato]-manganese(III) Pentachloride (41)

Porphyrin 40 (25 mg, 0.02 mmol) was dissolved in methanol (7 mL) in a round-bottomed flask (25 mL). Manganese(II) chloride (50 mg, 0.4 mmol) was added and the reaction mixture was heated at 60° C. for 6 h. NaOH (2N, 2 drops) was added and the reaction mixture stirred for an additional hour. The reaction mixture was filtered through celite and washed through with MeOH. Analysis of the filtrate by UV-vis spectroscopy indicated that the reaction was incomplete. The solvent was evaporated off and the residue redissolved in MeOH (7 mL), then MnCl$_2$ (50 mg, 0.4 mmol) was added and the reaction mixture was heated at 60° C. for 3 h. Air was bubbled into the reaction mixture for 20 min. The reaction mixture was filtered over celite and washed with MeOH. Evaporation of the solvents in vacuo provided a brown residue. Purification of the product by the double precipitation method provided porphyrin 41 (10 mg, 51%) as a brown solid: mp>300° C.; UV-vis $8_{max}$=451.5 nm, =9.29×10$^4$ L/cm-mol.

XI. [5,10,15,20-Tetrakis(4-methyl-1,2,4-triazol-3-yl) porphyrinato]manganese(III) Chloride (44)

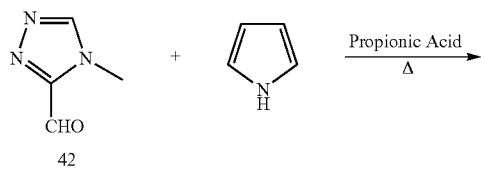

1. 5,10,15,20-Tetrakis(4-methyl-1,2,4-triazol-3-yl) porphyrin (43)

4-Methyl-1,2,4-triazole-2-carboxaldehyde (42, 1.06 g, 9.5 mmol), prepared according to literature procedure (Moderhack, D.; Hoppe-Tichy, T. *J. Prakt. Chem./Chem-Ztg.* 1996, 338(2), 169-171), was dissolved in propionic acid (180 mL) in a 250-mL three-neck round bottom flask covered with foil and equipped with a condenser. The solution was heated to reflux, and then pyrrole (0.66 mL, 9.5 mmol) was added. The reaction mixture was stirred at reflux for an additional 2.5 h. The reaction was then cooled to room temperature while exposed to air over 2 days. Evaporation of the propionic acid under reduced pressure provided a dark residue which was adsorbed onto silica gel. Repeated purification by column chromatography (gradient elution, CHCl$_3$, MeOH, concentrated NH$_4$OH, EtOAc) provided porphyrin 43 (219 mg, 14.6%) as a solid mixture of atropiosomers: $^1$H NMR (300

MHz, DMSO-$d_6$) δ −3.36, −3.13, −3.09 (3s, 2H, atropisomer NH), 3.43-3.64 (multiple s, 12H, atropisomer N—$CH_3$), 9.03 (broad s, 8H), 9.20 (s, 4H).

2. [5,10,15,20-Tetrakis(4-methyl-1,2,4-triazol-3-yl)porphyrinato]manganese(III) Chloride (44)

Porphyrin 43 (77 mg, 0.12 mmol) was dissolved in DMF (30 mL) in a 100-mL round bottom flask equipped with a condenser. Manganese(II) chloride (156 mg, 1.24 mmol) was added and the reaction was heated at 130° C. overnight. The reaction mixture was exposed to a stream of air as it cooled to room temperature. The porphyrin precipitated out upon the addition of $CH_2Cl_2$ (5-10 mL). The solids were filtered and washed with EtOH and $CH_2Cl_2$ to provide porphyrin 44 (45 mg, 51%) as a brown solid: mp>300° C.; UV-vis $\lambda_{max}$=452.5 nm; $\epsilon$=8.10×10$^4$ L/cm-mol; FAB-MS m/z=787 $[C_{32}H_{24}MnN_{18}]^+$.

XII. [5,15-Bis(trifluoromethyl)-10,20-bis(imidazol-2-yl)porphyrinato]-manganese(III) Chloride (47)

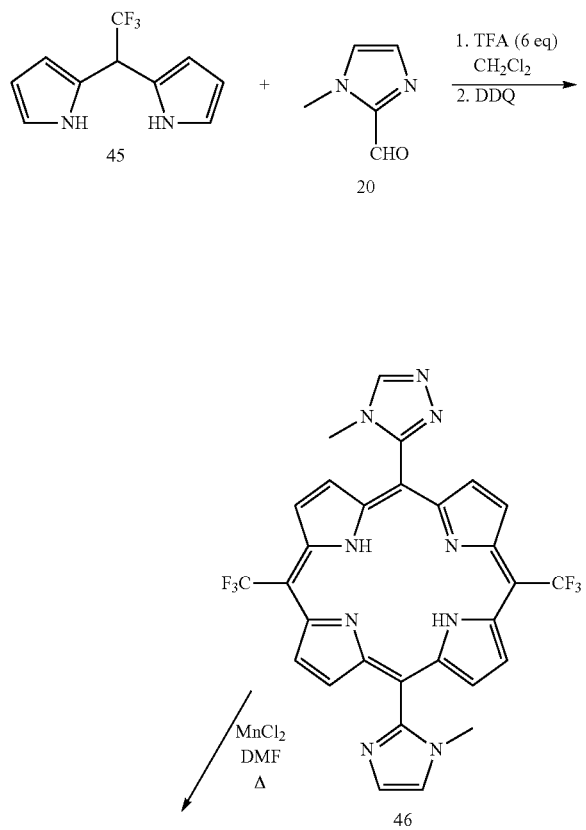

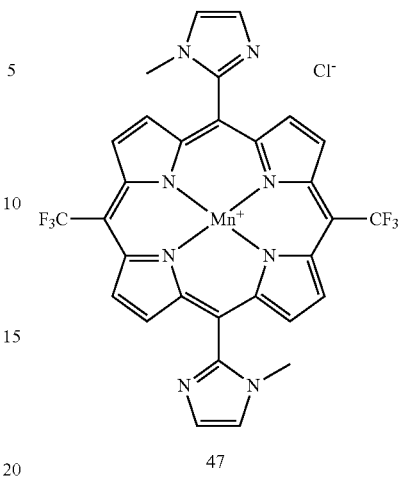

1. 5,15-Bis(trifluoromethyl)-10,20-bis(imidazol-2-yl)porphyrin (46)

In a foil-covered 1-L three-neck round bottom flask, equipped with a magnetic stirrer and a $N_2$ outlet, was added dipyrromethane 45 (1.13 g, 5.28 mmol), 1-methylimidazole-2-carboxaldehyde (20, 582 mg, 5.28 mmol), sodium chloride (32 mg, 0.54 mmol) and $CH_2Cl_2$ (530 mL). The reaction mixture was stirred for 10 min, then TFA (2.40 mL, 31.1 mmol) was added. After a stirring period of 105 min, DDQ (1.81 g, 7.97 mmol) was added, and the mixture was stirred overnight. The solvent was removed by rotary evaporation, and the crude residue was adsorbed onto silica gel (3 g). Purification by column chromatography (gradient elution, 5-10% MeOH/$CH_2Cl_2$) provided porphyrin 46 (455 mg, 34%) as a black solid: $^1$H NMR (300 MHz, CDCl$_3$) δ −2.87 (s, 2H), 3.56 (m, 6H), 7.85 (d, 2H), 8.05 (d, 2H), 8.99 (m, 4H), 9.81 (m, 4H); API-MS m/z=607 $[C_{30}H_{20}F_6N_8+H]^+$.

2. [5,15-Bis(trifluoromethyl)-10,20-bis(imidazol-2-yl)porphyrinato]manganese(III) Chloride (47)

A solution of free porphyrin 46 (113 mg, 0.186 mmol) and MnCl$_2$ (360 mg, 2.86 mmol) in DMF (15 mL) was warmed to 120° C. for 6 h. The mixture was cooled to room temperature while exposed to a stream of air, then concentrated by rotary evaporation. The crude residue was dissolved in 10% MeOH/$CH_2Cl_2$ (100 mL), then adsorbed onto silica gel (1 g). Purification by column chromatography (10% MeOH/$CH_2Cl_2$) provided porphyrin 47 (45 mg, 35%) as a dark green solid: mp>300° C.; UV-vis $\lambda_{max}$=456.5 nm; $\epsilon$=1.98×10$^4$ L/cm-mol; API-MS m/z=659 $[C_{30}H_{18}F_6MnN_8]^+$.

XIII. [5,10,15,20-Tetrakis(1-methylpyrazol-4-yl)porphyrinato]manganese(III) Chloride (50) and [5,10,15,20-Tetrakis(1,2-dimethylpyrazolium-4-yl)porphyrinato]-manganese(III) Pentachloride (52)
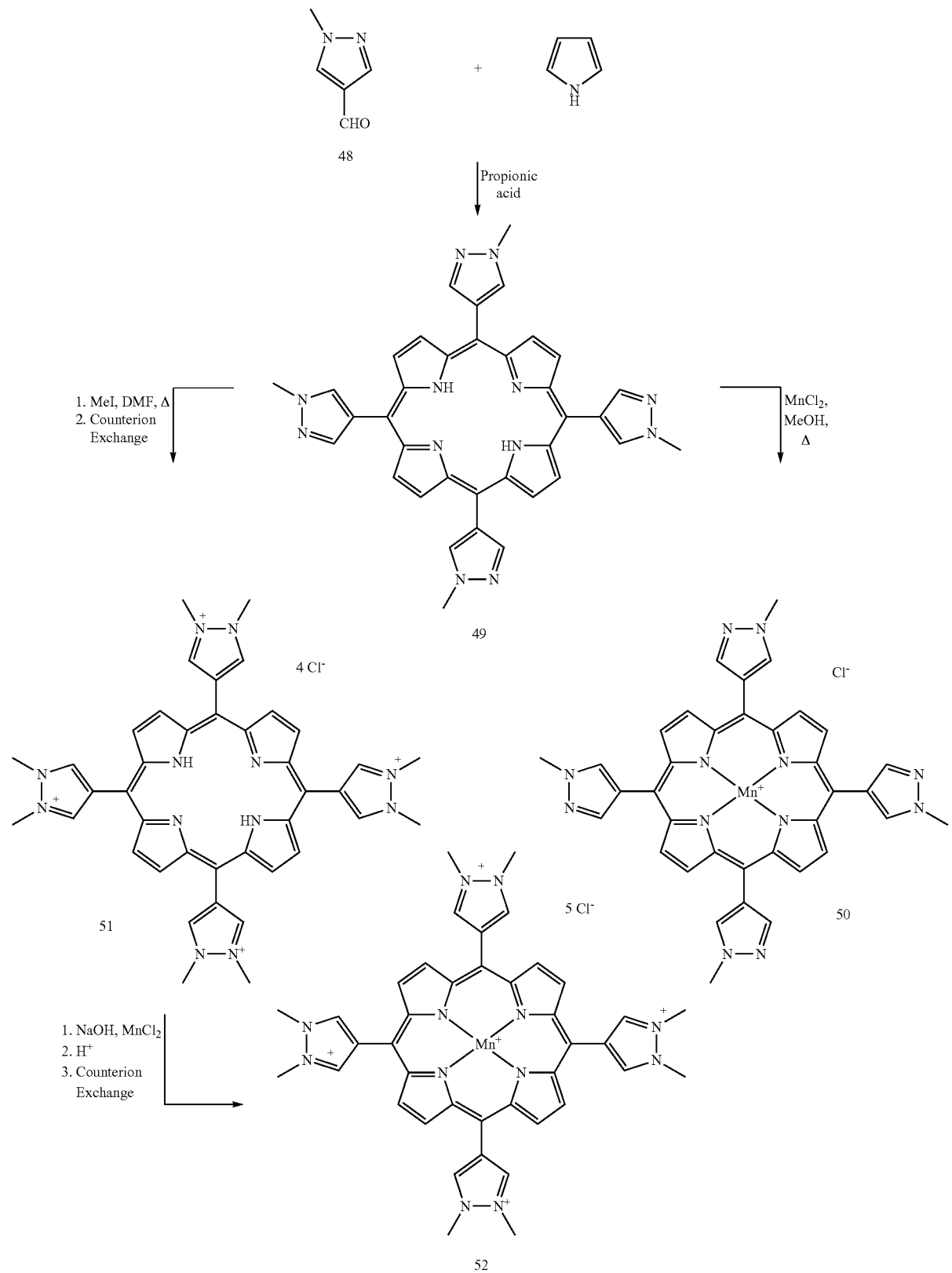

1. 5,10,15,20-Tetrakis(1-methylpyrazol-4-yl)porphyrin (49)

To a refluxing solution of propionic acid (200 mL) and 1-methylpyrazole-4-carboxaldehyde (48, 0.92 g, 8.32 mmol), prepared according to literature procedure (Finar, I. L.; Lord, G. H. *J. Chem. Soc.* 1957, 3314-3315), was added pyrrole (0.63 mL, 8.32 mmol). The reaction was covered with foil and was heated under reflux for 3.5 h. Upon cooling the reaction mixture was exposed to air overnight. The propionic acid was then removed by vacuum distillation. The crude residue was dissolved in 5% MeOH/CH$_2$Cl$_2$, then adsorbed onto silica gel (5.3 g). Purification by column chromatography (5% MeOH/CH$_2$Cl$_2$) provided porphyrin 49 as a purple solid (231 mg, 17.5%): $^1$H NMR (300 MHz, DMSO-d$_6$) δ −2.74 (s, 2H), 4.28 (s, 12H), 8.31 (s, 4H), 8.67 (s, 4H), 9.16 (s, 8H).

2. [5,10,15,20-Tetrakis(1-methylpyrazol-4-yl)porphyrinato]manganese(III) Chloride (50)

Porphyrin 49 (50 mg, 7.93×10$^{-2}$ mmol) was dissolved in DMF (10 mL) in a 25-mL round bottom flask equipped with a condenser. Manganese (II) chloride (150 mg, 1.19 mmol) was added and the reaction was heated at 125° C. for 4 h. A stream of air was introduced and the reaction heated for an additional 2 h. The reaction was diluted with EtOAc (100 mL) and the crude product was collected by vacuum filtration. Purification of the residue by column chromatography (10% MeOH/CH$_2$Cl$_2$) followed by counterion exchange provided porphyrin 50 as a green solid (15 mg, 25%): mp>300° C.; UV-vis $\lambda_{max}$=471.0 nm, s=9.55×10$^4$ L/cm-mol; API MS m/z=683 [C$_{36}$H$_{28}$MnN$_{12}$]$^+$.

3. 5,10,15,20-Tetrakis(1,2-dimethylpyrazolium-4-yl)porphyrin Tetrachloride (51)

Porphyrin 49 (200 mg, 0.32 mmol) was dissolved in DMF (15 mL) in a sealed tube reactor. Methyl iodide (2 mL, 32 mmol) was added and the sealed tube heated at 125° C. for 6 h. Dilution of the reaction mixture with EtOAc resulted in the precipitation of crude product which was collected by vacuum filtration and initially purified by column chromatography (8:1:1 CH$_3$CN/water/saturated KNO$_3$). Further purification by the double precipitation method provided porphyrin 51 as a dark purple solid (45 mg, 17%): $^1$H NMR (300 MHz, DMSO-d$_6$) δ −3.16 (s, 2H), 4.55 (s, 24H), 9.45 (s, 8H), 9.50 (s, 8H).

4. [5,10,15,20-Tetrakis(1,2-dimethylpyrazolium-4-yl)porphyrinato]manganese(III) Pentachloride (52)

Porphyrin 51 (40 mg, 4.80×10$^{-2}$ mmol) was dissolved in water (10 mL) Manganese (II) chloride (90 mg, 0.72 mmol) was added and the reaction was heated at 50° C. Analysis of the reaction mixture by UV-vis spectroscopy showed incomplete reaction. Additional MnCl$_2$ (210 mg, 1.67 mmol) was added and heating of the reaction mixture was continued until completion of reaction was indicated by UV-vis analysis. Filtration followed by purification of the product by the double precipitation method provided porphyrin 52 (25 mg, 57%) as a brown solid: mp>300° C.; UV-vis $\lambda_{max}$=461.0 nm, ε=7.82×10$^4$ L/cm-mol; API MS m/z=683 [C$_{40}$H$_{40}$MnN$_{12}$-4CH$_3$]$^+$.

XIV. [5,10,15,20-Tetrakis(1,3-dimethylimidazolium-5-yl)porphyrinato]manganese(III) Pentachloride (56)

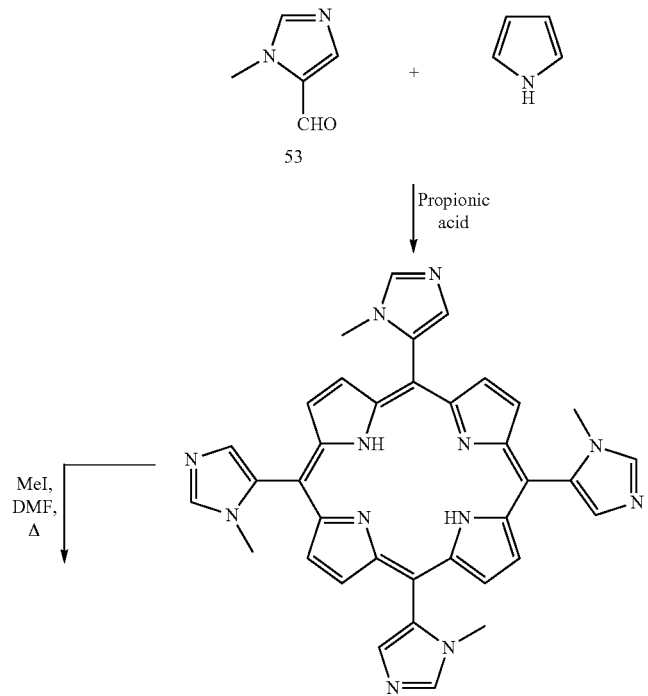

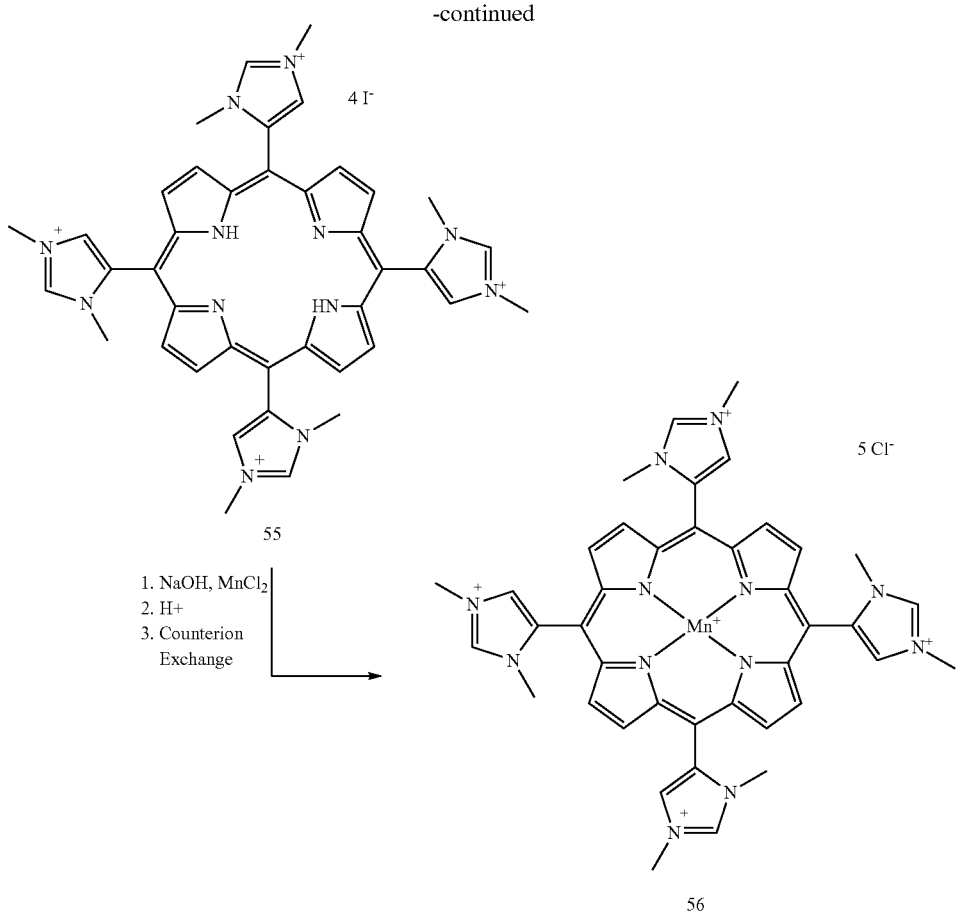

1. 5,10,15,20-Tetrakis(1-methylimidazol-5-yl)porphyrin (54)

To a refluxing solution of propionic acid (400 mL) and 1-methylimidazole-5-carboxaldehyde (53, 2.0 g, 18.16 mmol), prepared according to literature procedure (Dener, J. M.; Zhang, L-H.; Rapoport, H. *J. Org. Chem.* 1993, 58, 1159-1166), was added pyrrole (1.26 mL, 18.16 mmol). The reaction was covered with foil then heated under reflux for 5 h. Upon cooling, the reaction mixture was exposed to air for 60 h. The propionic acid was then removed by vacuum distillation. The residue was dissolved in 10% MeOH/CH$_2$Cl$_2$, then adsorbed onto silica gel (6 g). Purification by column chromatography (gradient elution, 5-10% MeOH/CH$_2$Cl$_2$) provided porphyrin 54 as a purple solid (600 mg, 21%): $^1$H NMR (300 MHz, CDCl$_3$) δ −2.80, −2.75 (2s, 2H, atropisomer NH), 3.42-3.58 (multiple s, 12H, atropisomer N—CH$_3$), 7.87-7.98 (multiple s, 4H, atropisomer), 8.06 (s, 4H), 8.95-8.99 (multiple s, 8H, atropisomer).

2. 5,10,15,20-Tetrakis(1,3-dimethylimidazolium-5-yl)porphyrin Tetraiodide (55)

Porphyrin 54 (395 mg, 0.63 mmol) was dissolved in DMF (15 mL) in a sealed tube reactor. Methyl iodide (2 mL, 32 mmol) was added and the sealed tube was heated at 100° C. overnight. Dilution of the reaction mixture with EtOAc (200 mL) resulted in the precipitation of the crude product which was collected by vacuum filtration. Purification by column chromatography (8:1:1 CH$_3$CN/water/saturated KNO$_3$) provided porphyrin 55 (250 mg, 33%) as a dark purple solid: $^1$H NMR (300 MHz, DMSO-d$_6$) δ −3.25 (s, 2H), 3.46-3.64 (multiple s, 12H, atropisomer), 4.30 (s, 12H), 8.68 (s, 4H), 9.48 (s, 8H), 9.78 (s, 4H).

3. [5,10,15,20-Tetrakis(1,3-dimethylimidazolium-5-yl)porphyrinato]-manganese(III) Pentachloride (56)

Porphyrin 55 (200 mg, 0.17 mmol) was dissolved in methanol (100 mL) Manganese (II) chloride (315 mg, 2.50 mmol) was added and an air stream introduced into the reaction mixture. The pH of the solution was maintained at 8 by the dropwise addition of 6N NaOH over the period of the reaction, after which time the pH was adjusted to 5 with 6N HCl. The reaction was filtered on a fritted funnel. Purification of the product by the double precipitation method provided porphyrin 56 (63 mg, 41%) as a brown solid: mp>300° C.; UV-vis λ$_{max}$ 454.0 nm, ε=1.23×10$^5$ L/cm-mol.

XV. [5,15-Bis(4-fluorophenyl)-10,20-bis(1-methylimidazol-2-yl)porphyrinato]-manganese(III) Chloride (59) and [5,15-Bis(4-fluorophenyl)-10,20-bis(1,3-dimethylimidazolium-2-yl)porphyrinato]manganese(III) Trichloride (61)
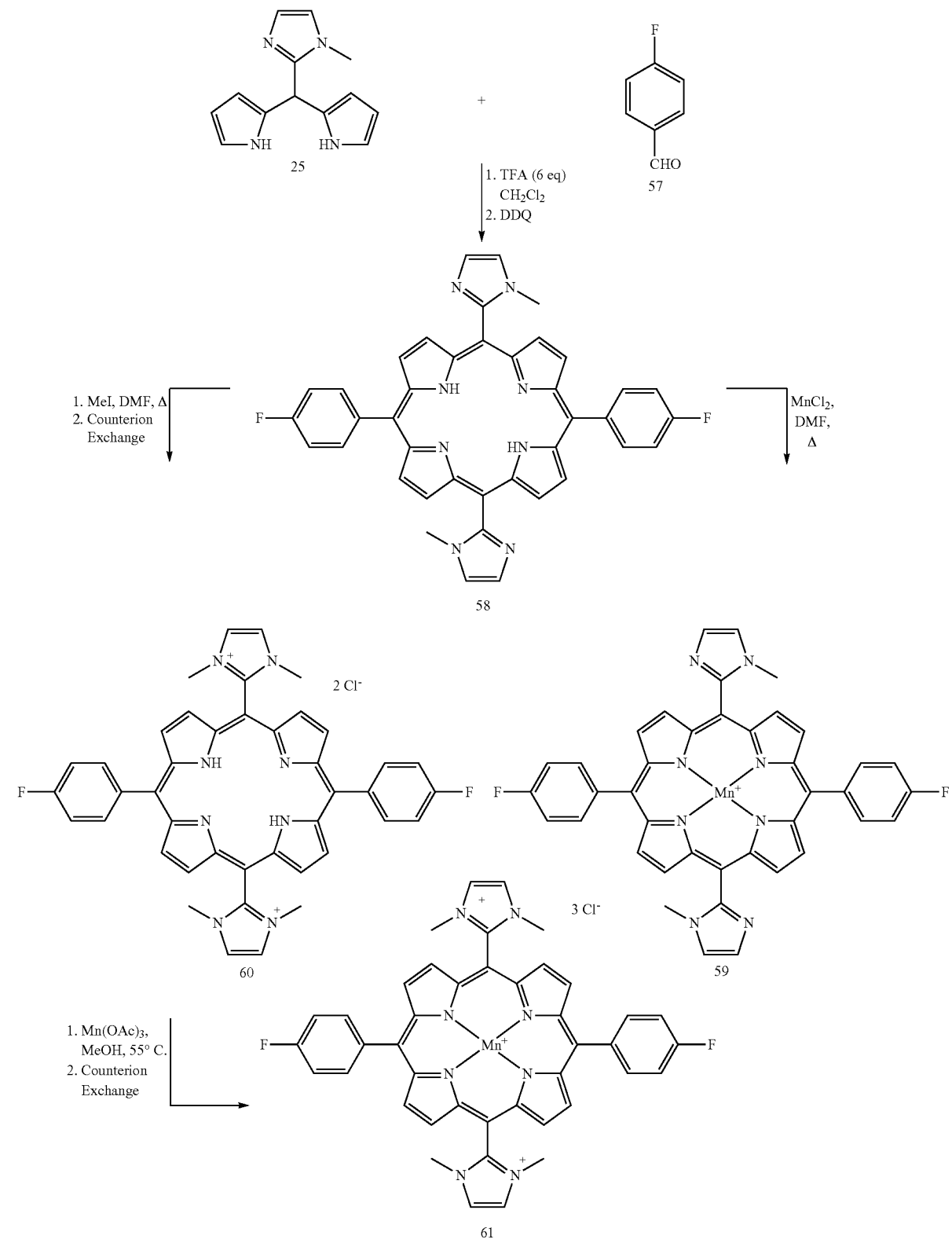

1. 5,15-Bis(4-fluorophenyl)-10,20-bis(1-methylimidazol-2-yl)porphyrin (58)

In a foil-covered 1-L three-neck round bottom flask, equipped with a magnetic stirrer and a $N_2$ outlet, was added dipyrromethane 25 (1.00 g, 4.43 mmol), 4-fluoro-benzaldehyde (57, 550 mg, 4.43 mmol), sodium chloride (30 mg, 0.5 mmol) and $CH_2Cl_2$ (450 mL). The reaction mixture was stirred for 10 min, then TFA (2.0 mL, 26 mmol) was added. After a stirring period of 105 min, DDQ (1.51 g, 6.65 mmol) was added, and the mixture was stirred overnight. The solvent was removed by rotary evaporation, and the crude residue was adsorbed onto silica gel (3 g). Purification by column chromatography (gradient elution, 5-10% MeOH/$CH_2Cl_2$) provided porphyrin 58 (229 mg, 16%) as a black solid: $^1$H NMR (300 MHz, DMSO-$d_6$) δ −3.05 (s, 2H), 3.70, 3.72 (2s, 6H, atropisomer N—$CH_3$), 7.73 (m, 8H), 8.19 (s, 2H), 8.30 (m, 4H), 9.02 (m, 6H); API-MS m/z=659 $[C_{40}H_{28}F_2N_8+H]^+$.

2. [5,15-Bis(4-fluorophenyl)-10,20-bis(1-methylimidazol-2-yl)porphyrinato]-manganese(III) Chloride (59)

Porphyrin 58 (85 mg, 0.13 mmol) was dissolved in DMF (7 mL) in a 50-mL round bottom flask equipped with a condenser. Manganese (II) chloride (215 mg, 1.71 mmol) was added and the reaction was heated at 120° C. for 3.5 h. The reaction was cooled to room temperature then concentrated by rotary evaporation. The crude residue was dissolved in 20% MeOH/$CH_2Cl_2$ (100 mL) and adsorbed onto silica gel (2 g). Purification by column chromatography (gradient elution, 3-8% MeOH/$CH_2Cl_2$) provided porphryin 59 as a green solid (15 mg, 16%): mp>300° C.; UV-vis $\lambda_{max}$=463.0 nm, $\epsilon$=4.05×$10^4$ L/cm-mol; API MS m/z=711 $[C_{40}H_{26}F_2MnN_8]^+$.

3. 5,15-Bis(4-fluorophenyl)-10,20-bis(1,3-imidazolium-2-yl)porphyrin Dichloride (60)

Porphyrin 58 (170 mg, 0.26 mmol) was dissolved in DMF (7 mL) in a sealed tube reactor. Methyl iodide (6 mL, 96 mmol) was added and the sealed tube was heated at 100° C. overnight. The mixture was cooled to room temperature and concentrated by rotary evaporation. The residue was precipitated as the chloride salt from acetone by the addition of $Bu_4NCl$ solution in acetone (0.3 g/mL). The solid was collected on a fitted funnel, washed with copious quantities of acetone, and dried under vacuum at room temperature to provide porphyrin 60 as a dark purple solid (196 mg). The product was used without further purification.

4. [5,15-Bis(4-fluorophenyl)-10,20-bis(1,3-dimethylimidazolium-2-yl)porphyrinato]manganese(III) Trichloride (61)

Porphyrin 60 (196 mg, est. 0.26 mmol) dissolved in MeOH (30 mL) was slowly warmed to 55° C. then $Mn(OAc)_3.2 H_2O$ (694 mg, 2.59 mmol) was added. After a stirring period of 3 h, the mixture was cooled to room temperature, filtered through Celite and concentrated by rotary evaporation. The residue was purified by the double precipitation method to provide porphyrin 61 (102 mg, 46% over two steps) as a dark green solid: mp>300° C., UV-vis $\lambda_{max}$=458.0 nm; $\epsilon$=1.30×$10^4$ L/cm-mol; ES-MS m/z=967 $[(C_{42}H_{32}F_2MnN_8)^{+3}+2(CF_3CO_2)]^+$.

XVI. [5,10,15,20-Tetrakis(1,3-diethylimidazolium-2-yl)porphyrinato]manganese(III) Pentachloride (65)

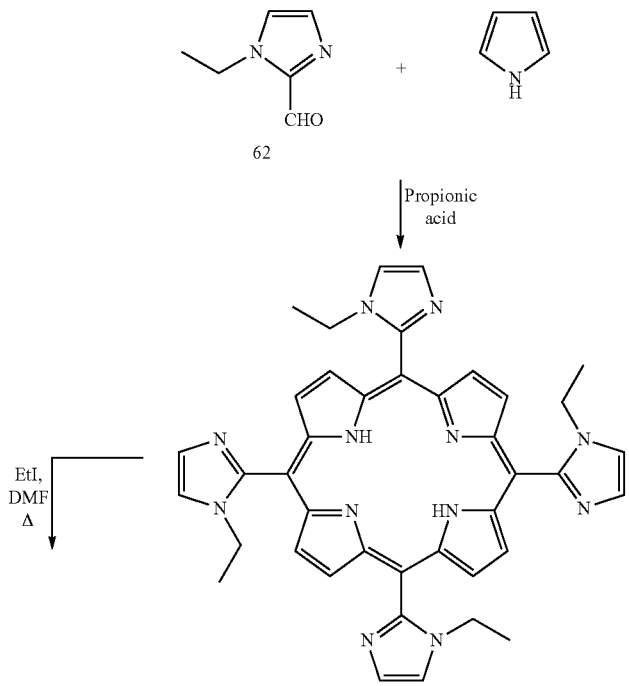

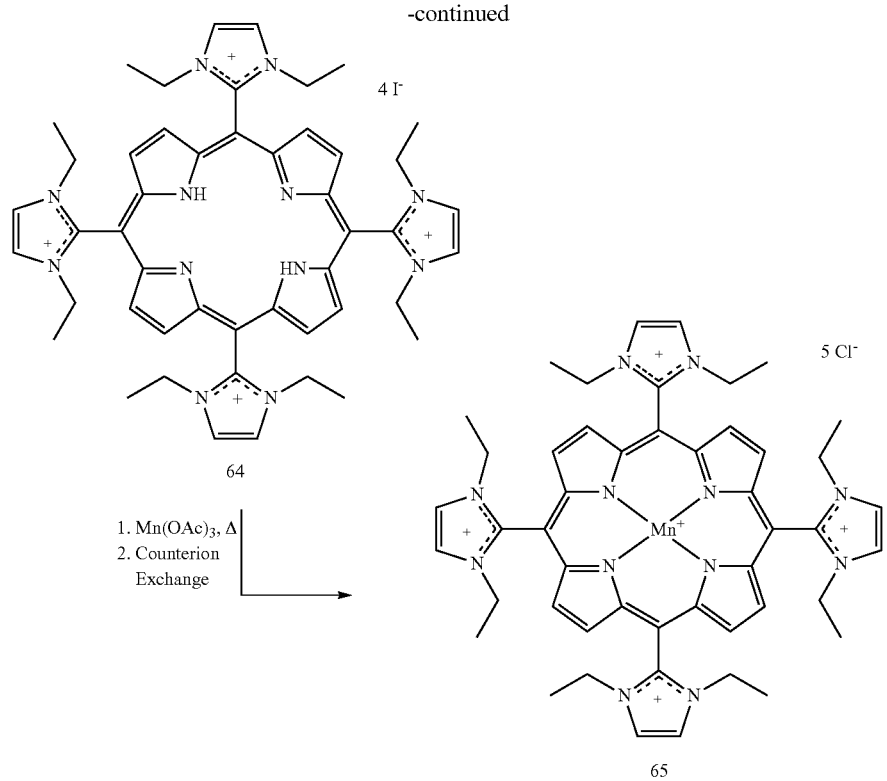

64

1. Mn(OAc)$_3$, Δ
2. Counterion Exchange

65

1. 5,10,15,20-Tetrakis(1-ethylimidazol-2-yl)porphyrin (63)

To a refluxing solution of propionic acid (450 mL) and 1-ethylimidazole-2-carboxaldehyde (62, 2.5 g, 20.0 mmol, prepared in a similar manner as the methyl imidazole derivative 20) was added pyrrole (1.40 mL, 20.0 mmol). The reaction was covered in foil then heated under reflux for 5 h. Upon cooling, the reaction mixture was exposed to air overnight. The propionic acid was then removed by vacuum distillation. Repeated purification by column chromatography (gradient elution, CHCl$_3$/MeOH/concentrated NH$_4$OH/EtOAc) provided porphyrin 63 as a purple solid (281 mg, 8.1%): $^1$H NMR (300 MHz, CDCl$_3$) δ −2.95, −2.90, −2.87 (3s, 2H, atropisomer NH), 0.85-1.25 (multiple t, 12H, atropisomer CH$_3$), 3.61-3.88 (multiple q, 8H, atropisomer CH$_2$), 7.55 (d, 4H), 7.70 (d, 4H), 8.98 (multiple s, 8H, atropisomer).

2. 5,10,15,20-Tetrakis(1,3-diethylimidazolium-2-yl) porphyrin Tetraiodide (64)

Porphyrin 63 (106 mg, 0.15 mmol) was dissolved in DMF (5 mL) in a sealed tube reactor. Ethyl iodide (2.0 mL, 25 mmol) was added and the sealed tube was heated at 65° C. for 6 h. Dilution of the reaction mixture with EtOAc (100 mL) resulted in the precipitation of the crude product which was collected by vacuum filtration, washed with chloroform and then purified by column chromatography (8:1:1 CH$_3$CN/water/saturated KNO$_3$) to provide porphyrin 63 (140 mg, 69%) as a dark purple solid: $^1$H NMR (300 MHz, DMSO-d$_6$) δ −3.22 (s, 2H), 1.17 (t, 24H), 4.01 (s, 16H), 8.70 (s, 8H), 9.43 (s, 8H):

3. [5,10,15,20-Tetrakis(1,3-diethylimidazolium-2-yl) porphyrinato]-manganese(III) Pentachloride (65)

Porphyrin 64 (106 mg, 8.09×10$^{-2}$ mmol) was dissolved in methanol (15 mL) then Mn(OAc)$_3$.2 H$_2$O (216 mg, 0.81 mmol) was added and the reaction heated at 55° C. for 2.5 h. The reaction was filtered through celite and then evaporated in vacuo. Purification of the product by the double precipitation method provided porphyrin 65 (65 mg, 78%) as a brown solid: mp>300° C., UV-vis λ$_{max}$=446.5 nm, ε=1.35×10$^5$ L/cm-mol; ES-MS m/z=1307 [(C$_{48}$H$_{56}$MnN$_{12}$)$^{+5}$+4 (CF$_3$CO$_2^-$)]$^+$.

XVII. [5,10,15,20-Tetrakis(1-ethyl-3-methylimidazolium-2-yl)porphyrinato]-manganese(III) Pentachloride (67)

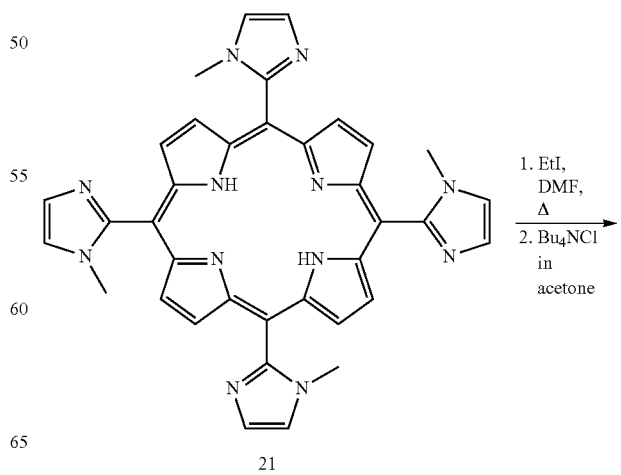

21

1. EtI, DMF, Δ
2. Bu$_4$NCl in acetone

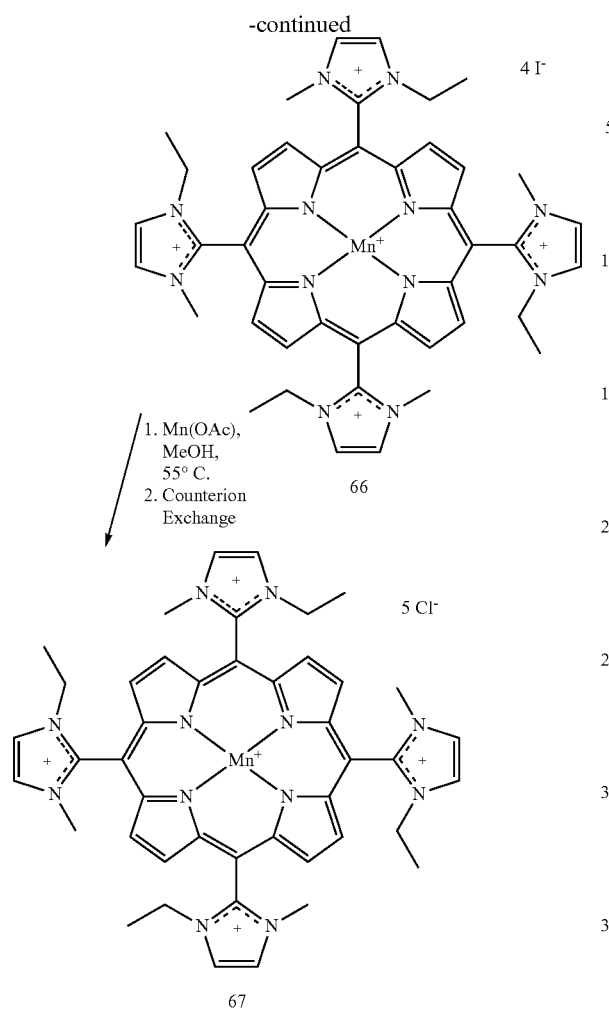

1. 5,10,15,20-Tetrakis(1-ethyl-3-methylimidazolium-5-yl)porphyrin Tetrachloride (66)

Porphyrin 21 (371 mg, 0.588 mmol) was dissolved in DMF (8 mL) in a sealed tube reactor. Ethyl iodide (7 mL, 88 mmol) was added and the sealed tube was heated at 60° C. overnight. The mixture was cooled to room temperature and concentrated by rotary evaporation. The residue was dissolved in water (20 mL) and purified by the double precipitation method to provide porphyrin 66 (349 mg, 67%) as a dark purple solid: $^1$H NMR (300 MHz, DMSO-$d_6$) δ −3.23 (s, 2H), 1.17 (m, 12H), 3.77 (m, 12H), 4.03 (m, 8H), 7.01, 7.18, 7.35 (multiple s, 8H), 8.63 (d, 4H), 9.36 (s, 4H).

2. [5,10,15,20-Tetrakis(1-ethyl-3-methylimidazolium-2-yl)porphyrinato]-manganese(III) Pentachloride (67)

Porphyrin 66 (340 mg, 0.39 mmol) was dissolved in methanol (45 mL) then Mn(OAc)$_3$.2 H$_2$O (680 mg, 2.53 mmol) was added, and the mixture was stirred at 55° C. for 3.5 h. The mixture was cooled to room temperature, filtered through Celite (to remove insoluble solids), and concentrated by rotary evaporation. The residue was purified by the double precipitation method to provide porphyrin 67 (324 mg, 85%) as a brown solid: mp>300° C.; UV-vis $\lambda_{max}$=446.5 nm; $\epsilon$=5.11×10$^4$ L/cm-mol; ES-MS m/z=1251 [(C$_{44}$H$_{48}$MnN$_{12}$)$^{+5}$+4 (CF$_3$CO$_2$$^-$)]$^+$.

Example 2

Treatment of Bronchopulmonary Dysplasia Using Aeol-V (10123)

Neonatal baboons were delivered prematurely by Caesarian section and then treated either with 100% oxygen or only sufficient PRN FIO$_2$ to maintain adequate arterial oxygenation. To establish the model, thirteen 100% oxygen treated animals and seven PRN control animals were studied. Treatment with 100% oxygen results in extensive lung injury manifested by days 9 or 10 of exposure and characterized by delayed alveolarization, lung parenchymal inflammation, and poor oxygenation. This is characteristic of the human disease, bronchopulmonary dysplasia, and is thought to be mediated, at least in part, by oxidative stress on the developing neonatal lung. In a first trial of Aeol-V, a neonatal baboon was delivered at 140 days gestation and placed in 100% oxygen. The animal received 0.25 mg/kg/24 hr given i.v. in a continuous infusion over the entire 10 day study period (see FIG. 2). This animal showed marked improvement of the oxygenation index. There was no evidence of clinical decompensation of the lungs at days 9 and 10. This suggests that Aeol-V can be used to treat oxidant stress in the premature newborn.

All documents cited above are hereby incorporated in their entirety by reference.

One skilled in the art will appreciate from a reading of this disclosure that various changes in form and detail can be made without departing from the true scope of the invention.

What is claimed is:

1. A method for treating a patient for inflammation of the lung, said method comprising administering to a patient in need an effective amount of a compound of formula

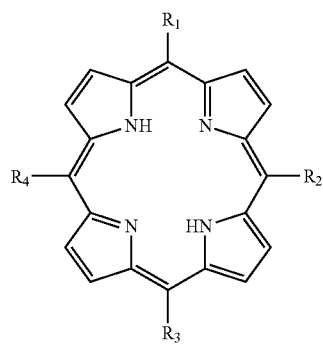

or pharmaceutically accept salt thereof, wherein

R$_1$ and R$_3$ are the same and are:

—H, —CF$_3$, —CO$_2$X,

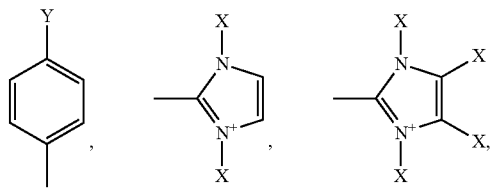

-continued

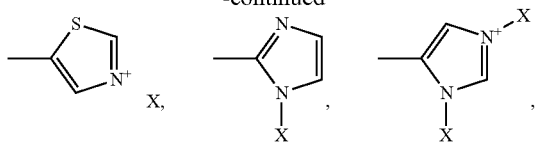

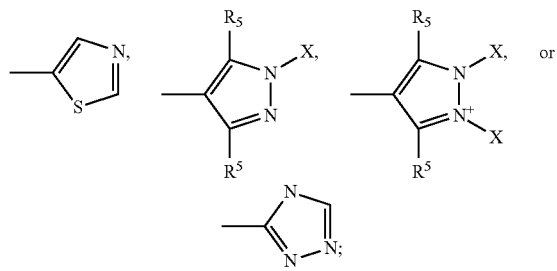

$R_2$ and $R_4$ are the same and are:

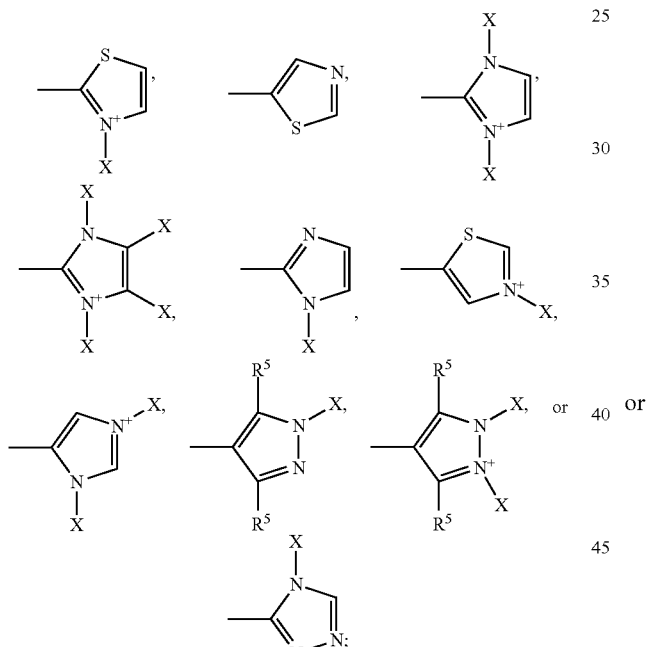

Y is halogen or —CO$_2$X,
each X is the same or different and is an alkyl; and
each $R_5$ is the same or different and is H or alkyl.

2. The method according to claim 1, wherein said inflammation of the lung is an inflammatory lung disease.

3. The method according to claim 1, wherein said inflammation of the lung is an inflammatory based disorder of asthma, emphysema, acute respiratory distress syndrome (ARDS), pneumonia, cystic fibrosis, or bronchopulmonary dysplasia.

4. The method according to claim 1, wherein said inflammation of the lung comprises respiratory fatigue.

5. The method according to claim 4, wherein said inflammation of the lung is chronic obstructive pulmonary disease.

6. The method according to claim 1, wherein said inflammation of the lung comprises the pulmonary system.

7. The method according to claim 6, wherein said inflammation of the lung is pulmonary fibrosis or pulmonary hypertension.

8. The method according to claim 3, wherein said inflammation of the lung is asthma, emphysema, ARDS or pneumonia.

9. The method according to claim 3, wherein said inflammation of the lung is bronchopulmonary dysplasia.

10. The method according to claim 1, wherein said compound is complexed with a metal selected from the group consisting of manganese, iron, copper, cobalt, nickel or zinc.

11. The method according to claim 10, wherein said compound is complexed with manganese.

12. The method according to claim 1, wherein
$R_1$ and $R_3$ are —H, —CF$_3$, —CO$_2$X,

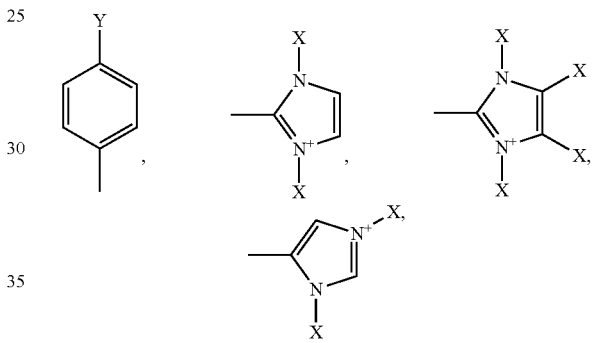

or

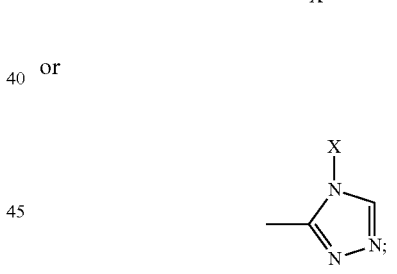

$R_2$ and $R_4$ are

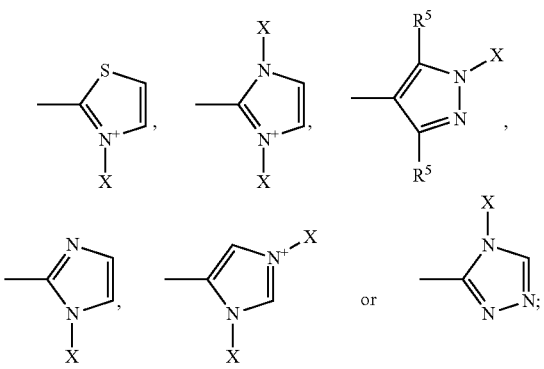

Y is —F or —CO$_2$X;

X is the same or different and is a C$_{1-4}$ alkyl; and each R$_5$ is the same or different and is H or C$_{1-4}$ alkyl.

13. The method according to claim 12, wherein X is methyl or ethyl.

14. The method according to claim 12, wherein R$_1$, R$_2$, R$_3$ and R$_4$ are the same.

15. The method according to claim 14, wherein R$_1$, R$_2$, R$_3$ and R$_4$ are

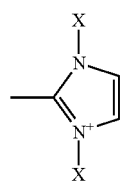

or

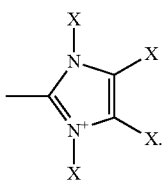

16. The method according to claim 15, wherein X is methyl or ethyl.

17. The method according to claim 16, wherein said compound is

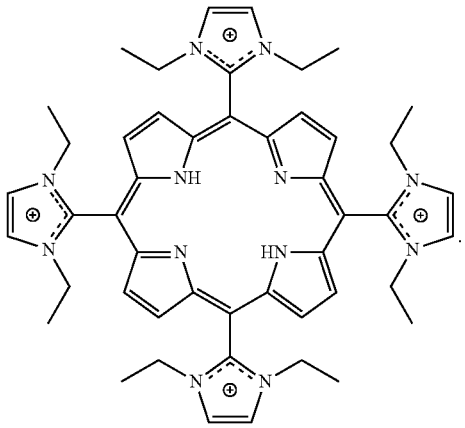

18. The method according to claim 12, wherein said compound is complexed with a metal selected from the group consisting of manganese, iron, copper, cobalt, nickel or zinc.

19. The method according to claim 18, wherein said compound is complexed with manganese.

20. The method according to claim 19, wherein said compound is

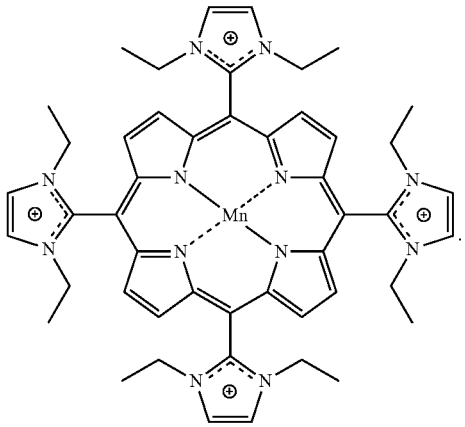

* * * * *